United States Patent [19]
Lee et al.

[11] Patent Number: 5,580,985
[45] Date of Patent: Dec. 3, 1996

[54] SUBSTITUTED PYRAZOLES FOR THE TREATMENT OF INFLAMMATION

[75] Inventors: Len F. Lee, St. Charles, Mo.; Thomas D. Penning, Elmhurst; Steven W. Kramer, Des Plaines, both of Ill.

[73] Assignee: G. D. Searle & Co., Skokie, Ill.

[21] Appl. No.: 535,688

[22] Filed: Sep. 28, 1995

Related U.S. Application Data

[63] Continuation of Ser. No. 278,297, Jul. 21, 1994, abandoned.
[51] Int. Cl.$^6$ .................... A61K 31/415; C07D 403/06
[52] U.S. Cl. .................... 548/364.1; 544/140; 544/371; 546/211; 546/256; 546/275.4; 546/276.1; 546/270.4; 546/271.4; 548/365.7
[58] Field of Search .................... 548/364.1; 514/406

[56] References Cited

U.S. PATENT DOCUMENTS

| | | |
|---|---|---|
| 3,254,093 | 5/1966 | Huisgen et al. . |
| 3,984,431 | 10/1976 | Guérémy et al. . |
| 5,134,142 | 2/1993 | Matsuo et al. . |

FOREIGN PATENT DOCUMENTS

| | | |
|---|---|---|
| 83/00330 | 2/1983 | WIPO . |
| 92/19615 | 11/1992 | WIPO . |
| WO95/31451 | 11/1995 | WIPO . |

OTHER PUBLICATIONS

T. Hla and K. Nielson, *Proc. Natl. Acad. Sci, USA*, 89, 7384 (1992).

J. Masferrer, et al, *Proc. Natl. Acad. Sci, USA*, 89, 3917 (1992).

E. Meade et al, *J. Biol. Chem.*, 268, 6610 (1993).

N. Futaki et al, *Prostaglandins*, 47, 55 (1994).

*Primary Examiner*—Robert W. Ramsuer
*Attorney, Agent, or Firm*—Joseph W. Bulock

[57] ABSTRACT

A class of pyrazolyl compounds is described for use in treating inflammation and inflammation-related disorders. Compounds of particular interest are defined by Formula II:

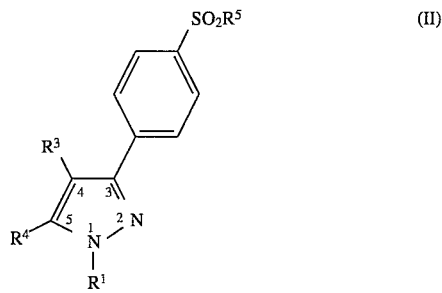

(II)

wherein $R^1$ is selected from hydrido, alkyl, alkenyl, aralkyl, alkynyl, cyanoalkyl, carboxyalkyl, aminocarbonylalkyl, arylaminocarbonylalkyl, heterocyciicalkyl, and alkoxycarbonylalkyl; wherein $R^3$ is aryl substituted at a substitutable position with halo; wherein $R^4$ is selected from hydrido and haloalkyl; and wherein $R^5$ is selected from alkyl and amino; or a pharmaceutically-acceptable salt or prodrug thereof.

44 Claims, No Drawings

SUBSTITUTED PYRAZOLES FOR THE TREATMENT OF INFLAMMATION

This is a continuation of application Ser. No. 08/278,297 filed Jul. 21, 1994, now abandoned.

FIELD OF THE INVENTION

This invention is in the field of antiinflammatory pharmaceutical agents and specifically relates to compounds, compositions and methods for treating inflammation and inflammation-associated disorders, such as arthritis.

BACKGROUND OF THE INVENTION

Prostaglandins play a major role in the inflammation process and the inhibition of prostaglandin production, especially production of $PGG_2$, $PGH_2$ and $PGE_2$, has been a common target of antiinflammatory drug discovery. However, common non-steroidal antiinflammatory drugs (NSAIDs) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved.

Previous NSAIDs have been found to prevent the production of prostaglandins by inhibiting enzymes in the human arachidonic acid/prostaglandin pathway, including the enzyme cyclooxygenase (COX). Recently, the sequence of another heretofore unknown enzyme in the human arachidonic acid/prostaglandin pathway has been reported by T. Hla and K. Nielson, *Proc. Natl. Acad. Sci, USA*, 89, 7384 (1992) and named "cyclooxygenase II (COX II)" or "prostaglandin G/H synthase II". The discovery of an inducible enzyme associated with inflammation provides a viable target of inhibition which more effectively reduces inflammation and produces fewer and less drastic side effects. Cyclooxygenase II is inducible by cytokines or endotoxins and such induction is inhibited by glucocortoids (J. Masferrer, et al, *Proc. Natl. Acad. Sci, USA*, 89, 3917 (1992)). The 6-methoxy-2-napthylacetic acid metabolite of nabumetone has been found by E. Meade et al to selectively inhibit the COX II enzyme (*J. Biol. Chem.*, 268, 6610 (1993)). In addition, Futaki et al (*Prostaglandins*, 47, 55 (1994)) have reported that N-(2-cyclohexyloxy-4-nitrophenyl)methanesulfonamide inhibits the COX II enzyme.

The references below that disclose antiinflammatory activity, show continuing efforts to find a safe and effective antiinflammatory agent. The novel pyrazoles disclosed herein are such safe and also effective antiinflammatory agents furthering such efforts. The invention's compounds are found to show usefulness in vivo as antiinflammatory agents with minimal side effects. The substituted pyrazolyl compounds disclosed herein preferably selectively inhibit cyclooxygenase II over cyclooxygenase I.

Pyrazoles have been described for use in the treatment of inflammation. U.S. Patent No. 5,134,142 to Matsuo et al describes 1,5-diaryl pyrazoles, and specifically, 1-(4-fluorophenyl)-5-[4-(methylsulfonyl)phenyl]-3-trifluoromethyl pyrazole, as having anti-inflammatory activity.

Co-pending applications Serial Nos. 8/160,553 and 8/160,594 describe substituted 1,5-substituted pyrazoles for the treatment of inflammation. U.S. Patent No. 3,254,093, to Huisgen et al, describes a process for preparing pyrazoles. Ethyl [1-benzyl-3-phenyl-pyrazole]carboxylic acid is described. WO 8300330, published February 3, 1983, describes a process for the preparation of 3,4-diphenyl-5-methyl pyrazoly derivatives.

WO 9219615, published November 12, 1992, describes pyrazolyl compounds having fungicidal properties.

U.S. Patent No. 3,984,431, to Guérémy and Renault, describes derivatives of pyrazolyl-5-acetic acid as having antiinflammatory activity. Specifically, [1-isobutyl-3,4-diphenyl-1H-pyrazol-5-yl]acetic acid is described.

DESCRIPTION OF THE INVENTION

A class of substituted pyrazolyl compounds useful in treating inflammation-related disorders is defined by Formula I:

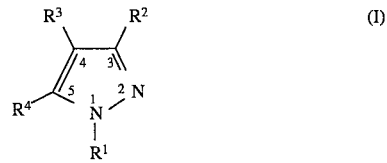

wherein $R^1$ is a radical selected from hydrido, alkyl, alkenyl, alkynyl, haloalkyl, aralkyl, heterogyclicalkyl, heteroaralkyl, hydroxyalkyl, alkoxyalkyl, cyanoalkyl, aminoalkyl, alkylaminoalkyl, carboxyalkyl, alkoxycarbonylalkyl, alkylaminocarbonylalkyl, N-hydroxyaminocarbonylalkyl, N-hydroxy-N-alkyl-aminocarbonylalkyl, arylaminocarbonylalkyl and aminocarbonylalkyl;

wherein $R^2$ is aryl substituted at a substitutable position with a radical selected from alkylsulfonyl and sulfamyl;

wherein $R^3$ is selected from aryl, cycloalkyl, cycloalkenyl and heterocyclo; wherein $R^3$ is optionally substituted at a substitutable position with one or more radicals selected from halo, alkylthio, alkylsulfinyl, alkyl, cyano, carboxyl, alkoxycarbonyl, aminocarbonyl, alkylaminocarbonyl, arylaminocarbonyl, N-alkyl-N-arylaminocarbonyl, haloalkyl, hydroxyl, alkoxy, hydroxyalkyl, haloalkoxy, amino, alkylamino, arylamino, heterocyclo and nitro; and wherein $R^4$ is selected from hydrido, alkyl, haloalkyl, cyano, acyl, alkoxy, carboxyl, carboxyalkyl, alkoxycarbonyl, alkoxycarbonylalkyl, aralkoxycarbonylalkyl, aminocarbonyl, alkylaminocarbonyl, arylaminocarbonyl, N-alkyl-N-arylaminocarbonyl, aminocarbonylalkyl, hydroxyalkyl and aralkoxyalkyl;

or a pharmaceutically-acceptable salt or prodrug thereof.

Compounds of Formula I would be useful for, but not limited to, the treatment of inflammation in a subject, and for treatment of other inflammation-associated disorders, such as, as an analgesic in the treatment of pain and headaches, or as an antipyretic for the treatment of fever. For example, compounds of Formula I would be useful to treat arthritis, including but not limited to rheumatoid arthritis, spondyloarthopathies, gouty arthritis, osteoarthritis, systemic lupus erythematosus and juvenile arthritis. Such compounds of Formula I would be useful in the treatment of asthma, bronchitis, menstrual cramps, tendinitis, bursiris, and skin related conditions such as psoriasis, eczema, burns and dermatitis. Compounds of Formula I also would be useful to treat gasrointestinal conditions such as inflammatory bowel disease, Crohn's disease, gastritis, irritable bowel syndrome and ulcerative coliris and for the prevention of colorectal cancer. Compounds of Formula I would be useful in treating inflammation in such diseases as vascular diseases, migraine headaches, periarteritis nodosa, thyroidiris, aplastic anemia, Hodgkin's disease, sclerodoma, rheumatic fever, type I diabetes, myasthenia gravis, sarcoidosis, nephrotic syndrome, Behcet's syndrome, polymyositis, gingivitis, hypersensitivity, conjunctivitis, swelling occurring after injury, myocardial ischemia, and the like. The compounds are useful as anti-inflammatory agents, such as for the treatment of arthritis, with the additional benefit of having significantly less harmful side effects.

The present invention preferrably includes compounds which selectively inhibit cyclooxygenase II over cyclooxygenase I and do not significantly inhibit one or more other arachidonic pathway steps, such as thromboxane $B_2$ ($TXB_2$) production.

Preferably, the compounds have a cyclooxygenase II $IC_{50}$ of less than about 0.1 µM, and also have a selectivity ratio of cyclooxygenase II inhibition over cyclooxygenase I inhibition of at least 50, and more preferably of at least 100. Even more preferably, the compounds have a cyclooxygenase I $IC_{50}$ of greater than about 0.5 µM, and more preferably of greater than 5 µM. Such preferred selectivity may indicate an ability to reduce the incidence of common NSAID-induced side effects.

A preferred class of compounds consists of those compounds of Formula I wherein $R^1$ is selected from hydrido, lower alkyl, lower alkenyl, lower alkynyl, lower haloalkyl, lower aralkyl, lower heterocyclicalkyl, lower heteroaralkyl, lower hydroxyalkyl, lower alkoxyalkyl, lower cyanoalkyl, lower aminoalkyl, lower alkylaminoalkyl, lower carboxyalkyl, lower alkoxycarbonylalkyl, lower alkylaminocarbonylalkyl, lower N-hydroxyaminocarbonylalkyl, lower N-hydroxy-N-alkyl-aminocarbonylalkyl, lower arylaminocarbonylalkyl and lower aminocarbonylalkyl;

wherein $R^2$ is aryl selected from phenyl, naphthyl and biphenyl, wherein $R^2$ is substituted at a substitutable position with a radical selected from lower alkylsulfonyl and sulfamyl;

wherein $R^3$ is selected from aryl, lower cycloalkyl, lower cycloalkenyl and heterocyclo; wherein $R^3$ is optionally substituted at a substitutable position with one or more radicals selected from halo, lower alkylthio, lower alkylsulfinyl, lower alkyl, cyano, carboxyl, lower alkoxycarbonyl, aminocarbonyl, lower alkylaminocarbonyl, lower arylaminocarbonyl, lower N-alkyl-N-arylaminocarbonyl, lower haloalkyl, hydroxyl, lower alkoxy, lower hydroxyalkyl, lower haloalkoxy, amino, lower alkylamino, lower arylamino, heterocyclo and nitro; and wherein $R^4$ is selected from hydrido, lower alkyl, lower haloalkyl, cyano, acyl, lower alkoxy, carboxyl, lower carboxyalkyl, lower alkoxycarbonyl, lower alkoxycarbonylalkyl, lower aralkoxycarbonylalkyl, aminocarbonyl, lower alkylaminocarbonyl, lower arylaminocarbonyl, lower N-alkyl-N-arylaminocarbonyl, lower aminocarbonylalkyl, lower hydroxyalkyl and lower aralkoxyalkyl.

A class of compounds of particular interest consists of those compounds of Formula I wherein $R^1$ is selected from hydrido, methyl, ethyl, isopropyl, tert-butyl and isobutyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, ethylenyl, propylenyl, butenyl, pentenyl, isopropylenyl, isobutylenyl, propargyl, benzyl, phenylethyl, phenylpropyl, morpholinomethyl, pyrrolidinylmethyl, piperazinylmethyl, piperidinylmethyl, pyridylmethyl, thienylmethyl, hydroxymethyl, hydroxyethyl, methoxymethyl, ethoxymethyl, cyanomethyl, aminomethyl, methylaminomethyl, formyl, acetyl, propanyl, butanyl, methoxycarbonylmethyl, ethoxycarbonylethyl, N-methylaminocarbonylmethyl, N,N-dimethylaminocarbonylmethyl, N-hydroxyaminocarbonylmethyl, N-hydroxy-N-methylaminocarbonylmethyl, N-phenylaminocarbonylmethyl and aminocarbonylmethyl;

wherein $R^2$ is aryl selected from phenyl, naphthyl and biphenyl, wherein the aryl radical is substituted at a substitutable position with a radical selected from methylsulfonyl, ethylsulfonyl and sulfamyl;

wherein $R^3$ is selected from phenyl, naphthyl, biphenyl, cyclohexyl, cyclopentyl, cycloheptyl, 1-cyclohexenyl, 2-cyclohexenyl, 3-cyclohexenyl, 4-cyclohexenyl, 4-methylcyclohex-4-en-1-yl, 1-cyclopentenyl, pyridyl, thienyl, thiazolyl, oxazolyl, furyl and pyrazinyl; wherein $R^3$ is optionally substituted at a substitutable position with one or more radicals selected from fluoro, chloro, bromo, methylthio, methylsulfinyl, cyano, methyl, ethyl, isopropyl, tert-butyl, isobutyl, carboxyl, aminocarbonyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, N-methylaminocarbonyl, N-ethylaminocarbonyl, N-isopropylaminocarbonyl, N-propylaminocarbonyl, N-butylaminocarbonyl, N-isobutylaminocarbonyl, N-tert-butylaminocarbonyl, N-pentylaminocarbonyl, N,N-dimethylaminocarbonyl, N-methyl-N-ethylaminocarbonyl, N-phenylaminocarbonyl, N-(3-fluorophenyl)aminocarbonyl, N-(4-methylphenyl)aminocarbonyl, N-(3chlorophenyl) aminocarbonyl, N-(4-methoxyphenyl)aminocarbonyl, N-methyl-N-phenylaminocarbonyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, methoxy, methylenedioxy, ethoxy, propoxy, n-butoxy, trifluoromethoxy, hydroxymethyl, hydroxyethyl, hydroxypropyl, amino, nitro, methylamino, dimethylamino, phenylamino, morpholino, pyrrolidinyl, piperazinyl and piperidinyl;

wherein $R^4$ is selected from hydrido, methyl, ethyl, isopropyl, tert-butyl, isobutyl, methoxy, ethoxy, propoxy, n-butoxy, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, cyano, formyl, carboxyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, methoxycarbonylmethyl, benzyloxycarbonylmethyl, aminocarbonyl, N-methylaminocarbonyl, N-ethylaminocarbonyl, N-isopropylaminocarbonyl, N-propylaminocarbonyl, N-butylaminocarbonyl, N-isobutylaminocarbonyl, N-tertbutylaminocarbonyl, N-pentylaminocarbonyl, N,N-dimethylaminocarbonyl, N-methyl-N-ethylaminocarbonyl, N-phenylaminocarbonyl, N-(3-fluorophenyl)aminocarbonyl, N-(4-methylphenyl)aminocarbonyl, N-(3-chlorophenyl)aminocarbonyl, N-(4-methoxyphenyl)aminocarbonyl, N-methyl-N-phenylaminocarbonyl, aminocarbonylmethyl, hydroxypropyl, hydroxymethyl, hydroxyethyl, butanyl, acetyl, propanyl and benzyloxymethyl.

A second preferred class of compounds consists of those compounds of Formula I wherein $R^2$ is aryl substituted at a substitutable position with alkylsulfonyl; or a pharmaceutically-acceptable salt thereof.

A second more preferred class of compounds consists of those compounds of Formula I wherein $R^1$ is selected from hydrido, lower alkyl, lower alkenyl, lower alkynyl, lower haloalkyl, lower aralkyl, lower heterocyclicalkyl, lower heteroaralkyl, lower hydroxyalkyl, lower alkoxyalkyl, lower cyanoalkyl, lower aminoalkyl, lower alkylaminoalkyl, lower carboxyalkyl, lower alkoxycarbonylalkyl, lower alkylaminocarbonylalkyl, lower N-hydroxyaminocarbonylalkyl, lower N-hydroxy-N-alkyl-aminocarbonylalkyl, lower arylaminocarbonylalkyl and lower aminocarbonylalkyl;

wherein $R^2$ is aryl selected from phenyl, naphthyl and biphenyl, wherein the aryl radical is substituted at a substitutable position with lower alkylsulfonyl;

wherein $R^3$ is selected from aryl, lower cycloalkyl, lower cycloalkenyl and heterocyclo; wherein $R^3$ is optionally substituted at a substitutable position with one or more radicals selected from halo, lower alkylthio, lower alkylsulfinyl, lower alkyl, cyano, carboxyl, lower alkoxycarbonyl, aminocarbonyl, lower alkylaminocarbonyl, lower arylaminocarbonyl, lower N-alkyl-N-arylaminocarbonyl, lower haloalkyl, hydroxyl, lower alkoxy, lower hydroxyalkyl, lower haloalkoxy, amino, lower alkylamino, lower arylamino, heterocyclo and nitro; and wherein $R^4$ is selected from hydrido, lower alkyl, lower haloalkyl, cyano, acyl, lower alkoxy, carboxyl, lower carboxyalkyl, lower alkoxycarbonyl, lower alkoxycarbonylalkyl, lower aralkoxycarbonylalkyl, aminocarbonyl, lower alkylaminocarbonyl, lower arylaminocarbonyl, lower N-alkyl-N-arylaminocarbonyl, lower aminocarbonylalkyl, lower hydroxyalkyl and lower aralkoxyalkyl.

A second class of compounds of particular interest consists of those compounds of Formula I wherein $R^1$ is selected from hydrido, methyl, ethyl, isopropyl, tert-butyl and isobutyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, ethylenyl, propylenyl, butenyl, pentenyl, isopropylenyl, isobutylenyl, propargyl, benzyl, phenylethyl, phenylpropyl, morpholinomethyl, pyrrolidinylmethyl, piperazinylmethyl, piperidinylmethyl, pyridylmethyl, thienylmethyl, hydroxymethyl, hydroxyethyl, methoxymethyl, ethoxymethyl, cyanomethyl, aminomethyl, methylminomethyl, formyl, acetyl, propanyl, butanyl, methoxycarbonylmethyl, ethoxycarbonylethyl, N-methylaminocarbonylmethyl, N,N-dimethylaminocarbonylmethyl, N-hydroxyaminocarbonylmethyl, N-hydroxy-N-methylaminocarbonylmethyl, N-phenylaminocarbonylmethyl and aminocarbonylmethyl;

wherein $R^2$ is aryl selected from phenyl, naphthyl and biphenyl, wherein the aryl radical is substituted at a substitutable position with a radical selected from methylsulfonyl and ethylsulfonyl;

wherein $R^3$ is selected from phenyl, naphthyl, biphenyl, cyclohexyl, cyclopentyl, cycloheptyl, 1-cyclohexenyl, 2-cyclohexenyl, 3-cyclohexenyl, 4-cyclohexenyl, 4-methylcyclohex-4-en-1-yl, 1-cyclopentenyl, pyridyl, thienyl, thiazolyl, oxazolyl, furyl and pyrazinyl; wherein $R^3$ is optionally substituted at a substitutable position with one or more radicals selected from fluoro, chloro, bromo, methylthio, methylsulfinyl, cyano, methyl, ethyl, isopropyl, tert-butyl, isobutyl, carboxyl, aminocarbonyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, N-methylaminocarbonyl, N-ethylaminocarbonyl, N-isopropylaminocarbonyl, N-propylaminocarbonyl, N-butylaminocarbonyl, N-isobutylaminocarbonyl, N-tert-butylaminocarbonyl, N-pentylaminocarbonyl, N,N-dimethylaminocarbonyl, N-methyl-N-ethylaminocarbonyl, N-phenylaminocarbonyl, N-(3-fluorophenyl)aminocarbonyl, N-(4-methylphenyl) aminocarbonyl, N-(3-chlorotphenyl)aminocarbonyl, N-(4-methoxyphenyl)aminocarbonyl, N-methyl-N-phenylaminocarbonyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, methoxy, methylenedioxy, ethoxy, propoxy, n-butoxy, trifluoromethoxy, hydroxymethyl, hydroxyethyl, hydroxypropyl, amino, nitro, methylamino, dimethylamino, phenylamino, morpholino, pyrrolidinyl, piperazinyl and piperidinyl;

wherein $R^4$ is selected from hydrido, methyl, ethyl, isopropyl, tert-butyl, isobutyl, methoxy, ethoxy, propoxy, n-butoxy, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, cyano, formyl, carboxyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, methoxycarbonylmethyl, benzyloxycarbonylmethyl, aminocarbonyl, N-methylaminocarbonyl, N-ethylaminocarbonyl, N-isopropylaminocarbonyl, N-propylaminocarbonyl, N-butylaminocarbonyl, N-isobutylaminocarbonyl, N-tert-butylaminocarbonyl, N-pentylaminocarbonyl, N,N-dimethylaminocarbonyl, N-methyl-N-ethylaminocarbonyl, N-phenylaminocarbonyl, N-(3-fluorophenyl)aminocarbonyl, N-(4-methylphenyl)aminocarbonyl, N-(3-chlorophenyl)aminocarbonyl, N-(4methoxyphenyl)aminocarbonyl, N-methyl-N-phenylaminocarbonyl, aminocarbonylmethyl, hydroxypropyl, hydroxymethyl, hydroxyethyl, butanyl, acetyl, propanyl and benzyloxymethyl.

A family of specific compounds of particular interest within Formula I consists of compounds and pharmaceutically-acceptable salts thereof as follows:

4-(4-fluorophenyl)-3-[4-(methylsulfonyl)phenyl]-5-(trifluoromethyl)-1H-pyrazole;

4-(4-chlorophenyl)-3-[4-(methylsulfonyl)phenyl]-5-(trifluoromethyl)-1H-pyrazole;

4-(4-methylphenyl)-3-[4-(methylsulfonyl)phenyl]-5-(trifluoromethyl)-1H-pyrazole;

4-(2,4-dichlorophenyl)-3-[4-(methylsulfonyl)phenyl]-5-(trifluoromethyl)-1H-pyrazole;

4-(3,4-dichlorophenyl)-3-[4-(methylsulfonyl)phenyl]-5-(trifluoromethyl)-1H-pyrazole;

4-(4-bromophenyl)-3-[4-(methylsulfonyl)phenyl]-5-(trifluoromethyl)-1H-pyrazole;

4-(3-chlorophenyl)-3-[4-(methylsulfonyl)phenyl]-5-(trifluoromethyl)-1H-pyrazole;

4-(2-chlorophenyl)-3-[4-(methylsulfonyl)phenyl]-5-(trifluoromethyl)-1H-pyrazole;
4-phenyl-3-[4-(methylsulfonyl)phenyl]-5-(trifluoromethyl)-1H-pyrazole;
4-(4-methoxyphenyl)-3-[4-(methylsulfonyl)phenyl]-5-(trifluoromethyl)-1H-pyrazole;
3-[4-(methylsulfonyl)phenyl]-4-(4-trifluoromethoxyphenyl)-5-(trifluoromethyl)-1H-pyrazole;
4-(2-methylphenyl)-3-[4-(methylsulfonyl)phenyl]-5-(trifluoromethyl)-1H-pyrazole;
4-(3-methylphenyl)-3-[4-(methylsulfonyl)phenyl]-5-(trifluoromethyl)-1H-pyrazole;
4-(4-fluoro-2-methylphenyl)-3-[4-(methylsulfonyl)phenyl]-5-(trifluoromethyl)-1H-pyrazole;
4-(3,5-dimethyl-4-methoxyphenyl)-3-[4-(methylsulfonyl)phenyl]-5-(trifluoromethyl)-1H-pyrazole;
4-(4-methoxy-3-methylphenyl)-3-[4-(methylsulfonyl)phenyl]-5-(trifluoromethyl)-1H-pyrazole;
4-(4-fluoro-2-methoxyphenyl)-3-[4-(methylsulfonyl)phenyl]-5-(trifluoromethyl)-1H-pyrazole;
4-(2,4-dimethylphenyl)-3-[4-(methylsulfonyl)phenyl]-5-(trifluoromethyl)-1H-pyrazole;
4-(3,4-dimethylphenyl)-3-[4-(methylsulfonyl)phenyl]-5-(trifluoromethyl)-1H-pyrazole;
4-(2,5-dichlorophenyl)-3-[4-(methylsulfonyl)phenyl]-5-(trifluoromethyl)-1H-pyrazole;
4-(4-ethoxyphenyl)-3-[4-(methylsulfonyl)phenyl]-5(trifluoromethyl)-1H-pyrazole;
4-(4-n-butoxyphenyl)-3-[4-(methylsulfonyl)phenyl]-5-(trifluoromethyl)-1H-pyrazole;
4-(2-fluorophenyl)-3-[4-(methylsulfonyl)phenyl]-5-(trifluoromethyl)-1H-pyrazole;
4-(3-fluorophenyl)-3-[4-(methylsulfonyl)phenyl]-5-(trifluoromethyl)-1H-pyrazole;
4-(2-pyridyl)-3-[4-(methylsulfonyl)phenyl]-5-(trifluoromethyl)-1H-pyrazole;
4-(3-pyridyl)-3-[4-(methylsulfonyl)phenyl]-5-(trifluoromethyl)-1H-pyrazo;
4-(4-pyridyl)-3-[4-(methylsulfonyl)phenyl]-5-(trifluoromethyl)-1H-pyrazole;
4-(4-aminophenyl)-3-[4-(methylsulfonyl)phenyl]-5-(trifluoromethyl)-1H-pyrazole;
4-(4-acetamidophenyl)-3-[4-(methylsulfonyl)phenyl]-5-(trifluoromethyl)-1H-pyrazole;
3-[4-(methylsulfonyl)phenyl]-4-(4-trifluoroacetamidophenyl)-5-(trifluoromethyl)-1H-pyrazole;
4-(3-fluoro-4-methoxyphenyl)-3-[4-(methylsulfonyl)phenyl]-5-(trifluoromethyl)-1H-pyrazole;
4-(3-fluoro-4-methylphenyl)-3-[4-(methylsulfonyl)phenyl]-5-(trifluoromethyl)-1H-pyrazole;
4-(3,5-dichloro-4-methoxyphenyl)-3-[4-(methylsulfonyl)phenyl]-5-(trifluoromethyl)-1H-pyrazole;
4-(3,5-difluoro-4-methoxyphenyl)-3-[4-(methylsulfonyl)phenyl]-5-(trifluoromethyl)-1H-pyrazole;
4-(4-(methylthio)phenyl)-3-[4-(methylsulfonyl)phenyl]-5-(trifluoromethyl)-1H-pyrazole;
4-(3-chloro-4-(methylthio)phenyl)-3-[4-(methylsulfonyl)phenyl]-5-(trifluoromethyl)-1H-pyrazole;
4-[3-[4-(methylsulfonyl)phenyl]-5-(trifluoromethyl)-1H-pyrazol-4-yl]benzoic acid;
methyl 4-[3-[4-(methylsulfonyl)phenyl]-5-(trifluoromethyl)-1H-pyrazol-4-yl]benzoate;
4-[3-[4-(methylsulfonyl)phenyl]-5-(trifluoromethyl)-1H-pyrazol-4-yl]benzamide;
4-(4-fluorophenyl)-3-[4-(methylsulfonyl)phenyl]-1H-pyrazole;
4-(4-chlorophenyl)-3-[4-(methylsulfonyl)phenyl]-1H-pyrazole;
4-(4-methylphenyl)-3-[4-(methylsulfonyl)phenyl]-1H-pyrazole;
4-(2,4-dichlorophenyl)-3-[4-(methylsulfonyl)phenyl]-1H-pyrazole;
4-(3,4-dichlorophenyl)-3-[4-(methylsulfonyl)phenyl]-1H-pyrazole;
4-(4-bromophenyl)-3-[4-(methylsulfonyl)phenyl]-1H-pyrazole;
4-(3-chlorophenyl)-3-[4-(methylsulfonyl)phenyl]-1H-pyrazole;
4-(2-chlorophenyl)-3-[4-(methylsulfonyl)phenyl]-1H-pyrazole;
3-[4-(methylsulfonyl)phenyl]-4-phenyl-1H-pyrazole;
4-(4-methoxyphenyl)-3-[4-(methylsulfonyl)phenyl]-1H-pyrazole;
3-[4-(methylsulfonyl)phenyl]-4-(4-trifluoromethoxyphenyl)-1H-pyrazole;
4-(2-methylphenyl)-3-[4-(methylsulfonyl)phenyl]-1H-pyrazole;
4-(3-methylphenyl)-3-[4-(methylsulfonyl)phenyl]-1H-pyrazole;
4-(4-fluoro-2-methylphenyl)-3-[4-(methylsulfonyl)phenyl]-1H-pyrazole;
4-(3,5-dimethyl-4-methoxyphenyl)-3-[4-(methylsulfonyl)phenyl]-1H-pyrazole;
4-(4-methoxy-3-methylphenyl)-3-[4-(methylsulfonyl)phenyl]-1H-pyrazole;
4-(4-fluoro-2-methoxyphenyl)-3-[4-(methylsulfonyl)phenyl]-1H-pyrazole;
4-(2,4-dimethylphenyl)-3-[4-(methylsulfonyl)phenyl]-1H-pyrazole;
4-(3,4-dimethylphenyl)-3-[4-(methylsulfonyl)phenyl]-1H-pyrazole;
4-(2,5-dichlorophenyl)-3-[4-(methylsulfonyl)phenyl]-1H-pyrazole;
4-(4-ethoxyphenyl)-3-[4-(methylsulfonyl)phenyl]-1H-pyrazole;
4-(4-n-butoxyphenyl)-3-[4-(methylsulfonyl)phenyl]-1H-pyrazole;
4-(2-fluorophenyl)-3-[4-(methylsulfonyl)phenyl]-1H-pyrazole;
4-(3-fluorophenyl)-3-[4-(methylsulfonyl)phenyl]-1H-pyrazole;
3-[4-(methylsulfonyl)phenyl]-4-(2-pyridyl)-1H-pyrazole;
3-[4-(methylsulfonyl)phenyl]-4-(3-pyridyl)-1H-pyrazole;
3-[4-(methylsulfonyl)phenyl]-4-(4-pyridyl)-1H-pyrazole;
4-(4-aminophenyl)-3-[4-(methylsulfonyl)phenyl]-1H-pyrazole;
4-(4-acetamidophenyl)-3-[4-(methylsulfonyl)phenyl]-1H-pyrazole;
3-[4-(methylsulfonyl)phenyl]-4-(4-trifluoroacetamidophenyl)-1H-pyrazole;
4-(3-fluoro-4-methoxyphenyl)-3-[4-(methylsulfonyl)phenyl]-1H-pyrazole;
4-(3-fluoro-4-methylphenyl)-3-[4-(methylsulfonyl)phenyl]-1H-pyrazole;
4-(3,5-dichloro-4-methoxyphenyl)-3-[4-(methylsulfonyl)phenyl]-1H-pyrazole;
4-(3,5-difluoro-4-methoxyphenyl)-3-[4-(methylsulfonyl)phenyl]-1H-pyrazole;
4-(4-(methylthio)phenyl)-3-[4-(methylsulfonyl)phenyl]-1H-pyrazole;
4-(3-chloro-4-(methylthio)phenyl)-3-[4-(methylsulfonyl)phenyl]-1H-pyrazole;
4-[3-[4-(methylsulfonyl)phenyl]-1H-pyrazol-4-yl]benzoic acid;
methyl 4-[3-[4-(methylsulfonyl)phenyl]-1H-pyrazol-4-yl]benzoate;

4-[3-[4-(methylsulfonyl)phenyl]-1H-pyrazol-4-yl]benzamide;
4-(4-chlorophenyl)-5-(difluoromethyl)-3-[4-(methylsulfonyl)phenyl]-1H -pyrazole;
5-(chlorodifluoromethyl)-4-(4-chlorophenyl)-3-[4-(methylsulfonyl)phenyl]-1H-pyrazole;
4-(4-chlorophenyl)-3-[4-(methylsulfonyl)phenyl]-5-(pentafluoroethyl)-1H-pyrazole;
4-(4-chlorophenyl)-5-cyano-3-[4-(methylsulfonyl)phenyl]-1H-pyrazole;
4-(4-chlorophenyl)-5-methyl-3-[4-(methylsulfonyl)phenyl]-1H-pyrazole;
4-(4-chlorophenyl)-5-ethyl-3-[4-(methylsulfonyl)phenyl]-1H-pyrazole;
4-(4-chlorophenyl)-3-[4-(methylsulfonyl)phenyl]-5-(hydroxymethyl)-1H-pyrazole;
5-(benzyloxymethyl)-4-(4-chlorophenyl)-3-[4-(methylsulfonyl)phenyl]-1H-pyrazole;
[4-(4-chlorophenyl)-3-[4-(methylsulfonyl)phenyl]-1H-pyrazol-5-yl]carboxylic acid;
methyl [4-(4-chlorophenyl)-3-[4-(methylsulfonyl)phenyl]-1H-pyrazol-5-yl]carboxylate;
ethyl [4-(4-chlorophenyl)-3-[4-(methylsulfonyl)phenyl]-1H -pyrazol-5-yl]carboxylate;
t-butyl [4-(4-chlorophenyl)-3-[4-(methylsulfonyl)phenyl]-1H-pyrazol-5-yl]carboxylate;
benzyl [4-(4-chlorophenyl)-3-[4-(methylsulfonyl)phenyl]-1H-pyrazol-5-yl]carboxylate;
isopropyl [4-(4-chlorophenyl)-3-[4-(methylsulfonyl)phenyl]-1H-pyrazol-5-yl]carboxylate;
[4-(4-chlorophenyl)-3-[4-(methylsulfonyl)phenyl]-1H-pyrazol-5-yl]carboxamide;
N-phenyl-[4-(4-chlorophenyl)-3-[4-(methylsulfonyl)phenyl]-1H-pyrazol-5-yl]carboxamide;
N-methyl-N-phenyl-[4-(4-chlorophenyl)-3-[4-(methylsulfonyl)phenyl]-1H -pyrazol-5-yl]carboxamide;
N,N-dimethyl-[4-(4-chlorophenyl)-3-[4-(methylsulfonyl)phenyl]-1H -pyrazol-5-yl]carboxamide;
N-(3-chlorophenyl)-[4-(4-chlorophenyl)-3-[4-(methylsulfonyl)phenyl]-1H-pyrazol-5-yl]carboxamide;
4-(4-methylphenyl)-3-[4-(methylsulfonyl)phenyl]-5-(difluoromethyl)-1H-pyrazole;
4-(4-methylphenyl)-3-[4-(methylsulfonyl)phenyl]-5-(chlorodifluoromethyl)-1H-pyrazole;
4-(4-methylphenyl)-3-[4-(methylsulfonyl)phenyl]-5-(pentafluoroethyl)-1H-pyrazole;
[4-(4-methylphenyl)-3-[4-(methylsulfonyl)phenyl]-1H-pyrazol-5-yl]carboxylic acid;
methyl [4-(4-methylphenyl)-3-[4-(methylsulfonyl)phenyl]-1H-pyrazol-5-yl]carboxylate;
[4-(4-methylphenyl)-3-[4-(methylsulfonyl)phenyl]-1H-pyrazol-5-yl]carboxamide;
N-phenyl-[4-(4-methylphenyl)-3-[4-(methylsulfonyl)phenyl]-1H-pyrazol-5-yl]carboxamide;
4-(4-fluorophenyl)-1-methyl-3-[4-(methylsulfonyl)phenyl]-5-(trifluoromethyl)-1H-pyrazole;
1-ethyl-4-(4-fluorophenyl)-3-[4-(methylsulfonyl)phenyl]-5-(trifluoromethyl)-1H-pyrazole;
1-benzyl-4-(4-fluorophenyl)-3-[4-(methylsulfonyl)phenyl]-5-(trifluoromethyl)-1H-pyrazole;
4-(4-fluorophenyl)-3-[4-(methylsulfonyl)phenyl]-1-(3-propenyl)-5-(trifluoromethyl)-1H-pyrazole;
4-(4-fluorophenyl)-3-[4-(methylsulfonyl)phenyl]-1-(3-propynyl)-5-(trifluoromethyl)-1H-pyrazole;
1-cyanomethyl-4-(4-fluorophenyl)-3-[4(methylsulfonyl)phenyl]-5-(trifluoromethyl)-1H-pyrazole;
4-(4-fluorophenyl)-3-[4-(methylsulfonyl)phenyl]-1-[2-(1H-pyrrolidin-1-yl)ethyl]-5-(trifluoromethyl)-1H-pyrazole;
ethyl [4-(4-fluorophenyl)-3-[4-(methylsulfonyl)phenyl]-5-(trifluoromethyl)-1H-pyrazol-1-yl]acetate;
N-phenyl-[4-(4-fluorophenyl)-3-[4-(methylsulfonyl)phenyl]-5-(trifluoromethyl)-1H-pyrazol-1-yl]acetamide;
[4-(4-fluorophenyl)-3-[4-(methylsulfonyl)phenyl]-5-(trifluoromethyl)-1H-pyrazol-1-yl]acetic acid;
[4-(4-fluorophenyl)-3-[4-(methylsulfonyl)phenyl]-5(trifluoromethyl)-1H-pyrazol-1-yl]acetamide;
4-(4-fluorophenyl)-1-(3-hydroxypropyl)-3-[4-(methylsulfonyl)phenyl]-5-(trifluoromethyl)-1H-pyrazole;
4-(4-fluorophenyl)-3-[4-(methylsulfonyl)phenyl]]1-[2(2-pyridyl)ethyl]-5-(trifluoromethyl)-1H-pyrazole;
4-(4-fluorophenyl)-3-[4-(methylsulfonyl)phenyl]-1-(2-phenylethyl)-5-(trifluoromethyl)-1H-pyrazole;
N-hydroxy-N-methyl-[4-(4-fluorophenyl)-3-[4-(methylsulfonyl)phenyl]-5-(trifluoromethyl)-1H-pyrazol -1-yl]acetamide;
1-[2-(dimethylamino)ethyl]-4-(4-fluorophenyl)-3-[4-(methylsulfonyl)phenyl]-5-(trifluoromethyl)-1H-pyrazole;
1-methyl-4-(4-methylphenyl)-3-[4-(methylsulfonyl)phenyl] -5-(trifluoromethyl)-1H-pyrazole;
1-ethyl-4-(4-methylphenyl)-3-[4-(methylsulfonyl)phenyl]-5-(trifluoromethyl)-1H-pyrazole;
-benzyl-4-(4-methylphenyl)-3-[4-(methylsulfonyl)phenyl]-5-(trifluoromethyl)-1H-pyrazole;
4-(4-methylphenyl)-3-[4-(methylsulfonyl)phenyl]-1-(3-propenyl) -5-(trifluoromethyl)-1H-pyrazole;
-(4-methylphenyl)-3-[4-(methylsulfonyl)phenyl ]-1-(3propynyl) -5-(trifluoromethyl)-1H-pyrazole;
1-cyanomethyl-4-(4-methylphenyl)-3-[4-(methylsulfony)phenyl]-5-(trifluoromethyl)-1-H-pyrazole;
ethyl[4-(4-methylphenyl)-3-[4-(methylsulfonyl)phenyl]-5-(trifluoromethyl)-1H-pyrazol-1-yl]acetate;
4-(4-methylphenyl)-3-[4-methylsulfonyl)phenyl]-5-(trifluoromethyl)-1-H-pyrazol-1-yl]acetic acid;
1-(3-hydroxypropyl)-4-(4-methylphenyl)-3-[4-(methylsulfonyl)phenyl]-5-(trifluoromethyl)-1H-pyrazole;
1-[2-(dimethylamino)ethyl]-4-(4-methylphenyl)-3-[4-(methylsulfonyl)phenyl]-5-(trifluoromethyl)-1H-pyrazole;
4-(4-chlorophenyl)-1-methyl-3-[4-(methylsulfonyl)phenyl]-5-(trifluoromethyl)-1H-pyrazole;
4-(4-chlorophenyl)-1-ethyl-3-[4-(methylsulfonyl)phenyl]-5-(trifluoromethyl)-1H-pyrazole;
1-benzyl-4-(4-chlorophenyl)-3-[4-(methylsulfonyl)phenyl]-5-(trifluoromethyl)-1H-pyrazole;
4-(4-chlorophenyl)-3-[4-(methylsulfonyl)phenyl]-1-(3propenyl)-5-(trifluoromethyl)-1H-pyrazole; -(4-chlorophenyl)-3-[4-(methylsulfonyl)phenyl]-1-(3propynyl)-5-(trifluoromethyl)-1H-pyrazole;
4-(4-chlorophenyl)-1-cyanomethyl-3-[4-(methylsulfonyl)phenyl]-5-(trifluoromethyl)-1H-pyrazole;
ethyl[4-(4-chlorophenyl)-3-[4-(methylsulfonyl)phenyl]-5-(trifluoromethyl)-1H-pyrazol -1-yl]acetate;
[4-(4-chlorophenyl)-3-[4-(methylsulfonyl)phenyl]-5-(trifluoromethyl)-1H-pyrazol-1-yl]acetic acid;
4-(4-chlorophenyl)-1-(3-hydroxypropyl)-3-[4-(methysulfonyl)pheny]-5-(trifluoromethyl)-1H-pyrazole;
4-(4-chlorophenyl)-1-[2-(dimethylamino)ethyl]-3-[4-(methylsulfonyl)phenyl] -5-(trifluoromethyl)-1H-pyrazole;
1-methyl-3-[4-(methylsulfonyl)phenyl]-4-phenyl -5-(trifluoromethyl)-1H-pyrazole;
-ethyl-3-[4-(methylsulfonyl)phenyl]-4-phenyl-5-(trifluoromethyl)-1H-pyrazole;
1-benzyl-3-[4-(methylsulfonyl)phenyl]-4-phenyl-5-(trifluoromethyl)-1H-pyrazole;
3-[4-(methylsulfonyl)phenyl]-4-phenyl-1-(3-propenyl)5-(trifluoromethyl)-1H-pyrazole;

3-[4-(methylsulfonyl)phenyl]-4-phenyl-1-(3-propynyl)-5-(trifluoromethyl)-1H-pyrazole;

-cyanomethyl-3-[4-(methylsulfonyl)phenyl]-4-phenyl-5-(trifluoromethyl)-1H-pyrazole;

ethyl [3-4-(methylsulfonyl)phenyl]-4-phenyl-5-(trifluoromethyl)-1H-pyrazol-1-yl]acetate;

[3-[4-(methylsulfonyl)phenyl]-4-phenyl-5-(trifuoromethyl)-1H-pyrazol-1-yl]acetic acid;

1-(3-hydroxypropyl)-3-[4-(methylsulfonyl)phenyl]-4-phenyl-5-(trifluoromethyl)-1H-pyrazole;

1-[2-(dimethylamino)ethyl]-3-[4-(methylsulfonyl)phenyl]-4-phenyl -5(trifluoromethyl)-1H-pyrazole;

4-(4-methoxyphenyl)-1-methyl-3-[4-(methylsulfonyl)phenyl]-5-(trifluoromethyl)-1H-pyrazole;

1-ethyl-4-(4-methoxyphenyl)-3-[4-(methylsulfonyl)phenyl]-5-(trifluoromethyl)-1H-pyrazole;

1-benzyl-4-(4-methoxyphenyl)-3-[4-(methylsulfonyl)phenyl]-5-(trifluoromethyl)-1H-pyrazole;

4-(4-methoxyphenyl)-3-[4-(methylsulfonyl)phenyl]-1-(3 propenyl) -5-(trifluoromethyl)-1H-pyrazole;

4-(4-methoxyphenyl)-3-[4-(methylsulfonyl)phenyl]-1-(3propynyl) -5-(trifluoromethyl)-1H-pyrazole;

1-cyanomethyl-4-(4-methoxyphenyl)-3-[4-(methylsulfonyl)phenyl]-5-(trifluoromethyl)-1H-pyrazole;

ethyl [4-(4-methoxyphenyl)-3-[4-(methylsulfonyl)phenyl]-5-(trifluoromethyl)-1H-pyrazol-1-yl]acetate;

[4-(4-methoxyphenyl)-3-[4-(methylsulfonyl)phenyl]-5-(trifluoromethyl)-1H-pyrazol-1-yl]acetic acid;

1-(3-hydroxypropyl)-4-(4-methoxyphenyl)-3-[4-methylsulfony)phenyl]-5-(trifluoromethyl)-1H-pyrazole;

1-[2-(dimethylamino)ethyl]-4-(4 -methoxyphenyl)-3-[4-(methylsulfonyl)phenyl]-5-(trifluoromethyl)-1H-pyrazole;

4-(2,4-dichlorophenyl)-1-methyl-3-[4-(methylsulfonyl)phenyl]-5-(trifluoromethyl)-1H-pyrazole;

4-(2,4-dichlorophenyl)-1-ethyl-3-[4-(methylsulfonyl)phenyl]-5-(trifluoromethyl)-1H-pyrazole;

1-benzyl-4-(2,4-dichlorophenyl)-3-[4-(methylsulfonyl)phenyl]-5-(trifluoromethyl)-1H-pyrazole;

4-(2,4-dichlorophenyl)-3-[4-(methylsulfonyl)phenyl]-1(3-propenyl)-5-(trifluoromethyl)-1H-pyrazole;

4-(2,4-dichlorophenyl)-3-[4-(methylsulfonyl)phenyl]-1(3-propynyl)-5-(trifluoromethyl)-1H-pyrazole;

1-cyanomethyl-4-(2,4-dichlorophenyl)-3-[4-(methylsulfonyl)phenyl]-5-(trifluoromethyl)-1H-pyrazole;

ethyl [4-(2,4-dichlorophenyl)-3-[4-(methylsulfonyl)phenyl]-5-(trifluoromethyl)-1H-pyrazol-1-yl]acetate;

[4-(2,4-dichlorophenyl)-3-[4-(methylsulfonyl)phenyl]5-(trifluoromethyl)-1H-pyrazol-1-yl]acetic acid;

4-(2,4-dichlorophenyl)-1-(3-hydroxypropyl)-3-[4-(methylsulfonyl)phenyl]-5-(trifluoromethyl)-1H-pyrazole;

4-(2,4-dichlorophenyl)-1-[2-(dimethylamino)ethyl]-3-[4-(methysulfonyl)phenyl]-5-(trifluoromethyl)-1H-pyrazole;

1-methyl-4-(2-methylphenyl)-3-[4-(methylsulfonyl)phenyl]-5-(trifluoromethyl)-1H-pyrazole;

1-ethyl-4-(2-methylphenyl)-3-[4-(methylsulfonyl)phenyl]-5-(trifluoromethyl)-1H-pyrazole;

1-benzyl-4-(2-methylphenyl)-3-[4-(methylsulfonyl) phenyl]-5-(trifluoromethyl)-1H-pyrazole;

4-(2-methylphenyl)-3-[4-(methylsulfonyl)phenyl]-1-(3propenyl)-5-(trifluoromethyl)-1H-pyrazole;

4-(2-methylphenyl)-3-[4-(methylsulfonyl)phenyl]-1-(3 propynyl)-5-(trifluoromethyl)-1H-pyrazole;

1-cyanomethyl-4-(2-methylphenyl)-3-[4-(methylsulfonyl)phenyl]-5-(trifluoromethyl)-1H-pyrazole;

ethyl[4-(2-methylphenyl)-3-[4-(methylsulfonyl)phenyl]-5-(trifluoromethyl)-1H-pyrazol-1-yl]acetate;

[4-(2-methylphenyl)-3-[4-(methylsulfonyl)phenyl]-5-(trifluoromethyl)-1H-pyrazol-1-yl]acetic acid;

1-(3-hydroxypropyl)-4-(2-methylphenyl)-3-[4-(methylsulfonyl)phenyl]-5-(trifluoromethyl)-1H-pyrazole;

1-[2-(dimethylamino)ethyl]-4-(2-methylphenyl)-3-[4-(methylsulfonyl)phenyl]-5-(trifluoromethyl)-1H-pyrazole;

4-(4-methoxy-3-methylphenyl)-1-methyl-3-[4-(methylsulfonyl)phenyl]-5-(trifluoromethyl)-1H-pyrazole;

1-ethyl-4-(4-methoxy-3-methylphenyl)-3-[4-(methylsulfonyl)phenyl]-5-(trifluoromethyl)-1H-pyrazole;

1-benzyl-4-(4-methoxy-3-methylphenyl)-3-[4-(methylsulfonyl)phenyl]-5-(trifluoromethyl)-1 H-pyrazole;

4-(4-methoxy-3-methylphenyl)-3-[4-(methylsulfonyl)phenyl]-1-(3-propenyl)-5 -(trifluoromethyl)-1H-pyrazole;

4-(4-methoxy-3-methylphenyl)-3-[4-(methylsulfonyl)phenyl]-1-(3-propynyl)-5 (trifluoromethyl)-1H-pyrazole;

1-cyanomethyl-4-(4-methoxy-3-methylphenyl) -3-[4 -(methylsulfonyl)phenyl]-5-(trifluoromethyl)-1H-pyrazole;

ethyl [4-(4-methoxy-3-methylphenyl)-3-[4-(methylsulfonyl)phenyl]-5-(trifluoromethyl)-1H-pyrazol-1-yl]acetate;

[4-(4-methoxy-3-methylphenyl)-3-[4-(methylsulfonyl)phenyl]-5-(trifluoromethyl)-1H-pyrazol-1-yl]acetic acid;

1-(3-hydroxypropyl)-4-(4-methoxy-3-methylphenyl)-3-[4-(methylsulfonyl)phenyl]-5-(trifluoromethyl)-H-pyrazole;

1-[2-(dimethylamino)ethyl]-4-(4-methoxy-3methylphenyl)-3-[4-(methylsulfonyl)phenyl]-5-(trifluoromethyl)-1H-pyrazole;

4-(3-fluoro-4-methoxyphenyl)-1-methyl-3-[4-(methylsulfonyl)phenyl]-5-(trifluoromethyl)-1H-pyrazole;

1-ethyl-4-(3-fluoro-4-methoxyphenyl)-3-[4-(methylsulfonyl)phenyl]-5-(trifluoromethyl)-1H-pyrazole;

1-benzyl-4-(3-fluoro-4-methoxyphenyl)-3-[4-(methylsulfonyl)phenyl]-5-(trifluoromethyl)-1H-pyrazole;

4-(3-fluoro-4-methoxyphenyl)-3-[4-(methylsulfonyl)phenyl]-1-(3-propenyl)-5(trifluoromethyl)-1H-pyrazole;

[4-(3-fluoro-4-methoxyphenyl)-3-[4-(methylsulfonyl)phenyl]-1-(3-propynyl)-5(trifluoromethyl)-1H pyrazol1yl]

1cyanomethyl-4-(3fluoro-4-methoxyphenyl)-3-[4-(methylsulfonyl)phenyl]-5-(trifluoromethyl)-1H-pyrazole;

ethyl [4-(3-fluoro-4-methoxyphenyl)-3-[4-(methylsulfonyl)phenyl]-5-(trifluoromethyl)-1H-pyrazol-1yl]acetate;

[4-(3-fluoro-4-methoxyphenyl)-3-[4-(methylsulfonyl)phenyl]-5-(trifluoromethyl)-1H-pyrazol-yl]acetic acid;

4-(3-fluoro-4-methoxyphenyl)-1-(3-hydroxypropyl)3-[4-(methylsulfonyl)phenyl]-5-(trifluoromethyl)-H-pyrazole;

1-[2-(dimethylamino)ethyl]-4-(3-fluoro-4methoxyphenyl)-3-[4-(methylsulfonyl)phenyl]-5-(trifluoromethyl)-1H-pyrazole;

4-(3-fluoro-4-methylphenyl)-1-methyl-3-[4-(methylsulfonyl)phenyl]-5-(trifluoromethyl)-1H-pyrazole;

1-ethyl-4-(3-fluoro-4-methylphenyl)-3-[4-(methylsulfonyl)phenyl]-5-(trifluoromethyl)-1H-pyrazole;

1-benzyl-4-(3-fluoro-4-methylphenyl)-3-[4-(methylsulfonyl)phenyl]-5-(trifluoromethyl)-1H-pyrazole;

4-(3-fluoro-4-methylphenyl)-3-[4-(methylsulfonyl)phenyl]-1-(3-propenyl)-5(trifluoromethyl)-1H-pyrazole;

4-(3-fluoro-4-methylphenyl)-3-[4-(methylsulfonyl)phenyl]-1-(3-propynyl)-5(trifluoromethyl)-1H-pyrazole;

1-cyanomethyl-4-(3-fluoro-4-methylphenyl)-3-[4-(methylsulfonyl)phenyl]-5-(trifluoromethyl)-1H-pyrazole;

ethyl [4-(3-fluoro-4-methylphenyl)-3-[4-(methylsulfonyl)phenyl]-5-(trifluoromethyl)-1H-pyrazol-1-yl]acetate;

[4-(3-fluoro-4-methylphenyl)-3-[4 -(methylsulfonyl)phenyl]-5-(trifluoromethyl)-1H-pyrazol-1-yl]acetic acid;

4-(3-fluoro-4-methylphenyl)-1-(3-hydroxypropyl)-3-[4-(methylsulfonyl)phenyl]-5-(trifluoromethyl)-1H-pyrazole;

1-[2-(dimethylamino)ethyl]-4-(3-fluoro-4-methylphenyl)-3-[4-(methylsulfonyl)phenyl]-5-(trifluoromethyl)-1H-pyrazole; 1-methyl-3-[4-(methylsulfonyl)phenyl]-4-(4-(methylthio)phenyl)-5-(trifluoromethyl)-1H-pyrazole;

1-ethyl-3-[4-(methylsulfonyl)phenyl]-4-(4-(methylthio)phenyl)-5-(trifluoromethyl)-1H-pyrazole;

1-benzyl-3-[4-(methylsulfonyl)phenyl]-4-(4-(methylthio)phenyl)-5-(trifluoromethyl)-1H-pyrazole;

3-[4-(methylsulfonyl)phenyl]-4-(4-(methylthio)phenyl)1-(3-propenyl)-5-(trifluoromethyl)-1H-pyrazole;

3-[4-(methylsulfonyl)phenyl]-4-(4-(methylthio)phenyl)-1-(3-propynyl)-5-(trifluoromethyl)-1H-pyrazole;

1-cyanomethyl-3-[4-(methylsulfonyl)phenyl]-4-(4-(methylthio)phenyl)-5-(trifluoromethyl)-1H-pyrazole;

ethyl [3-[4-(methylsulfonyl)phenyl]-4-(4-(methylthio)phenyl)-5-(trifluoromethyl)-1H-pyrazol-1-yl]acetate;

[3-[4-(methylsulfonyl)phenyl]-4-(4-(methylthio)phenyl)-5-(trifluoromethyl)-1H-pyrazol-1-yl]acetic acid;

1-(3-hydroxypropyl)-3-[4-(methylsulfonyl)phenyl]-4(4-(methylthio)phenyl)-5-(trifluoromethyl)-1H-pyrazole;

1-[2-(dimethylamino)ethyl]-3-[4-(methylsulfonyl)phenyl]-4-(4-(methylthio)phenyl)-5-(trifluoromethyl)-1H-pyrazole;

4-(1-cyclohexenyl)-1-ethyl-3-[4(methylsulfonyl)phenyl]-5-(trifluoromethyl)-1H-pyrazole;

4-(4-cyanophenyl)-1-ethyl-3-[4-(methylsulfonyl)phenyl]-5-(trifluoromethyl)-1H-pyrazole;

1-ethyl-3-[4-(methylsulfonyl)phenyl]-4-(2-pyrazinyl)-5-(trifluoromethyl)-1H-pyrazole;

4-(5-chloro-2-thienyl)-1-ethyl-3-[4 -(methylsulfonyl)phenyl]-5-(trifluoromethyl)-1H-pyrazole;

1-ethyl-3-[4-(methylsulfonyl)phenyl]-4-(4-(morpholino)phenyl)-5-(trifluoromethyl)-1H-pyrazole;

4-cyclohexyl-1-ethyl-3-[4-(methylsulfonyl)phenyl]-5-(trifluoromethyl)-1H-pyrazole;

1-ethyl-3-[4-(methylsulfonyl)phenyl]-4-(2-thienyl)-5-(trifluoromethyl)-1H-pyrazole;

4-(4-fluorophenyl)-1-methyl-3-[4-(methylsulfonyl)phenyl]-1H-pyrazole;

1-ethyl-4-(4-fluorophenyl)-3-[4-(methylsulfonyl)phenyl]-1H-pyrazole;

1-benzyl-4-(4-fluorophenyl)-3-[4-(methylsulfonyl)phenyl]-1H-pyrazole;

4-(4-fluorophenyl)-3-[4-(methylsulfonyl)phenyl]-1-(3-propenyl)-1H-pyrazole;

4-(4-fluorophenyl)-3-[4-(methylsulfonyl)phenyl]-1-(3-propynyl)-1H-pyrazole;

1-cyanomethyl-4-(4-fluorophenyl)-3-[4-(methylsulfonyl)phenyl]-1H -pyrazole;

4-(4-fluorophenyl)-3-[4-(methylsulfonyl)phenyl]-1-[2(1H-pyrrolidin-1-yl)ethyl]-1H-pyrazole;

ethyl [4-(4-fluorophenyl)-3-[4-(methylsulfonyl)phenyl]-1H-pyrazol-1-yl]acetate;

N-phenyl-[4-(4-fluorophenyl)-3-[4-(methylsulfonyl)phenyl]-1H -pyrazol-1-yl]acetamide;

[4-(4-fluorophenyl)-3-[4-(methylsulfonyl)phenyl]-1H-pyrazol-1-yl]acetic acid;

[4-(4-fluorophenyl)-3-[4-(methylsulfonyl)phenyl]-1H-pyrazol-1-yl]acetamide;

-(4-fluorophenyl)-1-(3-hydroxypropyl)-3-[4-(methylsulfonyl)phenyl]-1H -pyrazole;

4-(4-fluorophenyl)-3-[4-(methyl sulfonyl)phenyl]-1-[2 (2-pyridyl)ethyl]-1H-pyrazole;

4-(4-fluorophenyl)-3-[4-(methylsulfonyl)phenyl]-1-(2phenylethyl)-1H-pyrazole;

N-hydroxy-N-methyl-[4-(4-fluorophenyl)-3-[4-(methylsulfonyl)phenyl]-1H-pyrazol-1-yl]acetamide;

-[2-(dimethylamino)ethyl]-4-(4-fluorophenyl)-3-[4-(methylsulfonyl)phenyl]-1H-pyrazole;

1-methyl-4-(4-methylphenyl)-3-[4-(methylsulfonyl)phenyl]-1H -pyrazole 1-ethyl-4-(4-methylphenyl)-3-[4-(methylsulfonyl)phenyl]-1-pyrazole;

1-benzyl-4-(4-methylphenyl)-3-[4-(methylsulfonyl)phenyl]-1H-pyrazole;

4-(4-methylphenyl)-3-[4-(methylsulfonyl)phenyl]-1-(3propenyl)-1H-pyrazole;

4-(4-methylphenyl)-3-[4-(methylsulfonyl)phenyl]-1-(3propynyl)-1H-pyrazole;

1-cyanomethyl-4-(4-methylphenyl)-3-[4-(methylsulfonyl)phenyl]-1H-pyrazole;

ethyl [4-(4-methylphenyl)-3-[4(methylsulfonyl)phenyl]-1H-pyrazol-1-yl]acetate;

[4(4-methylphenyl)-3-[4-(methylsulfonyl)phenyl]-1H-pyrazol-1-yl]acetic acid;

1-(3-hydroxypropyl)-4-(4-methylphenyl)-3-[4-(methylsulfonyl)phenyl]-1H-pyrazole;

1-[2-(dimethylamino)ethyl]-4-(4-methylphenyl)-3-[4-(methylsulfonyl)phenyl]-1H-pyrazole;

4-(4-chlorophenyl)-1-methyl-3-[4-(methylsulfonyl)phenyl]-1H-pyrazole;

4-(4-chlorophenyl)-1-ethyl-3-[4-(methylsulfonyl)phenyl]-1H-pyrazole;

1-benzyl-4-(4-chlorophenyl)-3-[4-(methylsulfonyl)phenyl]-1H-pyrazole;

4-(4-chlorophenyl)-3-[4-(methylsulfonyl)phenyl]-1-(3propenyl)-1H-pyrazole;

4-(4-chlorophenyl)-3-[4-(methylsulfonyl)phenyl]-1-(3propynyl)-1H-pyrazole;

4-(4-chlorophenyl)-1-cyanomethyl-3-[4-(methylsulfonyl)phenyl]-1H -pyrazole;;

ethyl [4-(4-chlorophenyl)-3-[4-(methylsulfonyl)phenyl]-1H-pyrazol-1-yl]acetate;

[4-(4-chlorophenyl)-3-[4-(methylsulfonyl)phenyl]-1H-pyrazol-1-yl]acetic acid;

4-(4-chlorophenyl)-1-(3-hydroxypropyl)-3-[4-(methylsulfonyl)phenyl]-1H-pyrazole;

4-(4-chlorophenyl)-1-[2-(dimethylamino)ethyl]-3-[4-(methylsulfonyl)phenyl]-1H-pyrazole;

1-methyl-3-[4-(methylsulfonyl)phenyl]-4-phenyl -1H-pyrazole;

1-ethyl-3-[4-(methylsulfonyl)phenyl]-4-phenyl-1H-pyrazole;

1-benzyl-3-[4-(methylsulfonyl)phenyl]-4-phenyl -1H-pyrazole;

3-[4-(methylsulfonyl)phenyl]-4-phenyl-1-(3-propenyl)1H-pyrazole;

3-[4-(methylsulfonyl)phenyl]-4-phenyl-1-(3-propynyl)1H-pyrazole;

1-cyanomethyl-3-[4-(methylsulfonyl)phenyl]-4-phenyl1H-pyrazole;

ethyl [3-[4-(methylsulfonyl)phenyl]-4-phenyl-1H-pyrazol-1-yl]acetate;

-[3-[4-(methylsulfonyl)phenyl]-4-phenyl -1H-pyrazol-1-yl]acetic acid;

1-(3-hydroxypropyl)-3-[4-(methylsulfonyl)phenyl]-4phenyl-1H -pyrazole;

1-[2-(dimethylamino)ethyl]-3-[4-(methylsulfonyl)phenyl]-4-phenyl-1H-pyrazole;

4-(4-methoxyphenyl)-1-methyl-3-[4-(methylsulfonyl)phenyl]-1H-pyrazole;

1-ethyl-4-(4-methoxyphenyl)-3-[4-(methysulfonyl)phenyl]-1H-pyrazole;

1-benzyl-4-(4-methoxyphenyl)-3-[4-(methylsulfonyl)phenyl]-1H-pyrazole;

4-(4-methoxyphenyl)-3-[4-(methylsulfonyl)phenyl]-1-(3-propenyl)-1H-pyrazole;
4-(4-methoxyphenyl)-3-[4-(methylsulfonyl)phenyl]-1-(3propynyl)-1H-pyrazole;
1-cyanomethyl-4-(4-methoxyphenyl)-3-[4-(methylsulfonyl)phenyl]-1H-pyrazole;
ethyl-[4-(4-methoxyphenyl)-3-[4-(methylsulfonyl)phenyl]-1H-pyrazol-1-yl]acetate;
[4-(4-methoxyphenyl)-3-[4-(methylsulfonyl)phenyl]-1H-pyrazol-1-yl]acetic acid;
-(3-hydroxypropyl)-4-(4-methoxyphenyl)-3-[4-(methylsulfonyl)phenyl]-1H-pyrazole;
1-[2-(dimethylamino)ethyl]-4-(4-methoxyphenyl)-3-[4-(methylsulfonyl)phenyl]-1H-pyrazole;
4-(3-fluoro-4-methoxyphenyl)-1-methyl-3-[4-(methylsulfonyl)phenyl]-1H-pyrazole;
1-ethyl-4-(3-fluoro-4-methoxyphenyl)-3-[4-(methylsulfonyl)phenyl]-1H-pyrazole;
1-benzyl-4-(3-fluoro-4-methoxyphenyl)-3-[4-(methylsulfonyl)phenyl]-1H-pyrazole;
4-(3-fluoro-4-methoxyphenyl)-3-[4-(methylsulfonyl)phenyl]-1-(3-propenyl)-1H-pyrazole;
4-(3-fluoro-4-methoxyphenyl)-3-[4-(methylsulfonyl)phenyl]-1-(3-propynyl)-1H-pyrazole;
1-cyanomethyl-4-(3-fluoro-4-methoxyphenyl)-3-[4-(methylsulfonyl)phenyl]-1H-pyrazole;
ethyl [4-(3-fluoro-4-methoxyphenyl)-3-[4-(methylsulfonyl)phenyl]-1H-pyrazol-1-yl]acetate;
[4-(3-fluoro-4-methoxyphenyl)-3-[4-(methylsulfonyl)phenyl]-1H-pyrazol-1-yl]acetic acid;
4-(3-fluoro-4-methoxyphenyl)-1-(3-hydroxypropyl)-3-[4-(methylsulfonyl)phenyl]-1H-pyrazole;
1-[2-(dimethylamino)ethyl]-4-(3-fluoro-4-methoxyphenyl)-3-[4-(methlysulfonyl)phenyl]-1H-pyrazole;
4-(3-fluoro-4-methylphenyl)-1-methyl-3-[4-(methylsulfonyl)phenyl]-1H-pyrazole;
1-ethyl-4-(3-fluoro-4-methylphenyl)-3-[4-(methylsulfonyl)phenyl]-1H-pyrazole;
1-benzyl-4-(3-fluoro-4-methylphenyl)-3-[4-(methylsulfonyl)phenyl]-1H-pyrazole;
4-(3-fluoro-4-methylphenyl)-3-[4-(methylsulfonyl)phenyl]-1-(3-propenyl)-1H-pyrazole;
4-(3-fluoro-4-methylphenyl)-3-[4-(methylsulfonyl)phenyl]-1-(3-propynyl)-1H-pyrazole;
1-cyanomethyl-4-(3-fluoro-4-methylphenyl)-3-[4-(methylsulfonyl)phenyl]-1H-pyrazole;
ethyl [4-(3-fluoro-4-methylphenyl)-3-[4-(methylsulfonyl)phenyl]-1H-pyrazol-1-yl]acetate;
[4-(3-fluoro-4-methylphenyl)-3-[4-(methylsulfonyl)phenyl]-1H-pyrazol-1-yl]acetic acid;
4-(3-fluoro-4-methylphenyl)-1-(3-hydroxypropyl)-3-[4-(methylsulfonyl)phenyl]-1H-pyrazole;
1-[2-(dimethylamino)ethyl]-4-(3-fluoro-4methylphenyl)-3-[4-(methylsulfonyl)phenyl]-1H-pyrazole;
4-(4-chlorophenyl)-5-(difluoromethyl)-1-ethyl-3-[4-(methylsulfonyl)phenyl]-1H-pyrazole;
4-(4-chlorophenyl)-1-ethyl-3-[4-(methylsulfonyl)phenyl]-5-(pentafluoroethyl)-1H-pyrazole;
4-(4-chlorophenyl)-5-cyano-1-ethyl-3-[4-(methylsulfonyl)phenyl]-1H-pyrazole;
4-(4-chlorophenyl)-1-ethyl-5-methyl-3-[-4-(methylsulfonyl)phenyl]-1H-pyrazole;
4-(4-chlorophenyl)-1-ethyl-5-(hydroxymethyl)-3-[4-(methylsulfonyl)phenyl]-1H-pyrazole;
5-(benzyloxymethyl)-4-(4-chlorophenyl)-1-ethyl-3-[4-(methylsulfonyl)phenyl]-1H-pyrazole;
[4-(4-chlorophenyl)-1-ethyl-3-[4-(methylsulfonyl)phenyl]-1H-pyrazol-5-yl] carboxylic acid;
methyl [4-(4-chlorophenyl)-1ethyl-3-[4-(methylsulfonyl)phenyl]-1H-pyrazol-5-yl] carboxylate;
N-phenyl-[4-(4-chlorophenyl)-1-ethyl-3-[4-(methylsulfonyl)phenyl]-1H-pyrazol-5-yl]carboxamide;
1-benzyl-4-(4-chlorophenyl)-5-(difluoromethyl)-3-[4-(methylsulfonyl)phenyl]-1H-pyrazole;
1-benzyl-4-(4-chlorophenyl)-3-[4-(methylsulfonyl)phenyl]-5-(pentafluoroethyl)-1H-pyrazole;
1-benzyl-4-(4-chlorophenyl)-5-cyano-3-[4-(methylsulfonyl)phenyl]-1H-pyrazole;
1-4-benzyl-4-(4-chlorophenyl)-5-methyl-3-[4-(methylsulfonyl)phenyl]-1H-pyrazole;
1-benzyl-4-(4-chlorophenyl)-5-(hydroxymethyl)-3-[4-(methylsulfonyl)phenyl]-1H-pyrazole;
1-benzyl-5-(benzyloxymethyl)-4-(4-chlorophenyl)-3-[4-(methylsulfonyl)phenyl]-1H-pyrazole;
[1-benzyl-4-(4-chlorophenyl)-3-[4-methylsulfonyl)phenyl]-1H-pyrazol-5-yl] carboxylic acid;
methyl [1-benzyl-4-(4-chlorophenyl)-3-[4-(methylsulfonyl)phenyl]-1H-pyrazol-5-yl]carboxylate;
N-phenyl-[1-benzyl-4-(4-chlorophenyl)-3-[4-(methylsulfonyl)phenyl]-1H-pyrazol-5-yl]carboxamide;
4-(4-chlorophenyl)-1-(cyanomethyl)-5-(difluoromethyl)3-[4-(methylsulfonyl)phenyl]-1H-pyrazole;
4-(4-chlorophenyl)-1-ethyl-3-[4-(methylsulfonyl)phenyl]-5-(pentafluoroethyl)-1H-pyrazole;
4(4-chlorophenyl)-5-cyano-1-(cyanomethyl)-3-[4-(methylsulfonyl)phenyl]-1H-pyrazole;
4-(4-chlorophenyl)-1-(cyanomethyl)-5-methyl-3-[4-(methylsulfonyl)phenyl]-1H-pyrazole;
4-(4-chlorophenyl)-1-(cyanomethyl)-3-[4-(methylsulfonyl)phenyl]-5-(hydroxymethyl)-1H-pyrazole;
5-(benzyloxymethyl)-4-(4-chlorophenyl)-1-(cyanomethyl)-3-[4-(methylsulfonyl)phenyl]-1H-pyrazole;
[4-(4-chlorophenyl)-1-(cyanomethyl)-3-[4-(methylsulfonyl)pheny1H-pyrazol-5-yl] carboxylic acid;
methyl [4-(4-chlorophenyl)-1-(cyanomethyl)-3-[4-(methylsulfonyl)phenyl]-1H-pyrazol-5-yl]carboxylate;
N-phenyl-[4-(4-chlorophenyl)-1-(cyanomethyl)-3-[4-(methylsulfonyl)phenyl]-1H-pyrazol-5-yl]carboxamide;
4-(4-chlorophenyl)-5-(difluoromethyl)-3-[4-(methylsulfonyl)phenyl]-1-(3-propenyl)-1H-pyrazole;
4-(4-chlorophenyl)-3-[4-(methylsulfonyl)phenyl]-5-(pentafluoroethyl)-1-(3-propenyl)-1H-pyrazole;
4-(4-chlorophenyl)-5-cyano-3-[4-(methylsulfonyl)phenyl]-1-(3-propenyl)-1H-pyrazole;
4-(4-chlorophenyl)-5-methyl-3-[4-(methylsulfonyl)phenyl]-1-(3-propenyl)-1H-pyrazole;
4-(4-chlorophenyl)-5-(hydroxymethyl)-3-[4-(methylsulfonyl)phenyl]-1-(3-propenyl)-1H-pyrazole;
5-(benzyloxymethyl)-4-(4-chlorophenyl)-3-[4-(methylsulfonyl)phenyl]-1-(3-propenyl)-1H-pyrazole;
4-(4-chlorophenyl)-3-[4-(methylsulfonyl)phenyl]-1-(3 propenyl)-1H-pyrazol-5-yl]carboxylic acid;
methyl [4-(4-chlorophenyl)-3-[4-(methylsulfonyl)phenyl]-1-(3-propenyl)-1H-pyrazol-5-yl]carboxylate;
N-phenyl -[4-(4-chlorophenyl)-3-[4-(methylsulfonyl)phenyl]-1-(3-propenyl)-1H-pyrazol-5-yl]carboxamide;
4-(4-chlorophenyl)-5-(difluoromethyl)-3-[4-(methylsulfonyl)phenyl]-1-(2-phenylethyl)-1H-pyrazole;
4-(4-chlorophenyl)-3-[4-(methylsulfonyl)phenyl]-5-(pentafluoroethyl)-1-(2-phenylethyl)-1H-pyrazole;
4 -(4-chlorophenyl)-5-cyano-3-[4-(methylsulfonyl)phenyl]-1-(2-phenylethyl)-1H-pyrazole;
4-(4-chlorophenyl)-5-methyl-3-[4-(methylsulfonyl)phenyl]-1-(2-phenylethyl)-1H-pyrazole;
4-(4-chlorophenyl)-5-(hydroxymethyl)-3-[4-(methylsulfonyl)phenyl]-1-(2-phenylethyl)-1H-pyrazole;

5-(benzyloxymethyl)-4-(4-chlorophenyl)-3-[4-(methylsulfonyl)phenyl]-1-(2-phenylethyl)-1H-pyrazole;
4-(4-chlorophenyl)-3-[4-(methylsulfonyl)phenyl]-1-(2phenylethyl)-1H-pyrazol-5-yl]carboxylic acid;
methyl [4-(4-chlorophenyl)-3-[4-(methylsulfonyl)phenyl]-1-(2-phenylethyl)-1H-pyrazol-5-yl]carboxylate;
N-phenyl-[4-(4-chlorophenyl)-3-[4-(methylsulfonyl)phenyl]-1-(2-phenyl ethyl)-1H-pyrazol-5-yl]carboxamide;
5-(difluoromethyl)-1-ethyl-4-(4-methylphenyl)-3-[4 -(methylsulfonyl)phenyl]-1H-pyrazole;
1-ethyl-4-(4-methylphenyl)-3-[4-(methylsulfonyl)phenyl]-5-(pentafluoroethyl)-1H-pyrazole;
5-cyano-1-ethyl-4-4-methylphenyl)-3-[4 -(methylsulfonyl)phenyl]-1H-pyrazole;
-ethyl-5-methyl-4-(4-methylphenyl)-3-[4-(methylsulfonyl)phenyl]-1H -pyrazole;
1-ethyl-5-(hydroxymethyl)-4-(4-methylphenyl)-3-[4 -(methylsulfonyl)phenyl]-1H-pyrazole;
5-(benzyloxymethyl)-1-ethyl-4-(4-methylphenyl)-3-[4-(methylsulfonyl)phenyl]-1H-pyrazole;
[-ethyl-4-(4-methylphenyl)-3-[4-(methylsulfonyl)phenyl]-1H-pyrazol-5-yl]carboxylic acid;
methyl [1-ethyl-4-(4-methylphenyl)-3-[4-(methylsulfonyl)phenyl]-1H-pyrazol-5-yl ]carboxylate;
N-phenyl-[1-ethyl-4-(4-methylphenyl)-3-[4-(methylsulfonyl)phenyl]-1H -pyrazol-5-yl ]carboxamide;
1-benzyl-5-(difluoromethyl)-4-(4-methylphenyl)-3-[4-(methylsulfonyl)phenyl]-1H-pyrazole;
1-benzyl-4-(4-methylphenyl)-3-[4-(methylsulfonyl)phenyl]-5-(pentafluoroethyl)-1H-pyrazole;
1-benzyl-5-cyano-4-(4-methylphenyl)-3-[4-(methylsulfonyl)phenyl]-1H-pyrazole;
1-benzyl-5-methyl-4-(4-methylphenyl)-3-[4-(methylsulfonyl)phenyl]-1H -pyrazole;
1-benzyl-5-(hydroxymethyl)-4-(4-methylphenyl)-3-[4-(methylsulfonyl)phenyl]-1H-pyrazole;
1-benzyl-5-(benzyloxymethyl)-4-(4-methylphenyl)-3-[4-(methylsulfonyl)phenyl]-1H-pyrazole;
[1-benzyl-4-(4-methylphenyl)-3-[4-(methylsulfonyl)phenyl]-1H-pyrazol-5-yl] carboxylic acid;
methyl [1-benzyl-4-(4-methylphenyl)-3-[4-(methylsulfonyl)phenyl]-1H-pyrazol-5-yl ]carboxylate;
N-phenyl -[1-benzyl-4-(4-methylphenyl)-3-[4-(methylsulfonyl)phenyl]-1H-pyrazol-5 yl]carboxamide;
-(cyanomethyl)-5-(difluoromethyl)-4-(4-methylphenyl)3-[4-(methylsulfonyl)phenyl]-1H-pyrazole;
1-ethyl-4-(4-methylphenyl)-3-[4-(methylsulfonyl)phenyl]-5-(pentafluoroethyl)-1H-pyrazole;
5-cyano-1-(cyanomethyl)-4-(4-methylphenyl)-3-[4-(methylsulfonyl)phenyl]-1H -pyrazole;
1-(cyanomethyl)-5-methyl-4-(4-methylphenyl)-3-[4-(methylsulfonyl)phenyl]-1H-pyrazole;
1-(cyanomethyl)-4-(4-methylphenyl)-3-[4-(methylsulfonyl)phenyl]-5-(hydroxymethyl)-1H-pyrazole;
5-(benzyloxymethyl)-1-(cyanomethyl)-4-(4methylphenyl)-3-[4-(methylsulfonyl)phenyl]-1H-pyrazole;
[1-(cyanomethyl)-4-(4-methylphenyl)-3-[4-(methylsulfonyl)phenyl]-1H -pyrazol-5-yl] carboxylic acid;
methyl [1-(cyanomethyl)-4-(4-methylphenyl)-3-[4-(methylsulfonyl)phenyl]-1H -pyrazol-5-yl ]carboxylate;
N-phenyl-[1-(cyanomethyl)-4-(4-methylphenyl)-3-[4-(methylsulfonyl)phenyl]-1H-pyrazol-5-yl ]carboxamide;
5-(difluoromethyl)-4-(4-methylphenyl)-3-[4-(methylsulfonyl)phenyl]-1-(3-propenyl)-1H-pyrazole;
4-(4-methylphenyl)-3-[4-(methyl sulfonyl)phenyl]-5-(pentafluoroethyl)-1-(3-propenyl)-1H-pyrazole;
5-cyano-4-(4-methylphenyl)-3-[4-(methylsulfonyl)phenyl]-1-(3-propenyl)-1H-pyrazole;
5-methyl-4-(4-methylphenyl)-3-[4-(methylsulfonyl)phenyl]- 1-(3-propenyl)-1H-pyrazole;
5-(hydroxymethyl)-4-(4-methylphenyl)-3-[4 -(methylsulfonyl)phenyl]-1-(3-propenyl)-1H-pyrazole;
5-(benzyloxymethyl)-4-(4-methylphenyl)-3-[4-(methylsulfonyl)phenyl]-1-(3-propenyl)-1H-pyrazole;
[4-(4-methylphenyl)-3-[4-(methylsulfonyl)phenyl]-1-(3 propenyl)-1H-pyrazol-5-yl]carboxylic acid;
methyl [4-(4-methylphenyl)-3-[4-(methylsulfonyl)phenyl]-1-(3-propenyl)-1H-pyrazol-5-yl]carboxylate;
N-phenyl-[4-(4-methylphenyl)-3-[4-(methylsulfonyl)phenyl]-1-(3-propenyl)-1H-pyrazol-5-yl]carboxamide;
-(difluoromethyl)-4-(4-methylphenyl)-3-[4-(methylsulfonyl)phenyl]-1-(2-phenylethyl)-1H-pyrazole;
4-(4-methylphenyl)-3-[4-(methylsulfonyl)phenyl]-5-(pentafluoroethyl)-1-(2-phenylethyl)-1H-pyrazole; -
5cyano-4-(4-methylphenyl)-3-[4 -(methylsulfonyl)phenyl]-1-(2-phenylethyl)-1H-pyrazole;
5-methyl-4-(4-methylphenyl)-3-[4 -(methylsulfonyl)phenyl]-1-(2-phenylethyl)-1H-pyrazole;
5-(hydroxymethyl)-4-(4-methylphenyl)-3-[4-(methylsulfonyl)phenyl]-1-(2-phenylethyl)-1H-pyrazole;
5-(benzyloxymethyl)-4-(4-methylphenyl)-3-[4-(methylsulfonyl)phenyl]-1-(2-phenylethyl)-1H-pyrazole;
[4-(4-(4-methylphenyl)-3-[4-(methylsulfonyl)phenyl]-1-(2 phenylethyl) -1H-pyrazol-5-yl]carboxylic acid;
methyl [4-(4-methylphenyl)-3-[4-(methylsulfonyl)phenyl]-1-(2-phenylethyl)-1H-pyrazol-5-yl]carboxylate;
N-phenyl -[4-(4-methylphenyl)-3-[4 -(methylsulfonyl)phenyl]-1-(2-phenylethyl)-1H-pyrazol- 5-yl]carboxamide;
5-(difluoromethyl)-1-ethyl-4-(3-fluoro-4-methoxyphenyl)-3-[4-(methylsulfonyl)phenyl]-1H-pyrazole;
1-ethyl-4-(3-fluoro-4-methoxyphenyl)-3-[4-(methylsulfonyl)phenyl]-5-(pentafluoroethyl)-1H-pyrazole;
6-cyano-1-ethyl-4-(3-fluoro-4-methoxyphenyl)-3-[4 -(methysulfonyl)phenyl]-1H-pyrazole;
1-ethyl-4-(3-fluoro-4-methoxyphenyl)-5-methyl-3-[4-(methylsulfonyl)phenyl]-1H-pyrazole
-ethyl-4-(3-fluoro-4-methoxyphenyl)-3-[4-(methylsulfonyl)phenyl]-5-(hydroxymethyl)-1H-pyrazole;
5-(benzyloxymethyl)-1-ethyl-4-(3-fluoro-4-methoxyphenyl)-3-[4-(methylsulfonyl)phenyl]-1pyrazole;
[1-ethyl-4-(3-fluoro-4-methoxyphenyl)-3-[4-(methylsulfonyl)phenyl1 ]-1H -pyrazol-5-yl]carboxylic acid;
methyl [1-ethyl-4-(3-fluoro-4-methoxyphenyl)-3-[4-(methylsulfonyl)phenyl]-1H-pyrazol-5-yl]carboxylate;
N-phenyl -[1-ethyl-4-(3-fluoro-4-methoxyphenyl)-3-[4 -(methylsulfonyl)phenyl]-1H-pyrazol-5-yl]carboxamide;
1-benzyl-5-(difluoromethyl)-4-(3-fluoro-4 -methoxyphenyl)-3-[4-(methylsulfonyl)phenyl]-1H-pyrazole;
-benzyl-4-(3-fluoro-4-methoxyphenyl)-3-[4-(methylsulfonyl)phenyl]-5-(pentafluoroethyl)-1H-pyrazole;
1-benzyl-5-cyano-4-(3-fluoro-4-methoxyphenyl)-3-[4-(methylsulfonyl)phenyl]-1H-pyrazole;
1-benzyl-4-(3-fluoro-4-methoxyphenyl)-5-methyl-3-[4-(methylsulfonyl)phenyl]-1H-pyrazole;
1-benzyl-4-(3-fluoro-4-methoxyphenyl)-3-[4 -(methylsulfonyl)phenyl]-5-(hydroxymethyl)-1H-pyrazole;
1-benzyl-5-(benzyloxymethyl)-4-(3-fluoro-4-methoxyphenyl)-3-[4-(methylsulfonyl)phenyl]-1H-pyrazole;
[1-benzyl-4-(3-fluoro-4-methoxyphenyl)-3-[4-(methylsulfonyl)phenyl]-1H-pyrazol-5-yl]carboxylic acid;
methyl [1-benzyl-4-(3-fluoro-4-methoxyphenyl)-3-[4-(methylsulfonyl)phenyl]-1H-pyrazol-5-yl]carboxylate;
N-phenyl-[1-benzyl-4-(3-fluoro-4-methoxyphenyl)-3-[4-(methylsulfonyl)phenyl]-1H-pyrazol5-yl]carboxamide;
1-(cyanomethyl)-5-(difluoromethyl)-4-(3-fluoro-4-methoxyphenyl)-3-[4-(methylsulfonyl)phenyl]-1H-pyrazole;

1-ethyl-4-(3-fluoro-4-methoxyphenyl)-3-[4-(methylsulfonyl)phenyl]-5-(pentafluoroethyl)-1H-pyrazole;
5-cyano-1-(cyanomethyl)-4-(3-fluoro-4-methoxyphenyl)-3-[4-(methylsulfonyl)phenyl]-1H-pyrazole;
1-(cyanomethyl)-4-(3-fluoro-4-methoxyphenyl)-5-methyl-3-[4-(methylsulfonyl)phenyl]-1H-pyrazole;
1-(cyanomethyl)-4-(3-fluoro-4-methoxyphenyl)-5-(hydroxymethyl)-3-[4-(methylsulfonyl)phenyl]-1H-pyrazole;
5-(benzylroxymethyl)-1-(cyanomethyl)-4-(3-fluoro-4-methoxyphenyl)-3-[4-(methylsulfonyl)phenyl]-1H-pyrazole;
[1-(cyanomethyl)-4-(3-fluoro-4-methoxyphenyl)-3-[4-(methylsulfonyl)phenyl]-1H-pyrazol-1-5-yl]carboxylic acid;
methyl [1-(cyanomethyl)-4-(3-fluoro-4-methoxyphenyl)-3-[4-(methylsulfonyl)phenyl]-1H-pyrazol-5-yl]carboxylate;
N-phenyl-[1-(cyanomethyl)-4-(3-fluoro- 4-methoxyphenyl)-3-[4-(methylsulfonyl)phenyl]-1H-pyrazol-5-yl]carboxamide;
5-(difluoromethyl)-4-(3-fluoro-4-methoxyphenyl)-3-[4-(methylsulfonyl)phenyl]-1-(3-propenyl)-1H-pyrazole;
4-(3-fluoro-4-methoxyphenyl)-3-[4-(methylsulfonyl)phenyl]-5-(pentafluoroethyl)-1-(3-propenyl)-1H-pyrazole;
5-cyano-4-(3-fluoro-4-methoxyphenyl)-3-[4-(methylsulfonyl)phenyl]-1-(3-propenyl)-1H-pyrazole;
4-(3-fluoro-4-methoxyphenyl)-5-methyl-3-[4-(methylsulfonyl)phenyl]-1-(3-propenyl)-1-H-pyrazole;
4-(3-fluoro-4-methoxyphenyl)-5-(hydroxymethyl)-3-[4-methylsulfonyl)phenyl]-1-(3-propenyl)-1H-pyrazole;
5-(benzyloxymethyl)-4-(3-fluoro-4-methoxyphenyl)-3-[4-(methylsulfonyl)phenyl]-1-(3-propenyl)-1H-pyrazole;
[4-(3-fluoro-4-methoxyphenyl)-3-[4-(methylsulfonyl)phenyl]-1-(3-propenyl)-1H-pyrazol-5-yl]carboxylic acid;
methyl [4-(3-fluoro-4-methoxyphenyl)-3-[4-(methylsulfonyl)phenyl]-1-(3-propenyl)-1H-pyrazol-5-yl]carboxylate;
N-phenyl-[4-(3-fluoro-4-methoxyphenyl)-3-[4-(methylsulfonyl)phenyl]-1-(3-propenyl)-1H-pyrazol-5-yl]carboxamide;
5-(difluoromethyl)-4-(3-fluoro-4-methoxyphenyl)-3-[4-(methylsulfonyl)phenyl]-1-(2-phenylethyl)-1H-pyrazole;
4-(3-fluoro-4-methoxytphenyl)-3-[4-(methylsulfonyl)phenyl]-5-(pentafluoroethyl)-1-(2-phenylethyl)-1H-pyrazole;
5-cyano-4-(3-fluoro-4-methoxyphenyl)-3-[4-(methylsulfonyl)phenyl]-1-(2-phenylethyl)-1H-pyrazole;
4-(3-fluoro-4-methoxyphenyl)-5-methyl-3-[4-(methylsulfonyl)phenyl]-1-(2-phenylethyl)-1H-pyrazole;
4-(3-fluoro-4-methoxyphenyl)-5-(hydroxymethyl)-3-[4-(methylsulfonyl)phenyl]-1-(2-phenylethyl)-1H-pyrazole;
5-(benzyloxymethyl)-4-(3-fluoro-4-methoxyphenyl)-3-[4-(methylsulfonyl)phenyl]-1-(2-phenylethyl)-1H-pyrazole;
[4-(3-fluoro-4-methoxyphenyl)-3-[4-(methylsulfonyl)phenyl]-1-(2-phenylethyl)-1H-pyrazol-5-yl]carboxylic acid;
methyl [4-(3-fluoro-4-methoxyphenyl)-3-[4-(methylsulfonyl)phenyl]-1-(2-phenylethyl)-1H-pyrazol-5-yl]carboxylate; and
N-phenyl-4[-(3-fluoro-4-methoxyphenyl)-3-[4-(methylsulfonyl)phenyl]-1-(2-phenylethyl)-1H-pyrazol-5-yl]carboxamide.

A third preferred class of compounds consists of those compounds of Formula I wherein $R^2$ is aryl substituted at a substitutable position with sulfamyl; or a pharmaceutically-acceptable salt thereof.

A third more preferred class of compounds consists of those compounds of Formula I wherein $R^1$ is selected from hydrido, lower alkyl, lower alkenyl, lower alkynyl, lower haloalkyl, lower aralkyl, lower heterocyclicalkyl, lower heteroaralkyl, lower hydroxyalkyl, lower alkoxyalkyl, lower cyanoalkyl, lower aminoalkyl, lower alkylaminoalkyl, lower carboxyalkyl, lower alkoxycarbonylalkyl, lower alkylaminocarbonylalkyl, lower N-hydroxyaminocarbonylalkyl, lower N-hydroxy-N-alkyl-aminocarbonylalkyl, lower arylaminocarbonylalkyl and lower aminocarbonylalkyl;

wherein $R^2$ is aryl selected from phenyl, naphthyl and biphenyl, wherein the aryl radical is substituted at a substitutable position with sulfamyl;

wherein $R^3$ is selected from aryl, lower cycloalkyl, lower cycloalkenyl and heterocyclo; wherein $R^3$ is optionally substituted at a substitutable position with one or more radicals selected from halo, lower alkylthio, lower alkylsulfinyl, lower alkyl, cyano, carboxyl, lower alkoxycarbonyl, aminocarbonyl, lower alkylaminocarbonyl, lower arylaminocarbonyl, lower N-alkyl-N-arylaminocarbonyl, lower haloalkyl, hydroxyl, lower alkoxy, lower hydroxyalkyl, lower haloalkoxy, amino, lower alkylamino, lower arylamino, heterocyclo and nitro; and wherein $R^4$ is selected from hydrido, lower alkyl, lower haloalkyl, cyano, acyl, lower alkoxy, carboxyl, lower carboxyalkyl, lower alkoxycarbonyl, lower alkoxycarbonylalkyl, lower aralkoxycarbonylalkyl, aminocarbonyl, lower alkylaminocarbonyl, lower arylaminocarbonyl, lower N-alkyl-N-arylaminocarbonyl, lower aminocarbonylalkyl, lower hydroxyalkyl and lower aralkoxyalkyl.

A third class of compounds of particular interest consists of those compounds of Formula I wherein $R^1$ is selected from hydrido, methyl, ethyl, isopropyl, tert-butyl and isobutyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, ethylenyl, propylenyl, butenyl, pentenyl, isopropylenyl, isobutylenyl, propargyl, benzyl, phenylethyl, phenylpropyl, morpholinomethyl, pyrrolidinylmethyl, piperazinylmethyl, piperidinylmethyl, pyridylmethyl, thienylmethyl, hydroxymethyl, hydroxyethyl, methoxymethyl, ethoxymethyl, cyanomethyl, aminomethyl, methylaminomethyl, formyl, acetyl, propanyi, butanyl, methoxycarbonylmethyl, ethoxycarbonylethyl, N-methylaminocarbonylmethyl, N,N-dimethylaminocarbonylmethyl, N-hydroxyaminocarbonylmethyl, N-hydroxy-N-methylaminocarbonylmethyl, N-phenylaminocarbonylmethyl and aminocarbonylmethyl;

wherein $R^3$ is selected from phenyl, naphthyl, biphenyl, cyclohexyl, cyclopentyl, cycloheptyl, 1-cyclohexenyl, 2-cyclohexenyl, 3-cyclohexenyl, 4-cyclohexenyl, 4-methylcyclohex-4-en-1-yl, 1cyclopentenyl, pyridyl, thienyl, thiazolyl, oxazolyl, furyl and pyrazinyl; wherein $R^3$ is optionally substituted at a substitutable position with one or more radicals selected from fluoro, chloro, bromo, methylthio, methylsulfinyl, cyano, methyl, ethyl, isopropyl, tert-butyl, isobutyl, carboxyl, aminocarbonyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, N-methylaminocarbonyl, N-ethylaminocarbonyl, N-isopropylaminocarbonyl, N-propylaminocarbonyl, N-butylaminocarbonyl, N-isobutylaminocarbonyl, N-tert-butylaminocarbonyl, N-pentylaminocarbonyl, N,N-dimethylaminocarbonyl, N-methyl-N-ethylaminocarbonyl, N-phenylaminocarbonyl, N-(3-fluorophenyl)aminocarbonyl, N-(4-methylphenyl)aminocarbonyl, N-(3-chlorophenyl)aminocarbonyl, N-(4-methoxyphenyl)aminocarbonyl, N-methyl-N-phenylaminocarbonyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, methoxy, methylenedioxy, ethoxy, propoxy, n-butoxy, trifluoromethoxy, hydroxymethyl, hydroxyethyl, hydroxypropyl, amino, nitro, methylamino, dimethylamino, phenylamino, morpholino, pyrrolidinyl, piperazinyl and piperidinyl;

wherein $R^4$ is selected from hydrido, methyl, ethyl, isopropyl, tert-butyl, isobutyl, methoxy, ethoxy, propoxy, n-butoxy, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, cyano, formyl, carboxyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, methoxycarbonylalkyl, benzyloxycarbonylmethyl, aminocarbonyl, N-methylaminocarbonyl, N-ethylaminocarbonyl, N-isopropylaminocarbonyl, N-propylaminocarbonyl, N-butylaminocarbonyl, N-isobutylaminocarbonyl, N-tert-butylaminocarbonyl, N-pentylaminocarbonyl, N,N-dimethylaminocarbonyl, N-methyl-N-ethylaminocarbonyl, N-phenylaminocarbonyl, N-(3-fluorophenyl)aminocarbonyl, N-(4-methylphenyl)aminocarbonyl, N-(3-chlorophenyl)aminocarbonyl, N-(4-methoxyphenyl)aminocarbonyl, N-methyl-N-phenylaminocarbonyl, aminocarbonylmethyl, hydroxypropyl, hydroxymethyl, hydroxyethyl, butanyl, acetyl, propanyl and benzyloxymethyl.

Another family of specific compounds of particular interest within Formula I consists of compounds and pharmaceutically-acceptable salts thereof as follows:

4-[4-[4-(4-fluorophenyl)-5-(trifluoromethyl)-1H-pyrazol-3-yl]benzenesulfonamide;
4-[4-(4-chlorophenyl)-5-(trifluoromethyl)-1H-pyrazol-3-yl]benzenesulfonamide;
4-[4-(4-methylphenyl)-5-(trifluoromethyl)-1H-pyrazol-3-yl]benzenesulfonamide;
4-[4-(2,4-dichlorophenyl)-5-(trifluoromethyl)-1H-pyrazol-3-yl]benzenesulfonamide;
4-[[(3,4-dichlorophenyl)-5-(trifluoromethyl)-1H-pyrazol-3-yl]benzenesulfonamide;
4-[4-(4-bromophenyl)-5-(trifluoromethyl)-1H-pyrazol-3-yl]benzenesulfonamide;
4-[4-(3-chlorophenyl)-5-(trifluoromethyl)-1H-pyrazol-3-yl]benzenesulfonamide;
4-[4-(2-chlorophenyl)-5-(trifluoromethyl)-1H-pyrazol-3-yl]benzenesulfonamide;
4-[4-phenyl-5-(trifluoromethyl)-1H-pyrazol-3-yl]benzenesulfonamide;
4-[4-(4-methoxyphenyl)-5-(trifluoromethyl)-1H-pyrazol-3-yl]benzenesulfonamide;
4-[4-(4-trifluoromethoxyphenyl)-5-(trifluoromethyl)-1H-pyrazol-3-yl]benzenesulfonamide;
4-[4-(2-methylphenyl)-5-(trifluoromethyl)-1H-pyrazol-3-yl]benzenesulfonamide;
4-[4-(3-methylphenyl)-5-(trifluoromethyl)-1H-pyrazol-3-yl]benzenesulfonamide;
4-[4-(4-fluoro-2-methylphenyl)-5-(trifluoromethyl)-1H-pyrazol-3-yl]benzenesulfonamide;
4-[4-(3,5-dimethyl-4-methoxyphenyl)-5-(trifluoromethyl)-1H-pyrazol-3-yl]benzenesulfonamide;
4-[4-(4-methoxy-3-methylphenyl)-5-(trifluoromethyl)-1H-pyrazol-3-yl]benzenesulfonamide;
4-[4-(4-fluoro-2-methoxyphenyl)-5-(trifluoromethyl)-1H-pyrazol-3-yl]benzenesulfonamide;
4-[4-(2,4-dimethylphenyl)-5-(trifluoromethyl)-1H-pyrazol-3-yl]benzenesulfonamide;
4-[4-(3,4-dimethylphenyl)-5-(trifluoromethyl)-1H-pyrazol-3-yl]benzenesulfonamide;
4-[4-(2,5-dichlorophenyl)-5-(trifluoromethyl)-1H-pyrazol-3-yl]benzenesulfonamide;
4-[4-(4-ethoxyphenyl)-5-(trifluoromethyl)-1H-pyrazol-3-yl]benzenesulfonamide;
4-[4-(4-n-butoxyphenyl)-5-(trifluoromethyl)-1H-pyrazol-3-yl]benzenesulfonamide;
4-[4-(2-fluorophenyl)-5-(trifluoromethyl)-1H-pyrazol-3-yl]benzenesulfonamide;
4-[4-(3-fluorophenyl)-5-(trifluoromethyl)-1H-pyrazol-3-yl]benzenesulfonamide;
4-[4-(2-pyridyl)-5-(trifluoromethyl)-1H-pyrazol-3-yl]benzenesulfonamide;
4-[4-(3-pyridyl)-5-(trifluoromethyl)-1H-pyrazol-3-yl]benzenesulfonamide;
4-[4-(4-pyridyl)-5-(trifluoromethyl)-1H-pyrazol-3-yl]benzenesulfonamide;
4-[4-(4-aminophenyl)-5-(trifluoromethyl)-1H-pyrazol-3-yl]benzenesulfonamide;
4-[4-(4-acetamidophenyl)-5-(trifluoromethyl)-1H-pyrazol-3-yl]benzenesulfonamide;
4-[4-(4-trifluoroacetamidophenyl)-5-(trifluoromethyl)-1H-pyrazol-3-yl]benzenesulfonamide;
4-[4-(3-fluoro-4-methoxyphenyl)-5-(trifluoromethyl)-1H-pyrazol-3-yl]benzenesulfonamide;
4-[4-(3-fluoro-4-methylphenyl)-5-(trifluoromethyl)-1H-pyrazol-3-yl]benzenesulfonamide;
4-[4-(3,5-dichloro-4-methoxyphenyl)-5-(trifluoromethyl)-1H-pyrazol-3-yl]benzenesulfonamide;
4-[4-(3,5-difluoro-4-methoxyphenyl)-5-(trifluoromethyl)-1H-pyrazol-3-yl]benzenesulfonamide;
4-[4-(4-(methylthio)phenyl)-5-(trifluoromethyl)-1H-pyrazol-3-yl]benzenesulfonamide;
4-[4-(3-chloro-4-(methylthio)phenyl)-5-(trifluoromehyl)-1H-pyrazol-3-yl]benzenesulfonamide;
4-[[3-[4-(aminosulfonyl)phenyl]-5-(trifluoromethyl)-1H-pyrazol-4-yl]benzoic acid;
methyl 4-[3-[4-(aminosulfonyl)phenyl]-5-(trifluoromethyl)-1H-pyrazol-4-yl]benzoate;
4-[[3-[4-(aminosulfonyl)phenyl]-5-(trifluoromethyl)-1H-pyrazol-4-yl]benzamide;
4-[4-(4-fluorophenyl)-1H-pyrazol-3-yl]benzenesulfonamide;
4-[4-(4-chlorophenyl)-1H-pyrazol-3-yl]benzenesulfonamide;
4-[4-(4-methylphenyl)-1H-pyrazol-3-yl]benzenesulfonamide;
4-[4-(2,4-dichlorophenyl)-1H-pyrazol-3-yl]benzenesulfonamide;
4-[4-(3,4-dichlorophenyl)-1H-pyrazol-3-yl]benzenesulfonamide;
4-[4-(4-bromophenyl)-1H-pyrazol-3-yl]benzenesulfonamide;
4-[4-(3-chlorophenyl)-1H-pyrazol-3-yl]benzenesulfonamide;
4-[4-(2-chlorophenyl)-1H-pyrazol-3-yl]benzenesulfonamide;
4-[phenyl-1H-pyrazol-3-yl]benzenesulfonamide;
4-[4-(4-methoxyphenyl)-1H-pyrazol-3-yl]benzenesulfonamide;
4-[4-(4-trifluoromethoxyphenyl)-1H-pyrazol-3-yl]benzenesulfonamide;

4-[4-(2-methylphenyl)-1H-pyrazol-3-yl]benzenesulfonamide;
4-[4-(3-methylphenyl)-1H-pyrazol-3-yl]benzenesulfonamide;
4-[4-(4-fluoro-2-methylphenyl)-1H-pyrazol- 3-yl]benzenesulfonamide;
4-[4-(3,5-dimethyl-4-methoxyphenyl)-1H-pyrazol-3-yl]benzenesulfonamide;
4-[4-(4-methoxy-3-methylphenyl)-1H-pyrazol-3-yl]benzenesulfonamide;
4-[4-(4-fluoro-2-methoxyphenyl)-1H-pyrazol-3-yl]benzenesulfonamide;
4-[4-(2,4-dimethylphenyl)-1H-pyrazol-3-yl]benzenesulfonamide;
4-[4-(3,4-dimethylphenyl)-1H-pyrazol-3-yl]benzenesulfonamide;
4-[4-(2,5-dichlorophenyl)-1H-pyrazol-3-yl]benzenesulfonamide;
4-[4-(4-ethoxyphenyl)-1H-pyrazol-3-yl]benzenesulfonamide;
4-[4-(4-n-butoxyphenyl)-1H-pyrazol-3-yl]benzenesulfonamide;
4-[4-(2-fluorophenyl)-1H-pyrazol-3-yl]benzenesulfonamide;
4-[4-(3-fluorophenyl)-1H-pyrazol-3-yl]benzenesulfonamide;
4-[4-(2-pyridyl)-1H-pyrazol-3-yl]benzenesulfonamide;
4-[4-(3-pyridyl)-1H-pyrazol-3-yl]benzenesulfonamide;
4-[4-(4-pyridyl)-1H-pyrazol-3-yl]benzenesulfonamide;
4-[4-(4-aminophenyl)-1H-pyrazol-3-yl]benzenesulfonamide;
4-[4-(4-acetamidophenyl)-1H-pyrazol-3-yl]benzenesulfonamide;
4-[4-(4-trifluoroacetamidophenyl)-1H-pyrazol-3-yl]benzenesulfonamide;
4-[4-(3-fluoro-4-methoxyphenyl)-1H-pyrazol-3-yl]benzenesulfonamide;
4-[4-(3-fluoro-4-methylphenyl)-1H-pyrazol-3-yl]benzenesulfonamide;
4-[4-(3,5-dichloro-4-methoxyphenyl)-1H-pyrazol-3-yl]benzenesulfonamide;
4-[4-(3,5-difluoro-4-methoxyphenyl)-1H-pyrazol- 3-yl]benzenesulfonamide;
4-[4-(4-(methylthio)phenyl)-1H-pyrazol-3-yl]benzenesulfonamide;
4-[4-(3-chloro-4-(methylthio)phenyl)-1H-pyrazol-3-yl]benzenesulfonamide;
4-[3-[4-(aminosulfonyl)phenyl]-1H-pyrazol-4-yl]benzoic acid;
methyl 4-[3-[4-(aminosulfonyl)phenyl]-1H-pyrazol-4-yl]benzoate;
4-[[3-[4-(aminosulfonyl)phenyl]-1H-pyrazol-4-yl]benzamide;
4-[4-(4-chlorophenyl)-5-(difluoromethyl)-1H-pyrazol-3-yl]benzenesulfonamide;
4-[5-(chlorodifluoromethyl)-4-(4-chlorophenyl)-1H-pyrazol-3-yl]benzenesulfonamide;
4-[4-(4-chlorophenyl)-5-(pentafluoroethyl)-1H-pyrazol-3-yl]benzenesulfonamide;
4-[4-(4-chlorophenyl)-5-cyano-1H-pyrazol-3-yl]benzenesulfonamide;
4-[4-(4-chlorophenyl)-5-methyl-1H-pyrazol-3-yl]benzenesulfonamide;
4-[4-(4-chlorophenyl)-5-ethyl-1H-pyrazol-3-yl]benzenesulfonamide;
4-[4-(4-chlorophenyl)-5-(hydroxymethyl)-1H-pyrazol-3-yl]benzenesulfonamide;
4-[5-(benzyloxymethyl)-4-(4-chlorophenyl)-1H-pyrazol-3-yl]benzenesulfonamide;
[3-[4-(aminosulfonyl)phenyl]-4-(4-chlorophenyl)-1H-pyrazol-5-yl]carboxylic acid;
methyl [3-[4-(aminosulfonyl)phenyl]-4-(4-chlorophenyl)-1H-pyrazol-5-yl]carboxylate;
ethyl [3-[4-(aminosulfonyl)phenyl]-4-(4-chlorophenyl)-1H-pyrazol-5-yl]carboxylate;
tert-butyl [3-[4-(aminosulfonyl)phenyl]-4-(4-chlorophenyl)-1H-pyrazol-5-yl]carboxylate;
benzyl [3-[4-(aminosulfonyl)phenyl]-4-(4-chlorophenyl)-1H-pyrazol-5yl]-carboxylate;
isopropyl [3-[4-(aminosulfonyl)phenyl]-4-(4-chlorophenyl)-1H-pyrazol-5-yl]carboxylate;
[3-[4-(aminosulfonyl)phenyl]-4-(4-chlorophenyl)-1H-pyrazol-5-yl]carboxamide;
N-phenyl-[3-[4-(aminosulfonyl)phenyl]-4-(4-chlorophenyl)-1H-pyrazol-5-yl]carboxamide;
N-methyl-N-phenyl-[3-[4-(aminosulfonyl)phenyl]-4-(4-chlorophenyl)-1H-pyrazol-5-yl]carboxamide;
N,N-dimethyl-[3-[4-(aminosulfonyl)phenyl]-4-(4-chlorophenyl)-1H-pyrazol-5-yl]carboxamide;
N-(3-chlorophenyl)-[3-[4-(aminosulfonyl)phenyl]-4-(4-chlorophenyl)-1H-pyrazol-5-yl]carboxamide;
4-[4-(4-methylphenyl)-5-(difluoromethyl)-1H-pyrazol-3-yl]benzenesulfonamide;
4-[4-(4-methylphenyl)-5-(chlorodifluoromethyl)-1H-pyrazol-3-yl]benzenesulfonamide;
4-[4-(4-methylphenyl)-5-(pentafluoroethyl)-1H-pyrazol3-yl]benzenesulfonamide;
4-[3-[4-(aminosulfonyl)phenyl]-4-(4-methylphenyl)-1H-pyrazol-5-yl]carboxylic acid;
methyl [3-[4-(aminosulfonyl)phenyl]-4-(4-methylphenyl)-1H-pyrazol-5-yl]carboxylate;
[3-[4-(aminosulfonyl)phenyl]-4-(4-methylphenyl)-1H-pyrazol-5-yl]carboxamide;
N-phenyl-[3-[4-(aminosulfonyl)phenyl]-4-(4-methylphenyl)-1H-pyrazol-5-yl]carboxamide;
4-[4-(4-fluorophenyl)-1-methyl-5-(trifluoromethyl)-1H-pyrazol-3-yl]benzenesulfonamide;
4-[1-ethyl-4-(4-fluorophenyl)-5-(trifluoromethyl)-1H-pyrazol-3-yl]benzenesulfonamide;
4-[1-benzyl-4-(4-fluorophenyl)-5-(trifluoromethyl)-1H-pyrazol-3-yl]benzenesulfonamide;
4-[4-(4-fluorophenyl)-1-(3-propenyl)-5-(trifluoromethyl)-1H-pyrazol-3-yl]benzenesulfonamide;
4-[4-(4-fluorophenyl)-1-(3-propynyl)-5-(trifluoromethyl)-1H-pyrazol- 3-yl]benzenesulfonamide;
4-[1-cyanomethyl-4-(4-fluorophenyl)-5-(trifluoromethyl)-1H-pyrazol-3-yl]benzenesulfonamide;
4-[4-(4-fluorophenyl)-1-[2-(1H-pyrrolidin-1-yl)ethyl]-5-(trifluoromethyl)-1H-pyrazol-3-yl]benzenesulfonamide;
ethyl [3-[4-(aminosulfonyl)phenyl]-4-(4-fluorophenyl)-5-(trifluoromethyl)-1H-pyrazol-1-yl]acetate;
N-phenyl-[3-[4-(aminosulfonyl)phenyl]-4-(4-fluorophenyl)-5-(trifluoromethyl)-1H-pyrazol-1-yl]acetamide;
[3-[4-(aminosulfonyl)phenyl]-4-(4-fluorophenyl)-5-(trifluoromethyl)-1H-pyrazol-1-yl]acetic acid;
[3-[4-(aminosulfonyl)phenyl]-4-(4-fluorophenyl)-5-(trifluoromethyl)-1H-pyrazol-1-yl]acetamide;
4-[4-(4-fluorophenyl) -1-(3-hydroxypropyl)-(trifluoromethyl)-1H-pyrazol-3-yl]benzenesulfonamide;
4-[4-(4-fluorophenyl)-1-[2-(2-pyridyl)ethyl]-5-(trifluoromethyl)-1H-pyrazol-3-yl]benzenesulfonamide;
4-[4-(4-fluorophenyl)-1-(2-phenylethyl)-5(trifluoromethyl)-1H-pyrazol-3-yl]benzenesulfonamide;
N-hydroxy-N-methyl-[3-[4-(aminosulfonyl)phenyl]-4-(4-fluorophenyl)-5-(trifluoromethyl)-1H-pyrazol-1-yl]acetamide;

4-[1-[2-(dimethylamino)ethyl]-4-(4-fluorophenyl)-5-(trifluoromethyl)-1H-pyrazol-3-yl]benzenesulfonamide;
4-[1-methyl-4-(4-methylphenyl)-5-(trifluoromethyl)-1H-pyrazol-3-yl]benzenesulfonamide;
4-[1-ethyl-4-(4-methylphenyl)-5-(trifluoromethyl)-1H-pyrazol-3-yl]benzenesulfonamide;
4-[1-benzyl-4-(4-methylphenyl)-5-(trifluoromethyl)-1H-pyrazol-3-yl]benzenesulfonamide;
4-[4-(4-methylphenyl)-1-(3-propenyl)-5-(trifluoromethyl)-1H-pyrazol-3-yl]benzenesulfonamide;
4-[4-(4-methylphenyl)-1-(3-propynyl)-5-(trifluoromethyl)-1H-pyrazol-3-yl]benzenesulfonamide;
4-[1-cyanomethyl-4-(4-methylphenyl)-5-(trifluoromethyl)-1H-pyrazol-3-yl]benzenesulfonamide;
ethyl [3-[4-(aminosulfonyl)phenyl]-4-(4-methylphenyl)-5-(trifluoromethyl)-1H-pyrazol-1-yl]acetate;
[3-[4-(aminosulfonyl)phenyl]-4-(4-methylphenyl)-5-(trifluoromethyl)-1H-pyrazol-1-yl]acetic acid;
4-[1-(3-hydroxypropyl)-4-(4-methylphenyl)-5-(trifluoromethyl)-1H-pyrazol-3-yl]benzenesulfonamide;
4-[1-[2-(dimethylamino)ethyl]-4-(4-methylphenyl)-5-(trifluoromethyl)-1H-pyrazol-3-yl]benzenesulfonamide;
4-[4-(4-chlorophenyl)-1-methyl-5-(trifluoromethyl)-1H-pyrazol-3-yl]benzenesulfonamide;
4-[4-(4-chlorophenyl)-1-ethyl-5-(trifluoromethyl)-1H-pyrazol-3-yl]benzenesulfonamide;
4-[1-benzyl-4-(4-chlorophenyl)-5-(trifluoromethyl)-1H-pyrazol-3-yl]benzenesulfonamide;
4-[4-(4-chlorophenyl)-1-(3-propenyl)-5-(trifluoromethyl)-1H-pyrazol-3-yl]benzenesulfonamide;
4-[4-(4-chlorophenyl)-1-(3-propynyl)-5-(trifluoromethyl)-1H-pyrazol-3-yl]benzenesulfonamide;
4-[4-(4-chlorophenyl)-1-cyanomethyl-5-(trifluoromethyl)-1H-pyrazol-3-yl]benzenesulfonamide;
ethyl [3-[4-(aminosulfonyl)phenyl]-4-(4-chlorophenyl)5-(trifluoromethyl)-1H-pyrazol-1-yl]acetate;
[3-[4-(aminosulfonyl)phenyl]-4-(4-chlorophenyl)-5-(trifluoromethyl)-1H-pyrazol-1-yl]acetic acid;
4-[4-(4-chlorophenyl)-1-(3-hydroxypropyl)-5-(trifluoromethyl)-1H-pyrazol-3-yl]benzenesulfonamide;
4-[4-(4-chlorophenyl)-1-[2-(dimethylamino)ethyl]-5-(trifluoromethyl)-1H-pyrazol-3-yl]benzenesulfonamide;
4-[1-methyl-4-phenyl-5-(trifluoromethyl)-1H-pyrazol-3-yl]benzenesulfonamide;
4-[1-ethyl-4-phenyl-5-(trifluoromethyl)-1H-pyrazol-3-yl]benzenesulfonamide;
4-[1-benzyl-4-phenyl-5-(trifluoromethyl)-1H-pyrazol-3-yl]benzenesulfonamide;
4-[phenyl-1-(3-propenyl)-5-(trifluoromethyl)-1H-pyrazol-3-yl]benzenesulfonamide;
4-[phenyl-1-(3-propynyl)-5-(trifluoromethyl)-1H-pyrazol-3-yl]benzenesulfonamide;
4-[1-cyanomethyl-4-phenyl-5-(trifluoromethyl)-1H-pyrazol-3-yl]benzenesulfonamide;
ethyl [3-[4-(aminosulfonyl)phenyl]-4-phenyl-5-(trifluoromethyl)-1H-pyrazol-1-yl]acetate;
[3-[4-(aminosulfonyl)phenyl]-4-phenyl-5-(trifluoromethyl)-1H-pyrazol-1-yl]acetic acid;
4-[1-(3-hydroxypropyl)-4-phenyl-5-(trifluoromethyl)1H-pyrazol-3-yl]benzenesulfonamide;
4-[1-[2-(dimethylamino)ethyl]-4-phenyl-5-(trifluoromethyl)-1H-pyrazol-3-yl]benzenesulfonamide;
4-[4-(4-methoxyphenyl)-1-methyl-5-(trifluoromethyl)1H-pyrazol-3-yl]benzenesulfonamide;
4-[1-ethyl-4-(4-methoxyphenyl)-5-(trifluoromethyl)-1H-pyrazol-3-yl]benzenesulfonamide;
4-[1-benzyl-4-(4-methoxyphenyl)-5-(trifluoromethyl)1H-pyrazol-3-yl]benzenesulfonamide;
4-[4-(4-methoxyphenyl)-1-(3-propenyl)-5-(trifluoromethyl)-1H-pyrazol-3-yl]benzenesulfonamide;
4-[4-(4-methoxyphenyl)-1-(3-propynyl)-5-(trifluoromethyl)-1H-pyrazol-3-yl]benzenesulfonamide;
4-[1-cyanomethyl-4-(4-methoxyphenyl)-5-(trifluoromethyl)-1H -pyrazol-3-yl]benzenesulfonamide;
ethyl [3-[4-(aminosulfonyl)phenyl]-4-(4-methoxyphenyl)-5-(trifluoromethyl)-1H-pyrazol-1-yl]acetate;
[3-[4-(aminosulfonyl)phenyl]-4-(4-methoxyphenyl)-5-(trifluoromethyl)-1H-pyrazol-1-yl]acetic acid;
4-[1-(3-hydroxypropyl)-4-(4-methoxyphenyl)-5-(trifluoromethyl)-1H-pyrazol-3-yl]benzenesulfonamide;
4-[1-[2-(dimethylamino)ethyl]-4-(4-methoxyphenyl)-5-(trifluoromethyl)-1H-pyrazol-3-yl]benzenesulfonamide;
-[4-(2,4-dichlorophenyl)-1-methyl-5-(trifluoromethyl)-1H-pyrazol-3-yl]benzenesulfonamide;
4-[4-(2,4-dichlorophenyl)-1-ethyl-5-(trifluoromethyl)-1H-pyrazol-3-yl]benzenesulfonamide;
4-[1-benzyl-4-(2,4-dichlorophenyl)-5-(trifluoromethyl)-1H-pyrazol-3-yl]benzenesulfonamide;
4-[4-(2,4-dichlorotphenyl)-1-(3-propenyl)-5-(trifluoromethyl)-1H-pyrazol-3-yl]benzenesulfonamide;
4-[4-(2,4-dichlorophenyl)-1-(3-propynyl)-5-(trifluoromethyl)-1H -pyrazol-3-yl]benzenesulfonamide;
4-[1-cyanomethyl-4-(2,4-dichlorophenyl)-5-(trifluoromethyl)-1H -pyrazol-3-yl]benzenesulfonamide;
ethyl [3-[4-(aminosulfonyl)phenyl]-4-(2,4-dichlorophenyl)-5-(trifluoromethyl)-1H-pyrazol-1-yl]acetate;
[3-[4-(aminosulfonyl)phenyl]-4-(2,4-dichlorophenyl)-5-(trifluoromethyl)-1H-pyrazol-1-yl]acetic acid;
4-[4-(2,4-dichlorophenyl)-1-(3-hydroxypropyl)-5-(trifluoromethyl)-1H-pyrazol-3-yl]benzenesulfonamide;
4-[4-(2,4-dichlorophenyl)-1-[2-(dimethylamino)ethyl]-5-(trifluoromethyl)-1H-pyrazol-3-yl]benzenesulfonamide;
4-[1-methyl-4-(2-methylphenyl)-5-(trifluoromethyl)-1H-pyrazol-3-yl]benzenesulfonamide;
4-[1-ethyl-4-(2-methylphenyl)-5-(trifluoromethyl)-1H-pyrazol-3-yl]benzenesulfonamide;
4-[1-benzyl-4-(2-methyltphenyl)-5-(trifluoromethyl)-1H-pyrazol-3-yl]benzenesulfonamide;
4-[4-(2-methylphenyl)-1-(3-propenyl)-5-(trifluoromethyl)-1H-pyrazol-3-yl]benzenesulfonamide;
4-[4-(2-methylphenyl)-1-(3-propynyl)-5-(trifluoromethyl)-1H-pyrazol-3-yl]benzenesulfonamide;
4-[1-cyanomethyl-4-(2-methylphenyl)-5-(trifluoromethyl)-1H-pyrazol-3-yl]benzenesulfonamide;
ethyl [3-[4-(aminosulfonyl)phenyl]-4-(2-methylphenyl)-5-(trifluoromethyl)-1H-pyrazol-1-yl]acetate;
[3-[4-(aminosulfonyl)phenyl]-4-(2-methylphenyl)-5-(trifluoromethyl)-1H-pyrazol-1-yl]acetic acid;
4-[1-(3-hydroxypropyl)-4-(2-methylphenyl)-5-(trifluoromethyl)-1H-pyrazol-3-yl]benzenesulfonamide;
4-[1-[2-(dimethylamino)ethyl]-4-(2-methylphenyl)-5-(trifluoromethyl)-1H-pyrazol-3-yl]benzenesulfonamide;
4-[4-(4-methoxy-3-methylphenyl)-1-methyl-5-(trifluoromethyl)-1H -pyrazol-3-yl]benzenesulfonamide;
4-[1-ethyl-4-(4-methoxy-3-methylphenyl)- 5-(trifluoromethyl)-1H-pyrazol-3-yl]benzenesulfonamide;
4-[1-benzyl-4-(4-methoxy-3-methylphenyl)-5-(trifluoromethyl)-1H-pyrazol-3-yl]benzenesulfonamide;
4-[4-(4-methoxy-3-methylphenyl)-1-(3-propenyl)-5-(trifluoromethyl)-1H -pyrazol-3-yl]benzenesulfonamide;
4-[4-(4-methoxy-3-methylphenyl)-1-(3-propynyl)-5-(trifluoromethyl)-1H-pyrazol-3-yl]benzenesulfonamide;
4-[1-cyanomethyl-4-(4-methoxy-3-methylphenyl)-35-(trifluoromethyl)-1H-pyrazol-3-yl]benzenesulfonamide;
ethyl [3-[4-(aminosulfonyl)phenyl]-4-(4-methoxy-3methylphenyl)-5-(trifluoromethyl)-1H-pyrazol-1-yl]acetate;

[3-[4-(aminosulfonyl)phenyl]-4-(4-methoxy-3-methylphenyl)-5-(trifluoromethyl)-1H-pyrazol-1-yl]acetic acid;

4-[1-(3-hydroxypropyl)-4-(4-methoxy-3-methylphenyl)5-(trifluoromethyl)-1H-pyrazol-3-yl]benzenesulfonamide;

4-[1-[2-(dimethylamino)ethyl]-4-(4-methoxy-3-methylphenyl)-5-(trifluoromethyl)-1H-pyrazol-3-yl]benzene sulfonamide;

4-[4-(3-fluoro-4-methoxyphenyl)-1-methyl-5-(trifluoromethyl)-1H-pyrazol-3-yl]benzenesulfonamide;

4-[1-ethyl-4-(3-fluoro-4-methoxyphenyl)-5-(trifluoromethyl)-1H-pyrazol-3-yl]benzenesulfonamide;

4-[1-benzyl-4-(3-fluoro-4-methoxyphenyl)-5-(trifluoromethyl)-1H-pyrazol-3-yl]benzenesulfonamide;

4-[4-(3-fluoro-4-methoxyphenyl)-1-(3-propenyl)-5-(trifluoromethyl)-1H-pyrazol- 3-yl]benzenesulfonamide;

4-[4-(3-fluoro-4-methoxyphenyl)-1-(3-propynyl)-5-(trifluoromethyl)-1H-pyrazol-3-yl]benzenesulfonamide;

4-[1-cyanomethyl-4-(3-fluoro-4-methoxyphenyl)-5-(trifluoromethyl)-1H-pyrazol-3-yl]benzenesulfonamide;

ethyl [3-[4-(aminosulfonyl)phenyl]-4-(3-fluoro-4methoxyphenyl)-5-(trifluoromethyl)-1H-pyrazol-1-yl]acetate;

[3-[4-(aminosulfonyl)phenyl]-4-(3-fluoro-4-methoxyphenyl)-5-(trifluoromethyl)-1H-pyrazol-1-yl]acetic acid;

4-[4-(3-fluoro-4-methoxyphenyl)-1-(3-hydroxypropyl)5-(trifluoromethyl)-1H-pyrazol-3-yl]benzenesulfonamide;

4-[1-[2-(dimethylamino)ethyl]-4-(3-fluoro-4methoxyphenyl)-5-(trifluoromethyl)-1H-pyrazol-3-yl]benzenesulfonamide;

4-[4-(3-fluoro-4-methylphenyl)-1-methyl-5-(trifluoromethyl)-1H-pyrazol-3-yl]benzenesulfonamide;

4-[1-ethyl-4-(3-fluoro-4-methylphenyl)-5-(trifluoromethyl)-1H-pyrazol-3-yl]benzenesulfonamide;

4-[1-benzyl-4-(3-fluoro-4-methylphenyl)-5-(trifluoromethyl)-1H-pyrazol-3-yl]benzenesulfonamide;

4-[4-(3-fluoro-4-methylphenyl)-1-(3-propenyl)-5-(trifluoromethyl)-1H-pyrazol-3-yl]benzenesulfonamide;

4-[4-(3-fluoro-4-methylphenyl)-1-(3-propynyl)-5-(trifluoromethyl)-1H-pyrazol-3-yl]benzenesulfonamide;

4-[1-cyanomethyl-4-(3-fluoro-4-methylphenyl)-5-(trifluoromethyl)-1H-pyrazol-3-yl]benzenesulfonamide;

ethyl [3-[4-(aminosulfonyl)phenyl]-4-(3-fluoro-4methylphenyl)-5-(trifluoromethyl)-1H-pyrazol-1-yl]acetate;

[3-[4-(aminosulfonyl)phenyl]-4-(3-fluoro-4methylphenyl)-5-(trifluoromethyl)-1H-pyrazol-1-yl]acetic acid;

4-[4-(3-fluoro-4-methylphenyl)-1-(3-hydroxypropyl)-(trifluoromethyl)-1H-pyrazol-3-yl]benzenesulfonamide;

4-[1-[2-(dimethylamino)ethyl]-4-(3-fluoro-4methylphenyl)-5-(trifluoromethyl)-1H-pyrazol-3-yl]benzenesulfonamide;

4-[1-methyl-4-(4-(methylthio)phenyl)-5-(trifluoromethyl)-1H-pyrazol-3-yl]benzenesulfonamide;

4-[1-ethyl-4-(4-(methylthio)phenyl)-5-(trifluoromethyl)-1H-pyrazol-3-yl]benzenesulfonamide;

4-[1-benzyl-4-(4-(methylthio)phenyl)-5-(trifluoromethyl)-1H-pyrazol-3-yl]benzenesulfonamide;

4-[4-(4-(methylthio)phenyl)-1-(3-propenyl)-5-(trifluoromethyl)-1H-pyrazol-3-yl]benzenesulfonamide;

4-[4-(4-(methylthio)phenyl)-1-(3-propynyl)-5-(trifluoromethyl)-1H-pyrazol-3-yl]benzenesulfonamide;

4-[1-cyanomethyl-4-(4-(methylthio)phenyl)-5-(trifluoromethyl)-1H-pyrazol-3-yl]benzenesulfonamide;

ethyl [3-[4-(aminosulfonyl)phenyl]-4-(4-(methylthio)phenyl)-5-(trifluoromethyl)-1H-pyrazol-1-yl]acetate;

[3-[4-(aminosulfonyl)phenyl]-4-(4-(methylthio)phenyl)-5-(trifluoromethyl)-1H-pyrazol-1-yl]acetic acid;

4-[1-(3-hydroxypropyl)-4-(4-(methylthio)phenyl)-5-(trifluoromethyl)-1 H-pyrazol-3 -yl]benzenesulfonamide;

4-[1-[2-(dimethylamino)ethyl]-4-(4(methylthio)phenyl)-5-(trifluoromethyl)-1H-pyrazol-3-yl]benzenesulfonamide;

4-[4-(1-cyclohexenyl)-1-ethyl-5-(trifluoromethyl)-1H-pyrazol-3-yl]benzenesulfonamide;

4-[4-(4-cyanophenyl)-1-ethyl-5-(trifluoromethyl)-1H-pyrazol-3-yl]benzenesulfonamide;

4-[1-ethyl-4-(2-pyrazinyl)-5-(trifluoromethyl)-1H-pyrazol-3-yl]benzenesulfonamide;

4-[4-(5-chloro-2-thienyl)-1-ethyl-5-(trifluoromethyl)-1H-pyrazol-3-yl]benzenesulfonamide;

4-[1-ethyl-4-(4-(morpholino)phenyl)-5-(trifluoromethyl)-1H-pyrazol-3-yl]benzenesulfonamide;

4-[cyclohexyl-1-ethyl-5-(trifluoromethyl)-1H-pyrazol-3-yl]benzenesulfonamide;

4-[1-ethyl-4-(2-thienyl)-5-(trifluoromethyl)-1H-pyrazol-3-yl]benzenesulfonamide;

4-[4-(4-fluorophenyl)-1-methyl-1H-pyrazol-3-yl]benzenesulfonamide;

4-[1-ethyl-4-(4-fluorophenyl)-1H-pyrazol-3-yl]benzenesulfonamide;

4-[1-benzyl-4-(4-fluorophenyl)-1H-pyrazol-3-yl]benzenesulfonamide;

4-[4-(4-fluorophenyl)-1-(3-propenyl)-1H-pyrazol-3-yl]benzenesulfonamide;

4-[4-(4-fluorophenyl)-1-(3-propynyl)-1H-pyrazol-3-yl]benzenesulfonamide

4-[1-cyanomethyl-4-(4-fluorophenyl)-1H-pyrazol-3-yl]benzenesulfonamide

4-[4-(4-fluorophenyl)-1-[2-(1H-pyrrolidin-1-yl) ethyl]-1H-pyrazol-3-yl]benzenesulfonamide;

ethyl [3-[4-(aminosulfonyl)phenyl]-4-(4-fluorophenyl)-1H-pyrazol-1-yl]acetate;

N-phenyl-[3-[4-(aminosulfonyl)phenyl]-4-( 4-fluorophenyl)-1H-pyrazol-1-yl]acetamide;

[3-[4-(aminosulfonyl)phenyl]-4-(4-fluorophenyl)-1H-pyrazol-1-yl]acetic acid;

[3-[4-(aminosulfonyl)phenyl]-4-(4-fluorophenyl)-1H-pyrazol-1-yl]acetamide;

4-[4-(4-fluorophenyl)-1-(3-hydroxypropyl)-1H-pyrazol-3-yl]benzenesulfonamide;

4-[4-(4-fluorophenyl)-1-[2-(2-pyridyl)ethyl]-1H -pyrazol-3-yl]benzenesulfonamide;

4-[4-(4-fluorophenyl)-1-(2-phenylethyl)-1H-pyrazol-3-yl] benzenesulfonamide;

N-hydroxy-N-methyl[3-[4-(aminosulfonyl)phenyl]-4-(4-fluorophenyl)-1H-pyrazol-1-yl]acetamide;

4-[1-[2-(dimethylamino)ethyl]-4-(4-fluorophenyl)-1H-pyrazol-3-yl]benzenesulfonamide;

4-[1-methyl-4-(4-methylphenyl)-1H-pyrazol-3-yl]benzenesulfonamide;

4-[1-ethyl-4-(4-methylphenyl)-1H-pyrazol-3-yl]benzenesulfonamide;

4-[1-benzyl-4-(4-methylphenyl)-1H-pyrazol-3-yl]benzenesulfonamide;

4-[4-(4-methylphenyl)-1-(3-propenyl)-1H-pyrazol-3-yl] benzenesulfonamide;

4-[4-(4-methylphenyl)-1-(3-propynyl)-1H-pyrazol-3-yl] benzenesulfonamide;

4-[1-cyanomethyl-4-(4-methylphenyl)-1H-pyrazol-3-yl] benzenesulfonamide;

ethyl [3-[4-(aminosulfonyl)phenyl]-4-(4-methylphenyl)-1H-pyrazol-1-yl]acetate;

[3-[4-(aminosulfonyl)phenyl]-4-(4-methylphenyl)-1H-pyrazol-1-yl]acetic acid;

4-[1-(3-hydroxypropyl)-4-(4-methylphenyl)-1H-pyrazol-3-yl]benzenesulfonamide;

4-[1-[2-(dimethylamino)ethyl]-4-(4-methylphenyl)-1H-pyrazol-3-yl]benzenesulfonamide;

4-[1-[2-(dimethylamino)ethyl]-4-(4(methylthio)phenyl)-5-(trifluoromethyl)-1H-pyrazol-3-yl]benzenesulfonamide;

4-[4-(4-chlorophenyl)-1-methyl-1H-pyrazol-3-yl]benzenesulfonamide;
4-[4-(4-chlorophenyl)-1-ethyl-1H-pyrazol-3-yl]benzenesulfonamide;
4-[1-benzyl-4-(4-chlorophenyl)-1H-pyrazol-3-yl]benzenesulfonamide;
4-[4-(4-chlorophenyl)-1-(3-propenyl)-1H-pyrazol-3-yl]benzenesulfonamide;
4-[4-(4-chlorophenyl)-1-(3-propynyl)-1H-pyrazol-3-yl]benzenesulfonamide;
4-[4-(4-chlorophenyl)-1-cyanomethyl-1H-pyrazol-3-yl]benzenesulfonamide;
ethyl [3-[4-(aminosulfonyl)phenyl]-4-(4-chlorophenyl)-1H-pyrazol-1-yl]acetate;
[3-[4-(aminosulfonyl)phenyl]-4-(4-chlorophenyl)-1H-pyrazol-1-yl]acetic acid;
4-[4-(4-chlorophenyl)-1-(3-hydroxypropyl)-1H-pyrazol3-yl]benzenesulfonamide;
4-[4-(4-chlorophenyl)-1-[2-(dimethylamino)ethyl]-1H-pyrazol-3-yl]benzenesulfonamide;
4-[1-methyl-4-phenyl-1H-pyrazol-3-yl]benzenesulfonamide;
4-[1-ethyl-4-phenyl-1H-pyrazol-3-yl]benzenesulfonamide;
4-[1-benzyl-4-phenyl-1H-pyrazol-3-yl]benzenesulfonamide;
4-[phenyl-1-(3-propenyl)-1H-pyrazol-3-yl]benzenesulfonamide;
4-[phenyl-1-(3-propynyl)-1H-pyrazol-3-yl]benzenesulfonamide;
4-[1-cyanomethyl-4-phenyl-1H-pyrazol-3-yl]benzenesulfonamide;
ethyl [3-[4-(aminosulfonyl)phenyl]-4-phenyl-1H-pyrazol-1-yl]acetate;
[3-[4-(aminosulfonyl)phenyl]-4-phenyl-1H-pyrazol-1-yl]acetic acid;
4-[1-(3-hydroxypropyl)-4-phenyl-1H-pyrazol-3-yl]benzenesulfonamide;
4-[1-[2-(dimethylamino)ethyl]-4-phenyl-1H-pyrazol-3-yl]benzenesulfonamide;
4-[4-(4-methoxyphenyl)-1-methyl-1H-pyrazol-3-yl]benzenesulfonamide;
4-[1-ethyl-4-(4-methoxyphenyl)-1H-pyrazol-3-yl]benzenesulfonamide;
4-[1-benzyl-4-(4-methoxyphenyl)-1H-pyrazol-3-yl]benzenesulfonamide;
4-[4-(4-methoxyphenyl)-1-(3-propenyl)-1H-pyrazol-3-yl]benzenesulfonamide;
4-[4-(4-methoxyphenyl)-1-(3-propynyl)-1H-pyrazol-3-yl]benzenesulfonamide;
4-[1-cyanomethyl-4-(4-methoxyphenyl)-1H-pyrazol-3-yl]benzenesulfonamide;
ethyl [3-[4-(aminosulfonyl)phenyl]-4-(4-methoxyphenyl)-1H-pyrazol-1-yl]acetate;
[3-[4-(aminosulfonyl)phenyl]-4-(4-methoxyphenyl)-1H-pyrazol-1-yl]acetic acid;
4-[1-(3-hydroxypropyl)-4-(4-methoxyphenyl)-1H-pyrazol-3-yl]benzenesulfonamide;
4-[1-[2-(dimethylamino)ethyl]-4-(4-methoxyphenyl)-1H-pyrazol-3-yl]benzenesulfonamide;
4-[4-(3-fluoro-4-methoxyphenyl)-1-methyl-1H-pyrazol-3-yl]benzenesulfonamide;
4-[1-ethyl-4-(3-fluoro-4-methoxyphenyl)-1H-pyrazol-3-yl]benzenesulfonamide;
4-[1-benzyl-4-(3-fluoro-4-methoxyphenyl)-1H-pyrazol-3-yl]benzenesulfonamide;
4-[4-(3-fluoro-4-methoxyphenyl)-1-(3-propenyl)-1H-pyrazol-3-yl]benzenesulfonamide;
4-[4-(3-fluoro-4-methoxyphenyl)-1-(3-propynyl)-1H-pyrazol-3-yl]benzenesulfonamide;
4-[1-cyanomethyl-4-(3-fluoro-4-methoxyphenyl)-1H-pyrazol-3-yl]benzenesulfonamide;
ethyl [3-[4-(aminosulfonyl)phenyl]-4-(3-fluoro-4-methoxyphenyl)-1H-pyrazol-1-yl]acetate;
[3-[4-(aminosulfonyl)phenyl]-4-(3-fluoro-4-methoxyphenyl)-1H-pyrazol-1-yl]acetic acid;
4-[4-(3-fluoro-4-methoxyphenyl)-1-(3-hydroxypropyl)-1H-pyrazol-3-yl]benzenesulfonamide;
4-[1-[2-(dimethylamino)ethyl]-4-(3-fluoro-4-methoxyphenyl)-1H-pyrazol-3-yl]benzenesulfonamide;
4-[4-(3-fluoro-4-methylphenyl)-1-methyl-1H-pyrazol-3-yl]benzenesulfonamide;
4-[1-ethyl-4-(3-fluoro-4-methylphenyl)-1H-pyrazol-3-yl]benzenesulfonamide;
4-[1-benzyl-4-(3-fluoro-4-methylphenyl)-1H-pyrazol-3-yl]benzenesulfonamide;
4-[4-(3-fluoro-4-methylphenyl)-1-(3-propenyl)-1H-pyrazol-3-yl]benzenesulfonamide;
4-[4-(3-fluoro-4-methylphenyl)-1-(3-propynyl)-1H-pyrazol-3-yl]benzenesulfonamide;
4-[1-cyanomethyl-4-(3-fluoro-4-methylphenyl)-1H-pyrazol-3-yl]benzenesulfonamide;
ethyl [3-[4-(aminosulfonyl)phenyl]-4-(3-fluoro-4-methylphenyl)-1H-pyrazol-1-yl]acetate;
[3-[4-(aminosulfonyl)phenyl]-4-(3-fluoro-4-methoxyphenyl)-1H-pyrazol-1-yl]acetic acid;
4-[4-(3-fluoro-4-methylphenyl)-1-(3-hydroxypropyl)-1H-pyrazol-3-yl]benzenesulfonamide;
4-[1-[2-(dimethylamino)ethyl]-4-(3-fluoro-4-methylphenyl)-1H-pyrazol-3-yl]benzenesulfonamide;
4-[4-(4-chlorophenyl)-5-(difluoromethyl)-1-ethyl-1H-pyrazol-3-yl]benzenesulfonamide;
4-[4-(4-chlorophenyl)-1-ethyl-5-(pentafluoroethyl)-1H-pyrazol-3-yl]benzenesulfonamide;
4-[4-(4-chlorophenyl)-5-cyano-1-ethyl-1H-pyrazol-3yl]benzenesulfonamide;
4-[4-(4-chlorophenyl)-1-ethyl-5-methyl-1H-pyrazol-3yl]benzenesulfonamide;
4-[4-(4-chlorophenyl)-1-ethyl-5-(hydroxymethyl)-1H-pyrazol-3-yl]benzenesulfonamide;
4-[5-(benzyloxymethyl)-4-(4-chlorophenyl)-1-ethyl-1H-pyrazol-3-yl]benzenesulfonamide;
[3-[4-(aminosulfonyl)phenyl]-4-(4-chlorophenyl)-1-ethyl-1H-pyrazol-5-yl]carboxylic acid;
methyl [3-[4-(aminosulfonyl)phenyl]-4-(4-chlorophenyl)-1-ethyl-1H-pyrazol-5-yl]carboxylate;
N-phenyl-[3-[4-(aminosulfonyl)phenyl]-4-(4-chlorophenyl)-1-ethyl-1H-pyrazol-5-yl]carboxamide;
4-[1-benzyl-4-(4-chlorophenyl)-5-(difluoromethyl)-1H-pyrazol-3-yl]benzenesulfonamide;
4-[1-benzyl-4-(4-chlorophenyl)-5-(pentafluoroethyl)-1H-pyrazol-3-yl]benzenesulfonamide;
4-[1-benzyl-4-(4-chlorophenyl)-5-cyano-1H-pyrazol-3-yl]benzenesulfonamide;
4-[1-benzyl-4-(4-chlorophenyl)-5-methyl-1H-pyrazol-3-yl]benzenesulfonamide;
4-[1-benzyl-4-(4-chlorophenyl)-5-(hydroxymethyl)-1H-pyrazol-3-yl]benzenesulfonamide;
4-[1-benzyl-5-(benzyloxymethyl)-4-(4-chlorophenyl)-1H-pyrazol-3-yl]benzenesulfonamide;
[3-[4-(aminosulfonyl)phenyl]-1-benzyl-4-(4chlorophenyl)-1H-pyrazol-5-yl]carboxylic acid;
methyl [3-[4-(aminosulfonyl)phenyl]-1-benzyl-4-(4chlorophenyl)-1H-pyrazol-5-yl]carboxylate;
N-phenyl-[3-[4-(aminosulfonyl)phenyl]-1-benzyl-4-(4chlorophenyl)-1H-pyrazol-5-yl]carboxamide;

4-[4-(4-chlorophenyl)-1-(cyanomethyl)-5(difluoromethyl)-1H-pyrazol-3yl]benzenesulfonamide;

4-[4-(4-chlorophenyl)-1-ethyl-5-(pentafluoroethyl)-1H-pyrazol-3-yl]benzenesulfonamide;

4-[4-(4-chlorophenyl)-5-cyano-1-(cyanomethyl)-1H-pyrazol-3-yl]benzenesulfonamide;

4-[4-(4-chlorophenyl)-1-(cyanomethyl)-5-methyl-1H-pyrazol-3-yl]benzenesulfonamide;

4-[4-(4-chlorophenyl)-1-(cyanomethyl)-5-(hydroxymethyl)-1H-pyrazol-3-yl]benzenesulfonamide;

4-[5-(benzyloxymethyl)-4-(4-chlorophenyl)-1-(cyanomethyl)-1H-pyrazol-3-yl]benzenesulfonamide;

[3-4-[4-(aminosulfonyl)phenyl]-4-(4-chlorophenyl)-1-(cyanomethyl)-1H-pyrazol-5-yl]carboxylic acid;

methyl [3-[4-(aminosulfonyl)phenyl]-4-(4-chlorophenyl)-1-(cyanomethyl)-1H-pyrazol-5-yl]carboxylate;

N-phenyl -[3-[4-(aminosulfonyl)phenyl]-4-(4-chlorophenyl)-1-(cyanomethyl)-1H-pyrazol-5-yl]carboxamide;

4-[4-(4-chlorophenyl)-5-(difluoromethyl)-1-(3-propenyl)-1H-pyrazol-3-yl]benzenesulfonamide;

4-[4-(4-chlorophenyl)-5-(pentafluoroethyl)-1-(3-propenyl)-1H-pyrazol-3-yl]benzenesulfonamide;

4-[4-(4-chlorophenyl)-5-cyano-1-(3-propenyl)-1H-pyrazol-3-yl]benzenesulfonamide;

4-[4-(4-chlorophenyl)-5-methyl-1-(3-propenyl)-1H-pyrazol-3-yl]benzenesulfonamide;

4-[4-(4-chlorophenyl)-5-(hydroxymethyl)-1-(3-propenyl)-1H-pyrazol-3-yl]benzenesulfonamide;

4-[5-(benzyloxymethyl)-4-(4-chlorophenyl)-1-(3-propenyl)-1H-pyrazol-3-yl]benzenesulfonamide;

[3-[4-(aminosulfonyl)phenyl]-4-(4-chlorophenyl)-1-(3-propenyl)-1H-pyrazol-5-yl]carboxylic acid;

methyl [3-[4-(aminosulfonyl)phenyl]-4-(4chlorophenyl)-1-(3-propenyl)-1H-pyrazol-5-yl]carboxylate;

N-phenyl-[3-[4-(aminosulfonyl)phenyl]-4-(4-chlorophenyl)-1-(3-propenyl)-1H-pyrazol-5yl-]carboxamide;

4-[4-(4-chlorophenyl)-5-(difluoromethyl)-1-(2-phenylethyl)-1H-pyrazol-3-yl]benzenesulfonamide;

4-[4-(4-chlorophenyl)-5-(pentafluoroethyl)-1-(2-phenylethyl)-1H-pyrazol-3-yl]benzenesulfonamide;

4-[4-(4-chlorophenyl)-5-cyano-1-(2-phenylethyl)-1H-pyrazol-3-yl]benzenesulfonamide;

4-[4-(4-chlorophenyl)-5-methyl-1-(2-phenylethyl)-1H-pyrazol-3-yl]benzenesulfonamide;

4-[4-(4-chlorophenyl)-5-(hydroxymethyl)-1-(2-phenylethyl)-1H-pyrazol-3-yl]benzenesulfonamide;

4-[5-(benzyloxymethyl)-4-(4-chlorophenyl)-1-(2-phenylethyl)-1H-pyrazol-3-yl]benzenesulfonamide;

[3-[4-(aminosulfonyl)phenyl]-4-(4-chlorophenyl)-1-(2-phenylethyl)-1H-pyrazol-5-yl]carboxylic acid;

methyl [3-[4-(aminosulfonyl)phenyl]-4-(4chlorophenyl)-1-(2-phenylethyl)-1H-pyrazol-5-yl]carboxylate;

N-phenyl-[3-[4-(aminosulfonyl)phenyl]-4-(4chlorophenyl)-1 -(2-phenylethyl)-1H-pyrazol-5-yl ]carboxamide;

4-[5-(difluoromethyl)-1-ethyl-4-(4-methylphenyl)-1H-pyrazol-3-yl]benzenesulfonamide;

4-[1-ethyl-4-(4-methylphenyl)-5-(pentafluoroethyl)-1H-pyrazol-3-yl]benzenesulfonamide;

4-[5-cyano-1-ethyl-4 -(4-methylphenyl)-1H-pyrazol-3-yl]benzenesulfonamide;

4-[1-ethyl-5-methyl-4-(4-methylphenyl)-1H-pyrazol-3-yl]benzenesulfonamide;

4-[1-ethyl-5-(hydroxymethyl)-4-(4-methylphenyl)-1H-pyrazol-3-yl]benzenesulfonamide;

4-[5-(benzyloxymethyl)-1-ethyl-4-(4-methylphenyl)-1H-pyrazol-3 -yl]benzenesulfonamide;

[3-[4-(aminosulfonyl)phenyl]-1-ethyl-4-(4-methylphenyl)-1H-pyrazol-5-yl]carboxylic acid;

methyl [3-[4-(aminosulfonyl)phenyl]-1-ethyl-4-(4-methylphenyl)-1H-pyrazol-5-yl]carboxylate;

N-phenyl-[3-[4-(aminosulfonyl)phenyl]-1-ethyl-4-(4-methylphenyl)-1H-pyrazol-5-yl]carboxamide;

4-[1-benzyl-5-(difluoromethyl)-4-(4-methylphenyl)-1-H-pyrazol-3-yl]benzenesulfonamide;

4-[1-benzyl-4 - (4-methylphenyl)-5-(pentafluoroethyl)-1H-pyrazol-3-yl]benzenesulfonamide;

4-[1-benzyl-5-cyano-4-(4-methylphenyl)-1H-pyrazol-3-yl]benzenesulfonamide;

4-[1-benzyl-5-methyl-4-(4-methylphenyl)-1H-pyrazol-3-yl]benzenesulfonamide;

4-[1 -benzyl-5-(hydroxymethyl)-4-(4-methylphenyl)-1H-pyrazol-3-yl]benzenesulfonamide;

4-[1-benzyl-5-(benzyloxymethyl)-4-(4-methylphenyl)-1H-pyrazol-3-yl]benzenesulfonamide;

[3-[4-(aminosulfonyl)phenyl]-1-benzyl-4-(4-methylphenyl)-1H-pyrazol-5-yl]carboxylic acid;

methyl [3-[4-(aminosulfonyl)phenyl]-1-benzyl-4-(4-methylphenyl)-1H-pyrazol-5-yl]carboxylate;

N-phenyl-[3-[4-(aminosulfonyl)phenyl]-1-benzyl-4-(4-methylphenyl)-1H-pyrazol-5-yl]carboxamide;

4-[1-(cyanomethyl))-5-(difluoromethyl)-4-(4-methylphenyl)-1H-pyrazol-3-yl]benzenesulfonamide;

4-[1-ethyl-4-(4-methylphenyl)-(pentafluoroethyl)-1H-pyrazol-3-yl]benzenesulfonamide;

4-[5-cyano-1-(cyanomethyl)-4-(4-methylphenyl)-1H-pyrazol-3-yl]benzenesulfonamide;

4-[1-(cyanomethyl)-5-methyl-4-(4-methylphenyl)-1H-pyrazol-3-yl]benzenesulfonamide;

4-[1-(cyanomethyl)-4-(4-methylphenyl)-(hydroxymethyl)-1H-pyrazol-3-yl]benzenesulfonamide;

4-[5-(benzyloxymethyl)-1-(cyanomethyl)-4-(4-methylphenyl)-1H-pyrazol-3-yl]benzenesulfonamide;

3-[4-(aminosulfonyl)phenyl]-1-(cyanomethyl)-4-(4-methylphenyl)-1H-pyrazol-5-yl]carboxylic acid;

methyl[3-[4-(aminosulfonyl)phenyl]-1-(cyanomethyl)-4-(4-methylphenyl)-1H-pyrazol-5-yl]carboxylate;

N-phenyl-[3-[4-(aminosulfonyl)phenyl]-1-(cyanomethyl)-4(4-methylphenyl)-1H-pyrazol-5yl]carboxamide;

4-[5-(difluoromethyl)-4-(4-methylphenyl)-1-(3-propenyl)-1H-pyrazol-3-yl]benzenesulfonamide;

4-[4-(4-methylphenyl)-5-(pentafluoroethyl)-1-(3-propenyl)-1H-pyrazol-3-yl]benzenesulfonamide;

4-[5-cyano-4-(4-methylphenyl)-1-(3-propenyl)-1H-pyrazol-3-yl]benzenesulfonamide;

4-[5-methyl-4-(4-methylphenyl)-1-(3-propenyl)-1H-pyrazol-3-yl]benzenesulfonamide;

4-[5-(hydroxymethyl)-4-(4-methylphenyl)-1-(3-propenyl)-1H-pyrazol-3-yl]benzenesulfonamide;

4-[5-(benzyloxymethyl)-4-(4-methylphenyl)-1-(3-propenyl)-1H-pyrazol-3-yl]benzenesulfonamide;

[3-[4-(aminosulfonyl)phenyl]-4-(4-methylphenyl)-1-(3propenyl)-1H-pyrazol-5-yl]carboxylic acid;

methyl [3-[4-(aminosulfonyl)phenyl]-4-(4-methylphenyl)-1-(3-propenyl)-1H-pyrazol-5-yl]carboxylate;

N-phenyl-[3-[4-(aminosulfonyl)phenyl]-4-(4-methylphenyl)-1-(3-propenyl)-1H-pyrazol-5 -yl]carboxamide;

4-[5-(difluoromethyl)-4-(4-methylphenyl)-1-(2phenylethyl)-1H-pyrazol-3-yl]benzenesulfonamide;

4-[4-(4-methylphenyl)-5-(pentafluoroethyl)-1-(2-phenylethyl)-1H-pyrazol-3 -yl]benzenesulfonamide;

4-[5-cyano-4-(4-methylphenyl)-1-(2-phenylethyl)-1H-pyrazol-3 -yl]benzenesulfonamide;

4-[5-methyl-4-(4-methylphenyl)-1-(2-phenylethyl)-1H-pyrazol-3-yl]benzenesulfonamide;

4-[5-(hydroxymethyl)-4-(4-methylphenyl)-1-(2phenylethyl)-1H-pyrazol-3 -yl]benzenesulfonamide;

4-[5-(benzyloxymethyl)-4-(4-methylphenyl)-1-(2-phenyl-ethyl)-1H-pyrazol-3-yl]benzenesulfonamide;
[3-[4-(aminosulfonyl)phenyl]-4-(4-methylphenyl)-1-(2phenylethyl)-1H-pyrazol-5-yl]carboxylic acid;
methyl[3-[4-(aminosulfonyl)phenyl]-4-(4-methylphenyl)-1-(2-phenylethyl)-1H-pyrazol-5-yl]carboxylate;
N-phenyl-[3-[4-(aminosulfonyl)phenyl]-4-(4-methylphenyl)-1-(2 -phenylethyl)-1H-pyrazol-5-yl]carboxamide;
4-[5-(difluoromethyl)-1-ethyl-4-(3-fluoro-4- methoxyphenyl)-1H-pyrazol-3-yl]benzenesulfonamide;
4-[1-ethyl-4-(3-fluoro-4-methoxyphenyl)-5(pentafluoroethyl)-1H-pyrazol-3 yl]benzenesulfonamide;
4-[5-cyano-1-ethyl-4-(3 -fluoro-4-methoxyphenyl)-1H-pyrazol-3-yl]benzenesulfonamide;
4-[1-ethyl-4-(3-fluoro-4-methoxyphenyl)-5-methyl-1H-pyrazol-3-yl]benzenesulfonamide;
4-[1-ethyl-4-(3-fluoro-4-methoxyphenyl)-5-(hydroxymethyl)-1H-pyrazol- 3-yl]benzenesulfonamide;
4-[5-(benzyloxymethyl)-1-ethyl-4-(3-fluoro-4-methoxyphenyl)-1-pyrazol-3-yl]benzenesulfonamide;
[3-[4-(aminosulfonyl)phenyl]-1-ethyl-4-(3-fluoro-4-methoxyphenyl)-1H-pyrazol-5-yl]carboxylic acid;
methyl [3-[4-(aminosulfonyl)phenyl]-1-ethyl-4-(3-fluoro-4-methoxyphenyl)-1H-pyrazol-5-yl]carboxylate;
N-phenyl-[3-[4 -(aminosulfonyl)phenyl]-1-ethyl-4-(3-fluoro-4-methoxyphenyl)-1H-pyrazol-5-yl]carboxamide;
4-[1-benzyl-5-(difluoromethyl)-4-(3-fluoro-4-methoxyphenyl)-1H-pyrazol-3-yl]benzenesulfonamide;
4-[1-benzyl-4-(3-fluoro-4-methoxyphenyl)-5-(pentafluoroethyl)-1H-pyrazol-3 yl]benzenesulfonamide;
4-[1-benzyl-5-cyano-4-(3-fluoro-4-methoxyphenyl)-1H-pyrazol-3-yl]benzenesulfonamide;
4-[1-benzyl-4-(3-fluoro-4-methoxyphenyl)-5-methyl-1H-pyrazol-3-yl]benzenesulfonamide;
4-[1-benzyl-4-(3-fluoro-4-methoxyphenyl)-5-(hydroxymethyl)-1H-pyrazol-3yl]benzenesulfonamide;
4-[1-benzyl-5-(benzyloxymethyl)-4-(3-fluoro-4-methoxyphenyl)-1H-pyrazol-3-yl]benzenesulfonamide;
[3-[4-(aminosulfonyl)phenyl]-1-benzyl-4-(3-fluoro-4-methoxyphenyl)-1H-pyrazol-5-yl]carboxylic acid;
methyl [3-[4-(aminosulfonyl)phenyl]-1-benzyl-4-(3-fluoro-4-methoxyphenyl)-1H-pyrazol-5-yl]carboxylate;
N-phenyl-[3-[4-(aminosulfonyl)phenyl]-1-benzyl-4-(3-fluoro-4-methoxyphenyl)-1H-pyrazol-5-yl]carboxamide;
4-[1-(cyanomethyl)-5-(difluoromethyl)-4-(3-fluoro-4-methoxyphenyl)-1H-pyrazol-3-yl]benzenesulfonamide;
4-[1-ethyl-4-(3-fluoro-4-methoxyphenyl)-35(pentafluoroethyl)-1H-pyrazol-3-yl]benzenesulfonamide;
4-[5-cyano-1-(cyanomethyl)-4-(3-fluoro-4-methoxyphenyl)-1H -pyrazol-3yl]benzenesulfonamide;
4-[1-(cyanomethyl)-4-(3-fluoro-4-methoxyphenyl)-5-methyl-1H-pyrazol-3-yl]benzenesulfonamide;
4-[1-(cyanomethyl)-4-(3-fluoro-4-methoxyphenyl)-5-(hydroxymethyl)-1H-pyrazol-3-yl]benzenesulfonamide;
4-[5-(benzyloxymethyl)-1-(cyanomethyl)-4-(3-fluoro-4-methoxyphenyl)-1H-pyrazol-3yl]benzenesul fonamide;
[3-[4-(aminosulfonyl)phenyl]-1-(cyanomethyl)-4-(3-fluoro-4-methoxyphenyl)-1H-pyrazol-5-yl]carboxylic acid;
methyl [3-[4-(aminosulfonyl)phenyl]-1 -(cyanomethyl)-4-(3-fluoro-4 -methoxyphenyl)-1H-pyrazol-5-yl]carboxylate;
N-phenyl-[3-[4-(aminosulfonyl)phenyl]-1-(cyanomethyl)-4-(3-fluoro-4-methoxyphenyl)-1H-pyrazol-5-yl]carboxamide;
4-[5-(difluoromethyl)-4-(3 -fluoro-4-methoxyphenyl)-1(3-propenyl)-1H-pyrazol-3-yl]benzenesulfonamide;
4-[4-(3-fluoro-4-methoxyphenyl)-5-(pentafluoroethyl)-1-(3-propenyl)-1H-pyrazol-3-yl]benzenesulfonamide;
4-[5-cyano-4-(3-fluoro-4-methoxyphenyl)-1-(3propenyl)-1H-pyrazol-3-yl]benzenesulfonamide;
4-[4-(3-fluoro-4-methoxyphenyl)-5-methyl-1-(3propenyl)-1H-pyrazol-3-yl]benzenesulfonamide;
4-[4-(3-fluoro-4-methoxyphenyl)-5-(hydroxymethyl)-1-(3-propenyl)-1H-pyrazol-3-yl]benzenesulfonamide;
4-[5-(benzyloxymethyl)-4-(3-fluoro- 4-methoxyphenyl)-1(3-propenyl)-1H-pyrazol-3-yl]benzenesulfonamide;
[3-[4-(aminosulfonyl)phenyl]-4-(3-fluoro-4-methoxyphenyl)-1-(3-propenyl)-1H-pyrazol-5-yl]carboxylic acid;
methyl[3-[4-(aminosulfonyl)phenyl]-4-(3-fluoro-4-methoxyphenyl)-1-(3 -propenyl)-1H-pyrazol-5-yl]carboxylate;
N-phenyl-[3-[4 -(aminosulfonyl)phenyl]-4-(3-fluoro-4-methoxyphenyl)-1-(3-propenyl)-1H-pyrazol-5-yl]carboxamide;
4-[5-(difluoromethyl)-4-(3-fluoro-4-methoxyphenyl)-1-(2-phenylethyl)-1H-pyrazol-3-yl]benzenesulfonamide;
4-[4-(3-fluoro-4-methoxyphenyl)-5-(pentafluoroethyl)-1-(2-phenylethyl)-1H-pyrazol-3-yl]benzenesulfonamide;
4-[5-cyano-4-(3-fluoro-4-methoxyphenyl)-1- (2-phenylethyl)-1H-pyrazol-3-yl]benzenesulfonamide;
4-[4-(3-fluoro-4-methoxyphenyl)-5-methyl-1- (2-phenylethyl)-1H-pyrazol-3-yl]benzenesulfonamide;
4-[4-(3 -fluoro-4-methoxyphenyl)-5-(hydroxymethyl)-1(2-phenylethyl)-1H-pyrazol-3yl]benzenesulfonamide;
4-[5-(benzyloxymethyl)-4-(3-fluoro-4-methoxyphenyl)-1(2-phenylethyl)-1H-pyrazol-3-yl]benzenesulfonamide;
[3-[4-(aminosulfonyl)phenyl]-4-(3-fluoro-4-methoxyphenyl)-1-(2 -phenylethyl)-1H-pyrazol- 5-yl]carboxylic acid;
methyl [3-[4-(aminosulfonyl)phenyl]-4-(3-fluoro-4-methoxyphenyl)-1-(2-phenylethyl)-1H-pyrazol-5-yl]carboxylate; and
N-phenyl-[3-[4-(aminosulfonyl)phenyl]-4-(3-fluoro-4-methoxyphenyl)-1-(2-phenylethyl)-1H-pyrazol-5-yl]carboxamide.

Within Formula I there is a subclass of compounds of high interest represented by Formula II:

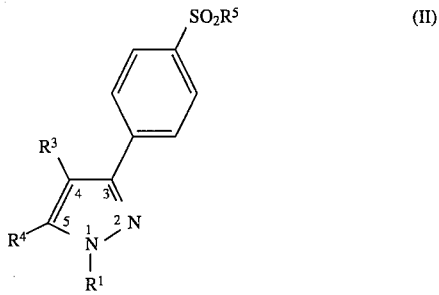

wherein $R^1$ is selected from hydrido, alkyl, alkenyl, aralkyl, alkynyl, cyanoalkyl, carboxyalkyl, aminocarbonylalkyl, arylaminocarbonylalkyl, heterocyclicalkyl, and alkoxycarbonylalkyl;

wherein $R^3$ is aryl substituted at a substitutable position with halo;

wherein $R^4$ is selected from hydrido and haloalkyl; and wherein $R^5$ is selected from alkyl and amino;

or a pharmaceutically-acceptable salt or prodrug thereof.

A preferred class of compounds consists of those compounds of Formula II wherein $R^1$ is selected from hydrido, lower alkyl, lower alkenyl, lower aralkyl, lower alkynyl, lower cyanoalkyl, lower carboxyalkyl, lower aminocarbonylalkyl, lower arylaminocarbonylalkyl, lower heterocyclicalkyl and lower alkoxycarbonylalkyl;

wherein $R^3$ is aryl selected from phenyl, naphthyl and biphenyl, wherein said aryl radical is substituted at a substitutable position with at least one halo radical;

wherein R⁴ is selected from hydrido and lower haloalkyl; and wherein R⁵ is selected from lower alkyl and amino.

A class of compounds of particular interest consists of those compounds of Formula II wherein R¹ is selected from hydrido, methyl, ethyl, propyl, isopropyl, butyl, isobutyl, tert-butyl, ethenyl, propenyl, allyl, butenyl, isobutenyl, benzyl, phenylethyl, phenylpropyl, propargyl, cyanomethyl, cyanoethyl, acetyl, propanyl, butanyl, morpholinomethyl, pyrrolidinylmethyl, piperazinylmethyl, piperidinylmethyl, tetrahydrofurylmethyl, acetamidyl, phenylacetamidyl, methoxycarbonylmethyl, ethoxycarbonylmethyl, isopropoxycarbonylmethyl, tert-butoxycarbonylmethyl, propoxycarbonylethyl, butoxycarbonylethyl, isobutoxycarbonylmethyl and pentoxycarbonylmethyl;

wherein R³ is phenyl substituted at a substitutable position with at least one radical selected from fluoro, chloro, bromo and iodo;

wherein R⁴ is selected from hydrido, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl; and wherein R⁵ is selected from methyl, ethyl, and amino.

A family of specific compounds of particular interest within Formula II consists of compounds and pharmaceutically-acceptable salts thereof as follows:

4-(4-fluorophenyl)-3-[4-(methyl sulfonyl)phenyl]-1-(2-phenylethyl)-5-(trifluoromethyl)-1H-pyrazole;

1-cyanomethyl-4-(4-fluorophenyl)-3-[4(methylsulfonyl)phenyl]-5-(trifluoromethyl)-1H-pyrazole;

4-(4-fluorophenyl)-3-[4-(methylsul fonyl)phenyl]-1propargyl)-5-(trifluoromethyl)-1H-pyrazole;

1-benzyl-4-(4-fluorophenyl)-3-[4(methylsulfonyl)phenyl]-5-(trifluoromethyl)-1H-pyrazole;

4-(4-fluorophenyl)-1-methyl-3-[4(methylsulfonyl)phenyl]-5-(trifluoromethyl)-1H-pyrazole;

4-(4-fluorophenyl)-3-[4-(methylsulfonyl)phenyl]-1(2-phenylethyl)-5-(trifluoromethyl)-1H-pyrazole;

1-ethyl-4-(4-fluorophenyl)-3-[4(methylsulfonyl)phenyl]-5-(trifluoromethyl)-1H-pyrazole;

4-(4-fluorophenyl)-3 -[4-(methylsulfonyl)phenyl]-1-[2-(1H-pyrrolidin-1-yl)ethyl]-5-(trifluoromethyl)-1H-pyrazole;

ethyl [4-(4-fluorophenyl)-3-[4-(methylsulfonyl)phenyl]-5-(trifluoromethyl)-1H-pyrazol-1-yl]acetate;

N-phenyl[4-(4-fluorophenyl)-3-[4-(methylsulfonyl)phenyl] -5-(trifluoromethyl)-1H-pyrazol-1-yl]acetamide;

[4-(4-fluorophenyl)-3-[4-(methylsulfonyl)phenyl]-5-(trifluoromethyl)-1H-pyrazol-1-yl]acetic acid;

[4-(4-fluorophenyl)- 3-[4-(methylsulfonyl)phenyl]-5-(trifluoromethyl)-1H-pyrazol-1-yl]acetamide;

4-(4-fluorophenyl)-3-[4-(methylsulfonyl)phenyl]-1-allyl-5-trifluoromethyl-1H -pyrazole;

[4-(4-fluorophenyl)-3-[4-(methylsulfonyl)phenyl]-1H-pyrazol-1-yl]acetic acid; and 4-[1-ethyl-4-(4-fluorophenyl)-5-(trifluoromethyl)-1H-pyrazol-3-yl]benzenesulfonamide.

The term "hydrido" denotes a single hydrogen atom (H). This hydrido radical may be attached, for example, to an oxygen atom to form a hydroxyl radical or two hydrido radicals may be attached to a carbon atom to form a methylene (—CH₂—) radical. Where the term "alkyl" is used, either alone or within other terms such as "haloalkyl", "alkylsulfonyl", "alkoxyalkyl" and "hydroxyalkyl", embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. Where the term "alkenyl" is used, it embraces linear or branched carbon carbon double bond-containing radicals having two to about twenty carbon atoms or, preferably, two to about twelve carbon atoms. More preferred alkenyl radicals are "lower alkenyl" radicals having two to about six carbon atoms. Suitable "lower alkenyl" may be a straight or branched one such as vinyl, allyl, isopropenyl, propenyl, butenyl, pentenyl or the like, in which preferably one is isopropenyl. Said lower alkenyl may be substituted with cyano. Where the term "alkynyl" is used, it embraces linear or branched carbon carbon triple bond-containing radicals having two to about twenty carbon atoms or, preferably, two to about twelve carbon atoms. More preferred alkynyl radicals are "lower alkynyl" radicals having two to about six carbon atoms. Suitable "lower alkynyl" may be a straight or branched one such as ethynyl, propynyl, propargyl or the like, in which preferably one is propargyl. The term "halo" means halogens such as fluorine, chlorine, bromine or iodine. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1–6 carbon atoms. Examples of haloalkyl radicals include fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. The term "cyanoalkyl" embraces radicals having a cyano or nitrile (–CN) radical attached to an alkyl radicals as described above. More preferred cyanoalkyl radicals are "lower cyanoalkyl" radicals having one to six carbon atoms. Examples of such lower cyanoalkyl radicals include cyanomethyl, cyanopropyl, cyanoethyl and cyanobutyl. The terms "alkoxy" and "alkoxyalkyl" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. The term "alkoxyalkyl" also embraces alkyl radicals having two or more alkoxy radicals attached to the alkyl radical, that is, to form monoalkoxyalkyl and dialkoxyalkyl radicals. More preferred alkoxyalkyl radicals are "lower alkoxyalkyl" radicals having one to six carbon atoms and one or two alkoxy radicals. Examples of such radicals include methoxymethyl, methoxyethyl, ethoxyethyl, methoxybutyl and methoxypropyl. The "alkoxy" or "alkoxyalkyl" radicals may be further substituted with one or more halo atoms, such as fluoro, chloro or bromo, to provide haloalkoxy or haloalkoxyalkyl radicals. More preferred haloalkoxy radicals are "lower haloalkoxy" radicals having one to six carbon atoms and one or more halo radicals. Examples of such radicals include fluoromethoxy, chloromethoxy, trifluoromethoxy, trifluoroethoxy, fluoroethoxy and fluoropropoxy. The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronapthyl, indane and biphenyl. The terms "heterocyclo" and "heterocyclic" embrace saturated, partially saturated and unsaturated heteroatom-containing ring-shaped radicals, where the heteroatoms may be selected from nitrogen, sulfur and oxygen. Examples of saturated heterocyclic radicals include saturated 3 to 6-membered heteromonocylic group containing 1 to 4 nitrogen atoms[e.g. pyrrolidinyl, imidazolidinyl, piperidino, piperazinyl, etc.]; saturated 3 to 6-membered heteromonocyclic group containing 1 to 2 oxygen atoms and 1 to 3 nitrogen atoms [e.g. morpholinyl, etc.]; saturated 3 to 6-membered heteromonocyclic group containing 1 to 2 sulfur atoms and 1 to 3 nitrogen atoms [e.g., thiazolidinyl, etc.]. Examples of partially saturated heterocyclic radicals include dihydrothiophene, dihydropyran, dihydrofuran and dihydrothiazole. The term "heteroaryl" embraces unsaturated heterocyclic radicals. Examples of unsaturated heterocyclic radicals, also termed "heteroaryl" radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl [e.g., 4H-1,2,4-triazolyl, 1H-1,2,3-triazolyl, 2H-1,2,3-triazolyl, etc.] tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b]pyridazinyl, etc.], etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2, 5-oxadiazolyl, etc.] etc.; unsaturated condensed heterocyclic group containing 1 to 2 oxygen atoms and 1 to 3 nitrogen atoms [e.g. benzoxazolyl, benzoxadiazolyl, etc.]; unsaturated 3 to 6-membered heteromonocyclic group containing 1 to 2 sulfur atoms and 1 to 3 nitrogen atoms, for example, thiazolyl, thiadiazolyl [e.g., 1,2,4- thiadiazolyl, 1,3,4thiadiazolyl, 1,2,5-thiadiazolyl, etc.]etc.; unsaturated condensed heterocyclic group containing 1 to 2 sulfur atoms and 1 to 3 nitrogen atoms [e.g., benzothiazolyl, benzothiadiazolyl, etc.] and the like. The term also embraces radicals where heterocyclic radicals are fused with aryl radicals. Examples of such fused bicyclic radicals include benzofuran, benzothiophene, and the like. Said "heterocyclic group" may have 1 to 3 substituents such as lower alkyl, hydromy, oxo, amino and lower alkylamino. The term "heterocyclicalkyl" embraces heterocyclic-substituted alkyl radicals. More preferred heterocyclicalkyl radicals are "lower heterocyclicalkyl" radicals having one to six carbon atoms and a heterocyclic radical. Examples include such radicals as pyrrolidinylmethyl. The term "heteroaralkyl" embraces heteroaryl-substituted alkyl radicals. More preferred heteroaralkyl radicals are "lower heteroaralkyl" radicals having one to six carbon atoms and a heteroaryl radical. Examples include such heteroaralkyl radicals such as pyridylmethyl and thienylmethyl. The term "alkylthio"embraces radicals containing a linear or branched alkyl radical, of one to about ten carbon atoms attached to a divalent sulfur atom. More preferred alkylthio radicals are "lower alkylthio" radicals having alkyl radicals of one to six carbon atoms. Examples of such lower alkylthio radicals are methylthio, ethylthio, propylthio, butylthio and hexylthio. The term "alkylsulfinyl" embraces radicals containing a linear or branched alkyl radical, of one to ten carbon atoms, attached to a divalent —S(=O)-radical. More preferred alkylsulfinyl radicals are "lower alkylsulfinyl" radicals having one to six carbon atoms. Examples of such lower alkylsulfinyl radicals include methylsulfinyl, ethylsulfinyl, butysulfinyl and hexylsulfinyl. The term "sulfonyl", whether used alone or linked to other terms such as alkylsulfonyl, denotes respectively divalent radicals —SO$_2$—. "Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Examples of such lower alkylsulfonyl radicals include methylsulfonyl, ethylsulfonyl and propylsulfonyl. The "alkylsulfonyl" radicals may be further substituted with one or more halo atoms, such as fluoro, chloro or bromo, to provide "haloalkylsulfonyl" radicals. More preferred haloalkylsulfonyl radicals are "lower haloalkylsulfonyl" radicals having one or more halo atoms attached to lower alkylsulfonyl radicals as described above. Examples of such lower haloalkylsulfonyl radicals include fluoromethylsulfonyl, trifluoromethylsulfonyl and chloromethylsulfonyl. The terms "sulfamyl", "aminosulfonyl" and sulfonamidyl denotes NH$_2$O$_2$S—. The term "acyl" denotes a radical provided by the residue after removal of hydroxyl from an organic acid. Examples of such acyl radicals include alkanoyl and aroyl radicals. The terms "carboxy" or "carboxyl", whether used alone or with other terms, such as "carboxyalkyl", denotes —CO$_2$H. The term "carbonyl", whether used alone or with other terms, such as "alkoxycarbonyl", denotes —(C=O)—. The term "alkoxycarbonyl" means a radical containing an alkoxy radical, as defined above, attached via an oxygen atom to a carbonyl radical. Preferably, "lower alkoxycarbonyl" embraces alkoxy radicals having one to six carbon atoms. Examples of such "alkoxycarbonyl"ester radicals include substituted or unsubstituted methoxycarbonyl, ethoxycarbonyl, propoxycarbonyl, butoxygarbonyl and hexyloxycarbonyl. The term "alkoxycarbonylalkyl" embraces radicals having "alkoxycarbonyl", as defined above substituted to an alkyl radical. More preferred alkoxycarbonyl radicals are "lower alkoxycarbonylalkyl" radicals having alkoxycarbonyl radicals as defined above attached to alkyl radicals having one to six carbon atoms. The term "aryloxycarbonyl" embraces aryl radicals attached to a carbonyl radical. Examples of similar radicals include substituted or unsubstituted "aryloxycarbonyl"[e.g. phenoxycarbonyl, 4-nitrophenoxycarbonyl, 2-naphthyloxycarbonyl, etc.], substituted or unsubstituted "aralkoxycarbonyl" [e.g. benzyloxycarbonyl, phenylethyloxycarbonyl, benzhydryloxycarbonyl, 4-nitrobenzyloxycarbonyt, etc.]and the like. The terms "alkanoyl" or "carboxyalkyl"embrace radicals having a carboxy radical as defined above, attached to an alkyl radical. The alkanoyl radicals may be a substituted or unsubstituted one such as formyl, acetyl, propionyl, butyryl, isobutyryl, valeryl, isovaleryl, pivaloyl, hexanoyl, trifluoroacetyl or the like, in which the preferable one is formyl, acetyl, propionyl or trifluoroacetyl. The term "aralkyl" embraces aryl-substituted alkyl radicals such as benzyl, diphenylmethyl, triphenylmethyl, phenylethyl, and diphenylethyl. The aryl in said aralkyl may be additionally substituted. The terms benzyl and phenylmethyl are interchangeable. The term "cycloalkyl" embraces radicals having three to ten carbon atoms, such as cyclopropyl, cyclobutyl, cyclopentyl, cyclohexyl and cycloheptyl. The term "cycloalkenyl" embraces unsaturated radicals having three to ten carbon atoms, such as cylopropenyl, cyclobutenyl, cyclopentenyl, cyclohexenyl and cycloheptenyl. The term "aralkoxy" embrace oxy-containing aralkyl radicals attached through an oxygen atom to other radicals. The term "aralkoxyalkyl"embraces alkyl radicals having one or more aralkoxy radicals attached to the alkyl radical, that is, to form monoaralkyloxyalkyl and diaralkyloxyalkyl radicals. The "aralkoxy" or "aralkoxyalkyl" radicals may be further substituted on the aryl ring portion of the radical. The term "aralkoxycarbonylalkyl" embraces aralkoxycarbonyl radicals, as defined above, attached to a carbonyl radical. More preferred aralkoxycarbonylalkyl radicals are "lower aralkoxycarbonylalkyl" radicals having aralkoxycarbonyl radicals attached to alkyl radicals having one to six carbon atoms. The term "aminoalkyl"embraces alkyl radicals substituted with amino radicals. The term "alkylaminoalkyl" embraces aminoalkyl radicals having the nitrogen atom substituted with at least one alkyl radical. The term "alkylamino" denotes amino groups which have been substituted with one or two alkyl radicals. Suitable "alkylamino" may be mono or dialkylamino such as N-methylamino, N-ethylamino, N,N-dimethylamino, N,N-diethylamino or the like. The term "arylamino" denotes amino groups which have been substituted with one or two aryl radicals, such as N-phenylamino. The "arylamino" radicals may be further substituted on the aryl ring portion of the radical. The term "aminocarbonyl" denotes an amide group of the formula —C(=O)NH$_2$. The term "aminocarbonylalkyl" denotes an aminocarbonyl group which is attached to an alkyl radical. More preferred are "lower aminocarbonylalkyl" having aminocarbonyl radicals as described above attached to one to six carbon atoms. The term "alkylaminocarbonyl" denotes an aminocarbonyl group which has been substituted with one or two alkyl radicals. The term "alkylaminocarbonylalkyl" denotes an alkylaminocarbonyl group which has been attached to an alkyl radical. More preferred are "lower alkylaminocarbonylalkyl" having lower alkylaminocarbonyl radicals as described above attached to one to six carbon atoms. The term "arylaminocarbonyl" denotes an aminocarbonyl group which has been substituted with one or two aryl radicals. The arylaminocarbonyl may be optionally substituted at a substituted position on the aryl radical with halo, lower alkyl and lower alkoxy radicals. Examples include phenylaminocarbonyl, naphthylamideaminocarbonyl, tolylaminocarbonyl, xylylaminocarbonyl, mesitylaminocarbonyl, cumenylaminocarbonyl, fluorophenylcarbonyl, methylphenylcarbonyl and methoxyphenylcarbonyl. The term "alkyl-aryl-aminocarbonyl" denotes an aminocarbonyl group which has been substituted with one aryl radical and one alkyl radical. The term "hydroxyaminocarbonyl" denotes an aminocarbonyl group which has been substituted with a hydroxy radical. The term "hydroxy-alkyl-aminocarbonyl" denotes an hydroxyaminocarbonyl group which has been substituted with an alkyl radical.

The present invention comprises a pharmaceutical composition comprising a therapeutically-effective amount of a compound of Formula I in association with at least one pharmaceutically-acceptable carrier, adjuvant or diluent.

The present invention also comprises a method of treating inflammation or inflammation-associated disorders in a subject, the method comprising administering to the subject having such inflammation or disorder a therapeutically-effective amount of a compound of Formula I.

Also included in the family of compounds of Formula I are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, cyclohexylaminosulfonic, algenic, β-hydroxybutyric, salicyclic, galactaric and galacturonic acid. Suitable pharmaceutically-acceptable base addition salts of compounds of Formula I include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

GENERAL SYNTHETIC PROCEDURES

The compounds of the invention can be synthesized according to the following procedures of Schemes I–VI, wherein the $R^1$–$R^5$ substituents are as defined for Formula I, above, except where further noted.

Scheme I

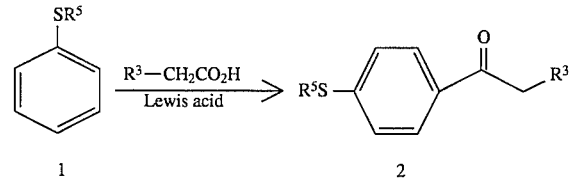

Scheme I shows the procedure for forming substituted aryl ketones 2, where $R^2$ is phenyl substituted with $R^5$–S– where $R^5$ is alkyl, from the corresponding aryl sulfides 1. Sulfides 1, such as thioanisole, are reacted with a substituted acetic acid, such as a phenyl or cycloalkylacetic acid, under Lewis acid catalyzed conditions, preferably using polyphosphoric acid (PPA) as the Lewis acid, to provide phenyl ketone 2.

Scheme II

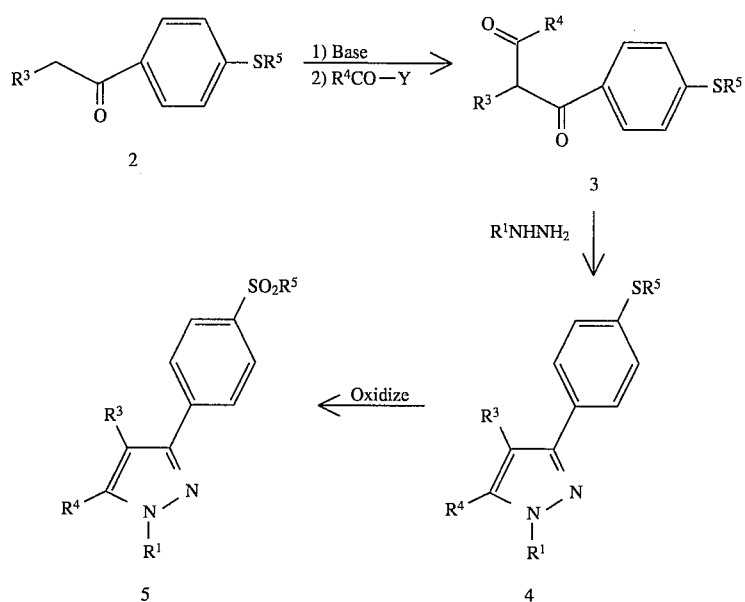

Scheme II shows the four step procedure for forming pyrazoles 5 of the present invention (where $R^5$ is alkyl) from ketones 2. In step 1, ketone 2 is reacted with a base, such as lithium bis(trimethylsilyl)amide or lithium diisopropylamide (LDA) to form the anion. In step 2, the anion is reacted with an acetylating reagent, preferably 1-trifluoroacetylimidazole or 1-difluoroacetylimidazole, provides diketone 3. In step 3, the reaction of diketone 3 with hydrazine or a substituted hydrazine, gives pyrazole 4. In step 4, the pyrazole 4 is oxidized with an oxidizing reagent, such as Oxone® (potassium peroxymonosulfate), 3-chloroperbenzoic acid (MCPBA) or hydrogen peroxide, to give a mixture of the desired 3-(alkylsulfonyl)phenyl-pyrazole 5 and the 5-(alkylsulfonyl)phenyl-pyrazole isomer. The desired pyrazole 5, usually a white or pale yellow solid, is obtained in pure form either by chromatography or recrystallization.

Alternatively, diketone 3 can be formed from ketone 2 by treatment with a base, such as sodium hydride, in a solvent, such as dimethylformamide, and further reacting with a nitrile to form an aminoketone. Treatment of the aminoketone with acid forms the diketone 3.

Scheme III

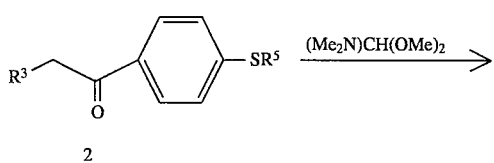

-continued
Scheme III

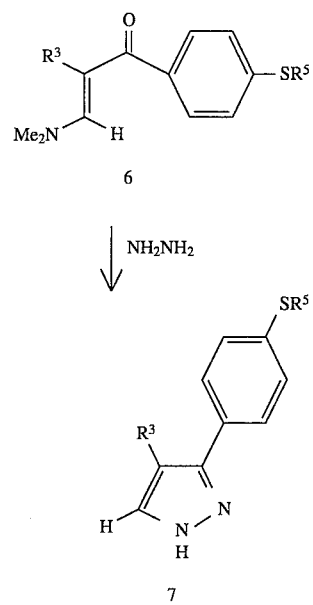

Scheme III shows an alternative two step synthesis of pyrazole analogs 7 where $R^1$ is hydrogen. In Step 1, ketone 2, prepared as described in Scheme I, is heated (100°–120° C.) with a formamide equivalent, such as DMF-dimethyl acetal, either neat or in DMF to provide enamino-ketone 6. In Step 2, the reaction of enamino-ketone 6 with hydrazine gives the desired pyrazole 7.

Scheme IV

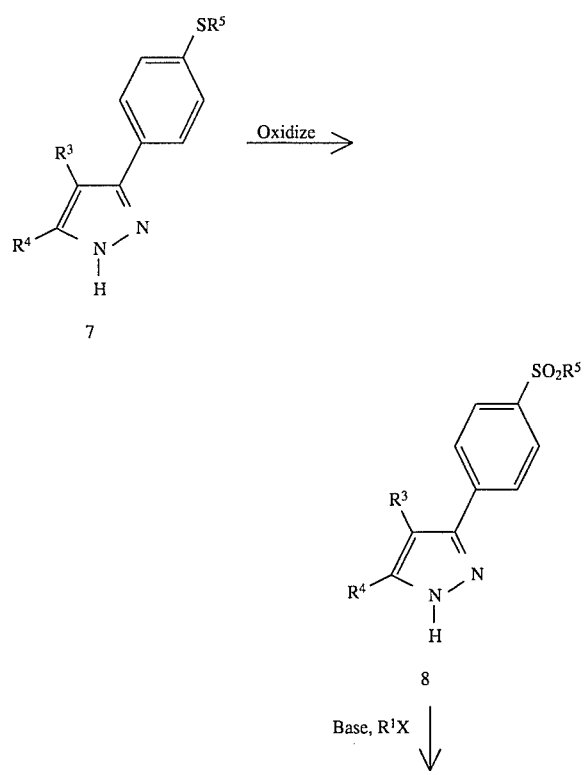
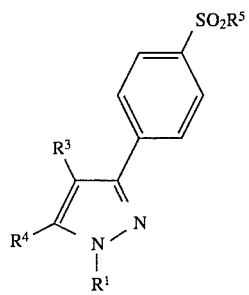

Scheme IV shows a procedure for forming the 3-(alkylsulfonyl)phenyl-pyrazoles 8 of the present invention as well as an alternate synthesis of the desired 3-(alkylsulfonyl)phenyl-1-substituted pyrazoles 5 from pyrazoles 7 (where $R^1$ is hydrogen). In step 1, the pyrazole 7 is oxidized with an oxidizing reagent, such as Oxone® (potassium peroxymonosulfate), 3-chloroperbenzoic acid (MCPBA) or hydrogen peroxide to form the desired 3-(alkylsulfonyl)phenyl-pyrazoles 8. In step 2, the reaction of 3-(alkylsulfonyl)phenyl-pyrazoles 8 with a variety of alkylating reagents, such as an alkyl halide, in the presence of a base, such as $K_2CO_3$, in a polar aprotic solvent such as DMF, gives a mixture of the desired 3-(alkylsulfonyl)phenyl-1-substituted pyrazole 5 and the 5-(alkylsulfonyl)phenyl-pyrazole isomer. The desired pyrazoie 5 is purified, such as by chromatography or recrystallization.

Scheme V

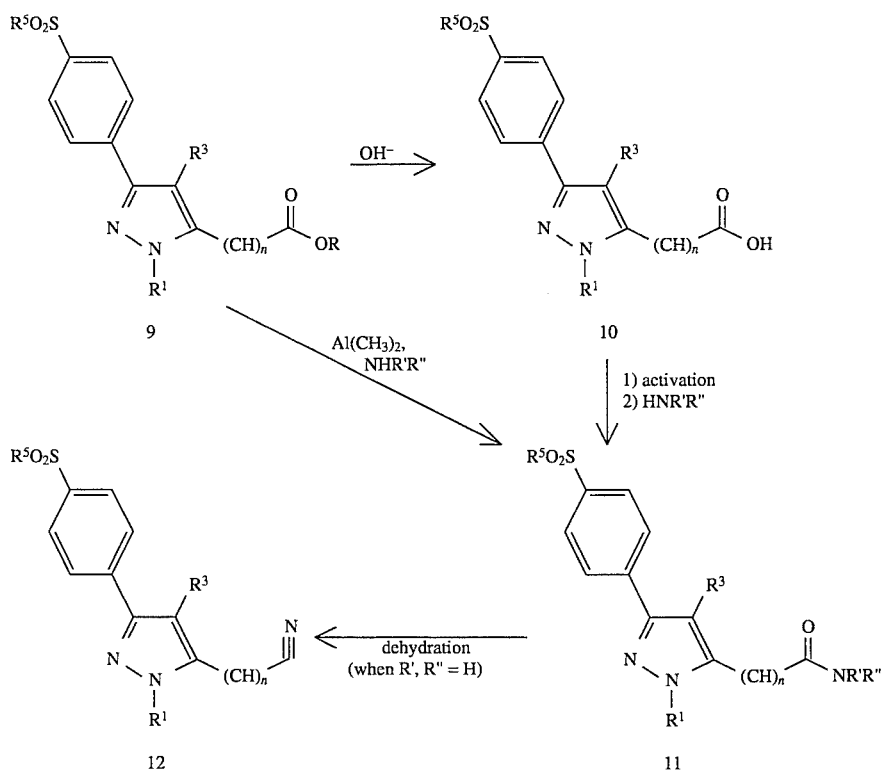

Scheme V shows an alternate method for preparing antiinflammatory pyrazoles with various $R^4$ substituents. In Step 1, pyrazoles 9, where $R^4$ is an ester, (where R is alkyl and n is 0 to 6) are converted to the corresponding acids 10 by saponification, preferably with sodium hydroxide or lithium hydroxide. In Step 2, the acids 10 can be converted into the amides 11 (where R' and R" are hydrogen or alkyl) by standard peptide amino acid coupling conditions (M. Bodanszky and A. Bodanszky, *Practice of Peptide Synthesis* (1984)) involving conversion of the acid 10 into an activated ester or amide (i.e with carbonyl diimidazole), followed by coupling with an amine. Amides 11 can additionally be prepared using Weinreb trimethyl aluminum conditions (Tetrahedron Lett., 18, 4171 (1977)) on ester 9. When the amide 11 is unsubstituted (when $R^6$ and $R^7$ are hydrogen), the nitrile 12 can be obtained by dehydration.

Scheme VI

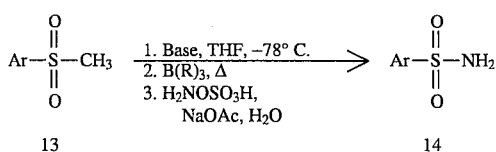

13      14

Synthetic Scheme Vi shows the three step procedure used to prepare sulfonamide antiinflammatory agents 14 from their corresponding methyl sulfones 13. In step one, a THF solution of the methyl sulfones 13 at −78° C. is treated with a base such as an alkyllithium reagent, e.g., methyllithium, n-butyllithium, etc., or a Grignard reagent, e.g., n-butyl magnesium chloride. In step two, the anions generated in step one are treated with an organoborane, e.g., triethylborane, tributylborane, etc., at −78° C. then allowed to warm to ambient temperature prior to stirring at reflux. In step three, an aqueous solution of sodium acetate and hydroxyamine-O-sulfonic acid is added to provide the corresponding sulfonamide antiinflammatory agents of this invention.

The following examples contain detailed descriptions of the methods of preparation of compounds of Formula I-II. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated.

EXAMPLE 1

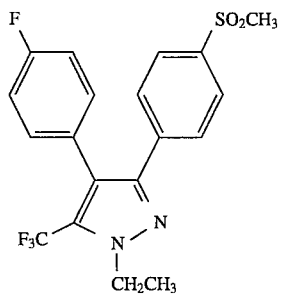

1-Ethyl-4-(4-fluorophenyl)-3-[4-(methylsulfonyl) phenyl]-5-(trifluoromethyl)-1H-pyrazole Step 1:

Preparation of 2-(4-fluorophenyl)-1-[4-(methylthio)phenyl]ethanone

Thioanisole (10.1 g, 81.5 mmol) and 4-fluorophenylacetic acid (10.0 g, 65 mmol) were combined in a round bottom 3-neck flask. Polyphosphoric acid (PPA) (160 g), warmed to 60° C., was added and the mixture was heated to 120°–125° C. under nitrogen with vigorous stirring for 20 minutes. Upon cooling to 40° C., ice water and ice were added with vigorous stirring. The temperature was kept below 85° C. during the quench and dissolution of PPA. After cooling to 25° C., the white solids were filtered off, washed with two portions of water and dried. Recrystallization from ethyl acetate-hexane afforded the ketone (10.7 g, 63%): mp 139°–140° C. Elemental analysis Calc'd. for $C_{15}H_{13}FOS$: C, 69.21, H, 5.03, S, 12.32. Found: C, 68.74, H, 5.09, S, 12.15.

Step 2:

Preparation of 4-(4-fluorophenyl)-3-[4-(methylthio)phenyl]-5-(trifluoromethyl)-1H-pyrazole A suspension of 2-(4-fluorophenyl)-1-[4(methylthio)phenyl]ethanone from Step 1 (11.53 g, 44 mmol) in 225 mL dry tetrahydrofuran (THF) was treated with 52.8 mL lithium bis(trimethylsilyl) amide (1.0M in THF) at −70° C. under nitrogen for 30 minutes and warmed to 0° C. for 30 minutes. Upon cooling to −70° C., a solution of 10.0 g (61 mmol) 1-trifluoroacetylimidazole in 25 mL THF was added and the mixture warmed to 0° C., during which time the solids dissolved. After 45 minutes, the reaction was quenched with saturated aqueous $NH_4Cl$. The organic layer was diluted with ethyl acetate, washed sequentially with dilute HCl and brine, dried over $MgSO_4$ and concentrated in vacuo. The crude mixture was washed with ether to remove unreacted starting ketone and the yellow solid (11.3 g) used without further purification. The crude mixture (11.3 g) was stirred with 60 mL glacial acetic acid and 4.5 mL hydrazine hydrate at reflux under nitrogen for 18 hours. The acetic acid was then removed in vacuo, and the residue dissolved in ethyl acetate, washed sequentially with dilute HCl and brine, dried over $MgSO_4$ and reconcentrated in vacuo. Recrystallization from chloroform-hexane gave 8.24 g of the pyrazole as a pale yellow solid. Elemental analysis for $C_{17}H_{12}N_2F_4S$ Calc'd.: C, 57.95, H, 3.43, N, 7.95, S, 9.10. Found: C, 57.58, H, 3.50, N, 7.88, S, 8.97.

Step 3:

Preparation of 4-(4-fluorophenyl)-3-3-[4-(methylsulfonyl)phenyl]-5-(trifluoromethyl)-1H-pyrazole To a solution of the pyrazole from Step 2 (4.0 g, 11.4 mmol) in 150 mL methanol was added a solution of Oxone® (14.0 g, 22.7 mmol) in 50 mL water. After 1 hour the solids were filtered off, washed with ethyl acetate and the filtrate concentrated in vacuo. This mixture was partitioned between ethyl acetate and water, and the organic layer washed with brine, dried over $MgSO_4$ and reconcentrated in vacuo. Recrystallization from chloroform gave 4-(4-fluorophenyl)-3-[4(methylsulfonyl)phenyl]-5-(trifluoromethyl)-

1H-pyrazole (3.98 g, 91%) as a pale yellow solid: mp 219°–220° C. Elemental analysis for $C_{17}H_{12}N_2F_4SO_2$ Calc'd.: C, 53.12, H, 3.15, N, 7.29, S, 8.34. Found: C, 52.85, H, 3.12, N, 7.21, S, 8.61

Step 4:

Preparation of 1-ethyl-4-(4-fluorophenyl)-3-[4-(methylsulfonyl)phenyl]- 5-(trifluoromethyl)-1H-pyrazole 4-(4-Fluorophenyl)-3-[4(methylsulfonyl)phenyl]-5-( trifluoromethyl)-1pyrazole (1.81 g, 4.3 mmol) and ethyl iodide (0.86 g, 5.5 mmol) were stirred vigorously in 20 mL dry dimethylformamide (DMF) with finely powdered potassium carbonate (0.58 g, 4.2 mmol) under nitrogen at 25° C. for 18 hours. The mixture was diluted with ethyl acetate and filtered to remove solids. The organic filtrate was washed with two portions of water followed by brine, dried over $MgSO_4$ and concentrated in vacuo. The desired 1-ethyl-4-(4-fluorophenyl)-3-[4(methylsulfonyl)phenyl]-5-(trifluoromethyl)-1H-pyrazole was isolated by chromatography on silica gel using 10% ethyl acetate90% toluene as the eluant, giving 0.65 g (69%) of a white solid: mp 133°–135 . 5° C.

EXAMPLE 2

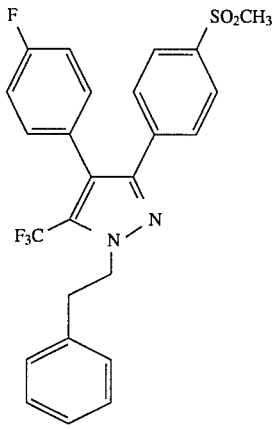

4-(4-Fluorophenyl)-3-[4-(methylsulfonyl)phenyl]-1-(2-phenylethyl)-5-(trifluoromethyl)pyrazole 4-(4-Fluorophenyl)-3-[4-(methylsulfonyl) phenyl]-5-(trifluoromethyl)-1H-pyrazole (Example 1, Step 3) (0.10 g) was reacted with potassium carbonate (0.065 g) and 2-bromoethylbenzene (0.67 g) in 5 mL of DMF to give a crude mixture of 4-(4-fluorophenyl)-3-[4-(methylsulfonyl)phenyl]-1-(2-phenylethyl)-5-(trifluoromethyl)pyrazole and 4-(4-fluorophenyl)-5-[4-(methylsulfonyl)phenyl]-1-(2-phenylethyl)-3(trifluoromethyl)pyrazole. High pressure liquid chromatography (HPLC) purification gave 4-(4-fluorophenyl)-3-[4-(methylsulfonyl)phenyl]-1-(2-phenylethyl)-5-(trifluoromethyl)pyrazole(57 rag, 45%), in the first fraction and 32 mg (25%) of 4-(4-fluorophenyl)-5-[4-(methylsulfonyl)phenyl]-1-(2-phenylethyl)-3-(trifluoromethyl)pyrazole, in the second fraction. 4-(4-Fluorophenyl)-3-[4-(methylsulfonyl)phenyl]- 1-(2-phenylethyl)-5(trifluoromethyl)pyrazole was crystallized from ether-hexane: mp 131.5°135° C. 4-(4-Fluorophenyl)-5-[4-(methylsulfonyl)phenyl]-1-(2-phenylethyl)-3-(trifluoromethyl)pyrazole was crystallized from ether-hexane: mp 148.5°–149.5° C.

EXAMPLE 3

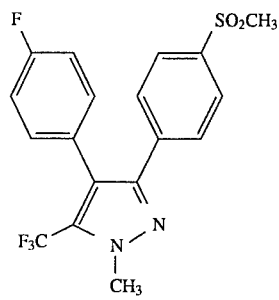

4-(4-Fluorophenyl)-1-methyl-3-[4(methylsulfonyl)phenyl]-5-(trifluoromethyl)pyrazole Step 1:

Preparation of 3-amino-4,4,4-trifluoro-2(4-fluorophenyl)-1-[4-(methylthio)pheny]-2-buten-1-one A solution of 2-(4-fluorophenyl)-1-[4-(methythio)phenyl] ethanone (Example 1, Step 1) (21.4 g, 0.082 tool) in 150 ml of DMF was added under nitrogen to a mixture of 80% sodium hydride oil dispersion (2.6 g, 0.087 mol) and 10 mL of DMF in 30 minutes. The resulting mixture was stirred at room temperature for 1 hour. To the above mixture was passed 10 g (0.11 mol) of gaseous trifluoroacetonitrile in 40 minutes while the reaction mixture was analyzed by thin layer chromatography (TLC). The reaction mixture was poured into 400 mL of water and the solid precipitate was filtered and air dried. The solid precipitate was stirred with 300 mL of ether and filtered. The ether filtrate was dried over MgSO4 and concentrated in vacuo. The residue was recrystallized from 5% ethyl acetate-hexane to give 2.3 g of a 6:1 mixture of 3-amino-4,4,4-trifluoro-(4-fluorophenyl)-1-[4-(methylthio)phenyl]-2-buten-1-one and 5-(4-fluorophenyl)-4-[4-(methylthio)-phenyl]-2,6-bis(trifluoromethyl)pyrimidine. This mixture was heated with 100 mL of ether, cooled and filtered. The ether liltrate was concentrated and the residue was recrystallized from 10% ethyl acetate-hexane to give 3-amino-4,4,4-trifluoro-2-(4-fluorophenyl)-1-[4-(methylthio)phenyl]-2-buten-1-one (10.5 g, 36%): mp 122.5°–124.5 ° C. The combined ethyl acetate-hexane mother liquor was concentrated in vacuo and the residue was purified by HPLC (10% ethyl acetate-hexane). The first fraction gave 5.8 g (16%) of 5-(4-fluorophenyl)-4-[4-(methylthio)phenyl]-2,6-bis(trifluoromethyl)pyrimidine after recrystallization from 5% ethyl acetate-hexane. The second fraction gave an additional 2.6 g (9%) of 3-amino-4,4,4-trifluoro-2-(4-fluorophenyl)-1-[4(methylthio)phenyl]-2-buten-1-one after recrystallization from 5% ethyl acetate-hexane.

Step 2:

Preparation of 4-(4-fluorophenyl)-1-methyl-3-[4-(methylthio)phenyl]-5-(trifluoromethyl)pyrazole The ketone from Step 1 (0.35 g) was reacted with 8 mL of 6N HCl and 30 mL of ether for 24 hours. The ether layer was separated, dried over $MgSO_4$, and concentrated in vacuo. The residue (mainly 2-(4-fluorophenyl)-1-[4-(methylthio)phenyl]-4,4,4-trifluoro-1,3-butanedione) was dissolved in 5-10-mL of glacial acetic acid, treated with methylhydrazine (0.4 g) and heated to 110° C. for 18 hours and poured into water. The resulting oil (0.36 g) was extracted into methylene chloride, dried over MgSO4 and concentrated in vacuo to give a mixture of 4-(4-fluorophenyl)-1-methyl-3-[4-(methylthio)phenyl]-5 -(trifluoromethyl) pyrazole and 4-(4-fluorophenyl)-1-methyl-5-[4-(methylthio)phenyl]-3-(trifluoromethyl)pyrazole.

Purification by HPLC (20% ethyl acetate-hexane) gave 4-(4-fluorophenyl)-1-methyl-3-[4-(methylthio)phenyl]-5-(trifluoromethyl) pyrazole in the first fraction (25 mg, 7%, mp 100°–104° C.) and 4-(4-fluorophenyl)-1-methyl- 5-[4-(methylthio)phenyl]3-(trifluoromethyl)pyrazole (0.2 g, 54%) in the second fraction.

Step 3:

Preparation of 4-(4-fluorophenyl)-1-methyl-3-[4-(methylsulfonyl) phenyl]-5-(trifluoromethyl)pyrazole To a solution of pyrazole from Step 2 (0.55 mmoles) in glacial acetic acid (5 mL) was added 4 mmoles of 30% hydrogen peroxide. The reaction mixture was stirred at room temperature for 18 hours and poured into water. The insoluble precipitate was filtered, air dried and recrystallized from an appropriate solvent or further purified by HPLC followed by recrystailization from an appropriate solvent. The crude product was purified by chromatotron (40% ethyl acetate-hexane) followed by recrystallization from ether-hexane to give white prisms (44%): mp 165.5°169° C.

EXAMPLE 4

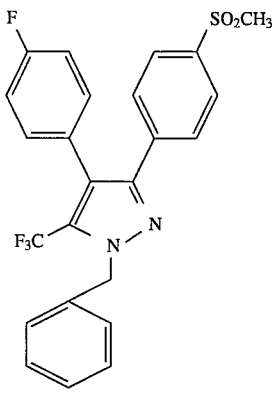

1-Benzyl-4-(4-fluorophenyl)-3-[4-(methylsulfonyl) phenyl]-5-(trifluoromethyl)pyrazole A mixture of 0.10 g of 4-(4-fluorophenyl)-3-[4-(methylsulfonyl)phenyl]-5-(trifluoromethyl)-1H-pyrazole (Example 1, Step 3) and 3.0 g of benzyl bromide was heated at 140° C. for 4 days then at 210° C. for 1 hour. The reaction mixture was dissolved in 10% ethyl acetate-hexane and filtered. The filtrate was concentrated in vacuo and the residue was purified by HPLC (10% ethyl acetate-hexane). The first fraction was benzyl bromide. The second fraction eluted with 30% ethyl acetate-hexane yielded 1-benzyl-4- (4-fluorophenyl)-3-[4-(methylsulfonyl)phenyl]-5-(trifluoromethyl)pyrazole (60 mg, 49%): mp 125.5°–126.5° C.

EXAMPLE 5

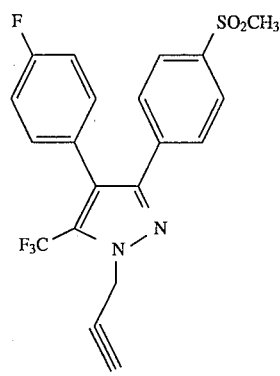

4-(4-Fluorophenyl)-3-[4-(methylsulfonyl)phenyl]-1 -propargyl-5-(trifluoromethyl)-1H-pyrazole Step 1:

Preparation of 4-(4-fluorophenyl)-3-[4-(methylthio)phenyl]- 5-(trifluoromethyl)-1H-pyrazole Crude 2-(4-fluorophenyl)-1-[4-(methylthio)phenyl]-4,4,4-trifluoro-1,3-butanedione (Example 3, Step 2) (1.0 g) was reacted with anhydrous hydrazine (0.13 g) in glacial acetic acid. The mixture was held at 80°–110° C. for 18 hours and poured into water. The resulting solid precipitate was filtered, purified by HPLC and recrystallized from methylene chloride-hexane to give 4-(4-fluorophenyl)-3-[4-(methylthio)phenyl]-5-(trifluoromethyl)-1H-pyrazole as a solid (0.88 g, 89%): mp 189°–190° C.

Step 2:

Preparation of 4-(4-fluorophenyl)-3-[4-(methylthio)phenyl]- 1-propargyl-5-(trifluoromethyl)pyrazole 4-(4-Fluorophenyl)-3-[4-(methylthio)phenyl]-5-(trifluoromethyl)-1H-pyrazole (0.15 g) from step 1 was added to potassium carbonate (0.14 g) and propargyl bromide (0.45 g) in 5 mL of DMF. HPLC purification gave 4-(4-fluorophenyl)-3-[4-(methylthio)phenyl]-1-propargyl-5-(trifluoromethyl)pyrazole (35 mg, 22%) in the first fraction (mp 144.5°–146° C.) and 4-(4-fluorophenyl)-5-[4-(methylthio)phenyl]-1-propargyl-3-(trifluoromethyl)-1H-pyrazole in the second fraction (87 mg, 56%, mp 135.5°–138.5° C.) .

Step 3:

Preparation of 4-(4-fluorophenyl)-3-[4-(methylsulfonyl)phenyl]- 1-proparoyl-5-(trifluoromethyl)-1H-pyrazole To a solution of 0.066 mmol of 4-(4-fluorophenyl)-3-[4-(methylthio)phenyl]-1-propargyl-5-(trifluoromethyl)pyrazole from step 2 in 5 mL of glacial acetic acid was added 13 mmol of 30% hydrogen peroxide. The reaction mixture was stirred at room temperature for 72 hours and poured into water. The crude product was purified by HPLC (40% ethyl acetate-hexane) followed by recrystallization from methylene chloride-hexane to give 4-(4-fluorophenyl)-3-[4-(methylsulfonyl)phenyl]-1-propargyl-5-(trifluoromethyl)-1H-pyrazole as white needles (21%): mp 158°–159.5° C.

EXAMPLE 6

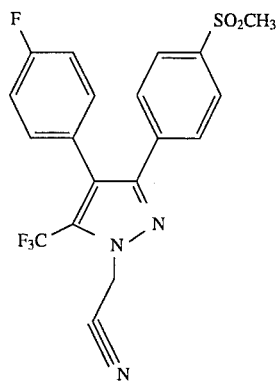

1-Cyanomethyl-4-(4-fluorophenyl)-3-[4-(methylsulfonyl)phenyl]-5-(trifluoromethyl)-1H-pyrazole A mixture of 4-(4-fluorophenyl)-3-[4-(methylsulfonyl)phenyl]-5-(trifluoromethyl)-1H-pyrazole (Example 1, step 3)(0.10 g), 4.2 g of bromoacetonitrile and 3 mL of toluene was heated at reflux for 2 hours. Toluene was distilled off and the mixture was heated at 190° C. for 24 hours. The reaction mixture was diluted with methylene chloride and filtered through silica gel. The filtrate was concentrated in vacuo and the residue was purified by HPLC (30% ethyl acetate-hexane). The second fraction eluted with 40% ethyl acetate-hexane yielding 1-cyanomethyl-4-(4-fluorophenyl)-3-[4-(methylsulfonyl)phenyl]-5-(trifluoromethyl)-1H-pyrazole (12 mg, 11%): mp 192°–194° C.

EXAMPLE 7

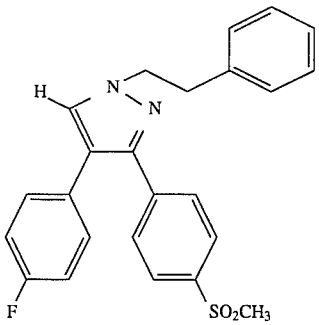

4-(4-Fluorophenyl)-3-[4-(methylsulfonyl)phenyl]-1-(2-phenylethyl)-1H-pyrazole

Step 1:

Preparation of 3-(dimethylamino)-2-(4-fluorophenyl)-1-[4-(methylthio)phenyl]prop-2-en-1-one 2-(4-Fluorophenyl)-1-[4-(methylthio)phenyl]ethanone from Example 1, Step 1 (17.2 g, 66 mmol) was stirred with 15 mL dimethylformamide dimethylacetal in 80 mL dry DMF at 120° C. for 24 hours under nitrogen. The reaction mixture was cooled, diluted with two volumes of ethyl acetate, and the solution washed successively with water and brine and dried over $Na_2SO_4$. The solvent was removed under high vacuum and the resulting brown oil (23.9 g) was used in the next step without further purification.

Step 2:

Preparation of 4-(4-fluorophenyl)-3-[4-(methylthio)phenyl]-1H-pyrazole

The crude ketone from step 1 (23.9 g) was stirred in 500 mL methanol and 100 mL water with 8 mL hydrazine hydrate at reflux under nitrogen for 24 hour. The mixture was cooled, concentrated, diluted with ethyl acetate, washed successively with 1N HCl and brine, dried over $MgSO_4$ and concentrated in vacuo. Recrystallization from ethyl acetate-hexane gave 4-(4-fluorophenyl)-3-[4-(methylthio)phenyl]-1H-pyrazole as a pale yellow solid (16.9 g, 90.1%). Elemental analysis Calc'd for $C_{16}H_{13}N_2FS$: C, 67.58, H, 4.61, N, 9.85, S, 11.28. Found: C, 67.44, H, 4.76, N, 9.69, S, 11.27.

Step 3:

Preparation of 4-(4-fluorophenyl)-3-[4-(methysulfonyl)phenyl]-1H-pyrazole

The sulfide from the previous step (0.57 g, 2 mmol) was stirred in 20 mL methanol and a solution of Oxone® (2.46 g, 4 mmol) in 8 mL water was added. After 1 hour, the solids were filtered off and washed with ethyl acetate and the filtrate concentrated in vacuo. The residue was partitioned between ethyl acetate and water and the organic layer was washed with brine, dried over $MgSO_4$ and concentrated in vacuo to give 4-(4-fluorophenyl)-3-[4-(methylsulfonyl)phenyl]-1H-pyrazole as a pale yellow solid (0.61 g, 97%). Elemental analysis for $C_{16}H_{13}N_2FSO_2$ Calc'd: C, 60.75, H, 4.14, N, 8.86, S, 10.14. Found: C, 59.91, H, 4.29, N, 8.50, S, 10.13.

Step 4:

Preparation of 4-(4-fluorophenyl)-3-[4-(methylsulfonyl)phenyl]-1-(2-phenylethyl)-1H-pyrazole 0.47 g (1.5 mmol) of 4-(4-fluorophenyl)-3-[4-(methylsulfonyl)phenyl]-1H-pyrazole from step 3, 2-bromoethylbenzene (0.42 g, 2.3 mmol) and sodium iodide (0.04 g) were stirred vigorously in 5 mL dry DMF with finely powdered potassium carbonate (0.41 g, 3 mmol) at 50° C. under nitrogen for 18 hours. The mixture was cooled, diluted with ethyl acetate and filtered to remove solids. The organic filtrate was washed with two portions of water followed by brine, dried over $MgSO_4$ and concentrated. The desired 1-phenylethyl isomer was isolated by recrystallization from ethyl acetate-hexane to give 4-(4-fluorophenyl)-3-[4-(methylsulfonyl)phenyl]-1-(2-phenylethyl)-1H-pyrazole as white crystals (0.30 g, 71%): mp 170°–171° C. Elemental analysis for $C_{24}H_{21}N_2FSO_2$ Calc'd: C, 68.55, H, 5.03, N, 6.66. Found: C, 68.49, H, 5.36, N, 6.58.

EXAMPLE 8

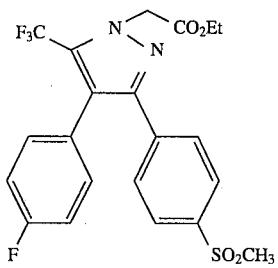

Ethyl
[4-(4-fluorophenyl)-3-[4-(methylsulfonyl)phenyl]-
5-(trifluoromethyl)-1H-pyrazol-1-yl]acetate 4-(4-Fluorophenyl)-3-[4-(methylsulfonyl)phenyl]-5-(trifluoromethyl)-1H-pyrazole (Example 1, Step 3) (2.11 g, 5.5 mmol) and ethyl bromoacetate (1.09 g, 6.5 mmol) were stirred vigorously in 15 mL dry DMF with finely powdered potassium carbonate (1.38 g, 10 mmol) under nitrogen at 25° C. for 3 hours. The mixture was diluted with ethyl acetate and filtered to remove solids. The organic filtrate was washed with two portions of water followed by brine, dried over $MgSO_4$ and concentrated in vacuo. The desired isomer was isolated by chromatography on silica gel, using 10% ethyl acetate/90% heptane as the eluant, to give ethyl [4-(4-fluorophenyl)-3-[4-(methylsulfonyl)phenyl]-5-(trifluoromethyl)-1H-pyrazol-1-yl]acetate as a white solid (0.87 g, 34%). Elemental analysis for $C_{21}H_{18}N_2F_4SO_4$ Calc'd: C, 53.62, H, 3.86, N, 5.96, S, 6.82. Found: C, 53.69, H, 3.97, N, 5.87, S, 7.05.

EXAMPLE 9

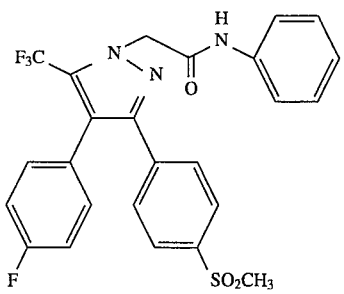

N-Phenyl-[4-(4-luorophenyl)-3-[4-(methylsulfonyl)phenyl]-5-(trifluoromethyl)-
1-H-pyrazol-1-yl]acetamide Aniline (0.07 g, 0.75 mmol) was added to a methylene chloride solution of trimethyl aluminum (0.38 mL, 0.75 mmol, 2.0M in hexanes) at 25° C. under nitrogen. After gas evolution had ceased (approx. 30 minutes), ethyl [4-(4-fluorophenyl)-3-[4-(methylsulfonyl)phenyl]-5-(trifluoromethyl)-1H-pyrazol-1-yl]acetate (Example 8) (0.25 g, 0.5 mmol) was added and the mixture stirred for 24 hours at 25° C. The reaction was quenched with dilute aqueous HCl and extracted with two portions ethyl acetate and the extracts washed with brine, dried over $MgSO_4$ and concentrated in vacuo. Recrystallization from chloroform/acetone gave N-phenyl-[4-(4-fluorophenyl)-3-[4-(methylsulfonyl)phenyl]-5-(trifluoromethyl)-1H-pyrazol-1-yl]acetamide as a white crystalline solid (0.18 g, 68% yield). Elemental analysis for $C_{25}H_{19}N_3F_4SO_3$ Calc'd: C, 58.02, H, 3.70, N, 8.12, S, 6.20. Found: C, 57.48, H, 3.78, N, 8.03, S, 6.46.

EXAMPLE 10

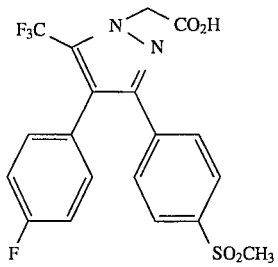

[4-(4-Fluorophenyl)-3-[4-(methylsulfonyl)phenyl]-
5-(trifluoromethyl)-1H-pyrazol-1-yl]acetic acid To a solution of ethyl [4-(4-fluorophenyl)-3-[4-(methylsulfonyl)phenyl]-5-(trifluoromethyl)-1H-pyrazol-1-yl]acetate (Example 8) (0.48 g, 1.0 mmol) in tetrahydrofuran (THF) (10 mL) was added 1.5 mL of 1N aqueous lithium hydroxide at 25° C. under nitrogen and the mixture stirred for 24 hours at 25° C. The reaction mixture was extracted with two portions diethyl ether and the aqueous layer was acidified with dilute aqueous HCl. This was extracted with two portions ethyl acetate which was washed with brine, dried over $MgSO_4$ and concentrated in vacuo. Recrystallization from chloroform/acetone gave [4-(4-fluorophenyl)-3-[4-(methylsulfonyl)phenyl]-5-(trifluoromethyl)-1H-pyrazol-1-yl]acetic acid as a white crystalline solid (0.41 g, 93%). Elemental analysis for $C_{19}H_{14}N_2F_4SO_4$ Calc'd: C, 51.58, H, 3.19, N, 6.33. Found: C, 51.18, H, 3.23, N, 6.19;

EXAMPLE 11

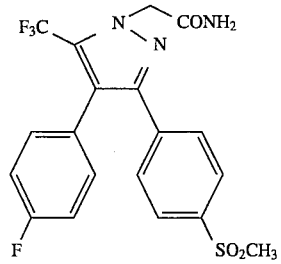

[4-(4-Fluorophenyl)-3-[4-(methylsulfonyl)phenyl]-5
-(trifluoromethyl)-1H -pyrazol-1-yl]acetamide To a solution of [4-(4-fluorophenyl)-3-[4-(methylsulfonyl)phenyl]-5-(trifluoromethyl)-1H-pyrazol-1-yl]acetic acid (Example 10) (0.24 g, 0.54 mmol) in THF (6 mL) was added 0.10 g of 1,1'-carbonyidiimidazole at 25° C. under nitrogen. After gas evolution had ceased (approx. 30 minutes), 6 mL conc. ammonium hydroxide was added and the mixture stirred at 25° C. for 18 hours. The reaction mixture was diluted with water, extracted with two portions ethyl acetate and the organic layer washed successively with dilute aqueous HCl and brine, dried over $MgSO_4$ and concentrated in vacuo. Recrystallization from chloroform/acetone gave [4-(4-fluorophenyl)-3-[4-(methylsulfonyl)phenyl]-5-(trifluoromethyl)-1H-pyrazol-1-yl]acetamide as a white crystalline solid (0.15 g, 34%). Elemental analysis for $C_{19}H_{15}N_3F_4SO_3$ Calc'd: C, 51.70, H, 3.42, N, 9.52. Found: C, 51.46, 3.35, N, 9.39.

EXAMPLE 12

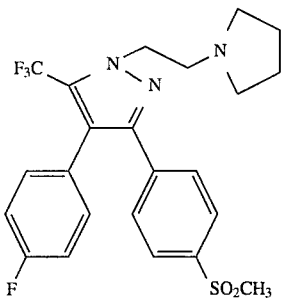

4-(4-Fluorophenyl)-3-[4-(methylsulfonyl)phenyl]-1-[2-(1H-pyrrolidin-1-yl)ethyl]-5-(trifluoromethyl)-1H-pyrazole 4-(4-Fluorophenyl)-3-[4-(methylsulfonyl)phenyl]-5-(trifluoromethyl)-1H-pyrazole (Example 1, Step 3) (0.84 g, 2.2 mmol) was added to N-(2-chloroethyl)pyrrolidine hydrochloride (0.51 g, 3 mmol) and tetrabutylammonium iodide (0.1 g) and were stirred vigorously in 10 mL dry DMF with finely powdered potassium carbonate (0.69 g, 5 mmol) under nitrogen at 60° C. for 18 hours. The mixture was cooled, diluted with ethyl acetate and filtered to remove solids. The organic filtrate was washed successively with two portions of water followed by brine, dried over $MgSO_4$ and concentrated in vacuo. The desired isomer was isolated by chromatography on silica gel using 5:95:1 acetone/toluene/$NH_4OH$ as the eluant, to give 4-(4-fluorophenyl)-3-[4-(methylsulfonyl)phenyl]-1-[2-(1H-pyrrolidin-1-yl)ethyl]- 5-(trifluoromethyl)-1H-pyrazole as white crystals (0.55 g, 52%): mp 134°–135° C. Elemental analysis for $C_{23}H_{23}N_3F_4SO_2$ Calc'd: C, 57.37, H, 4.82, N, 8.73, S, 6.66. Found: C, 57.41, H, 4.77, N, 8.72, S, 6.83.

EXAMPLE 13

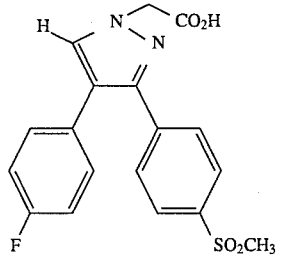

[4-(4-Fluorophenyl)-3-[4-(methylsulfonyl)phenyl]-1H-pyrazol-1-yl]acetic acid

Step 1:

Preparation of ethyl [4-(4-fluorophenyl)-3-[4-(methylsulfonyl)phenyl]-1H-pyrazol-1-yl]acetate 4-(4-Fluorophenyl)-3-[4-(methylsulfonyl)phenyl]-1H-pyrazole (Example 7, Step 3) (1.26g, 4.0 mmol) and ethyl bromoacetate (0.89 g, 5.3 mmol) were stirred vigorously in 12 mL dry DMF with finely powdered potassium carbonate (1.10 g, 8 mmol) at 25° C. under nitrogen for 3 hours. The mixture was diluted with ethyl acetate and filtered to remove solids. The organic filtrate was washed successively with two portions of water followed by brine, dried over $MgSO_4$ and concentrated in vacuo. The desired 1-alkyl isomer was isolated by recrystallization from ethyl acetate-hexane-acetone to give ethyl [4-(4-fluorophenyl)-3-[4-(methylsulfonyl)phenyl]-1H-pyrazol-1-yl]acetate as white crystals (1.11 g, 69%): mp 116°–118° C. Elemental analysis for $C_{20}H_{19}N_2FSO_4$ Calc'd: C, 59.69, H, 4.76, N, 6.96, S, 7.97 . Found: C 59.68, H, 5.04, N, 6.52, S, 7.38.

Step 2:

Preparation of [4-(4-fluorophenyl)-3-[4-(methylsulfony)phenyl]-1H-pyrazol-1-yl]aceticacid To a solution of ethyl [4-(4fluorophenyl)-3-[4-(methylsulfonyl)phenyl]-1H-pyrazol-1-yl]acetate from Step 1 (1.05 g, 2.6 mmol) in THF (20 mL) was added 3.0 mL of aqueous 1N lithium hydroxide at 25° C. under nitrogen and the mixture stirred at 25° C. for 24 hours. The mixture was acidified with 2N HCl, extracted with two portions ethyl acetate and the organic layer separated, washed with brine, dried over $MgSO_4$ and concentrated in vacuo. Chromatographic purification on silica gel using 20% ethanol/79% chloroform/1% acetic acid as the eluant gave [4-(4-Fluorophenyl)-3-[4-(methylsulfonyl)phenyl]-1H-pyrazol-1-yl] acetic acid as a white solid (0.58 g, 60%). Elemental analysis . for $C_{18}H_{15}N_2FSO_4+0.8$ $CH_3CO_2H$ Calc'd: C, 55.73, H, 4.34, N, 6.63, S, 7.59. Found: C, 55.72, H, 4.35, N, 6.74, S, 7.72.

EXAMPLE 14

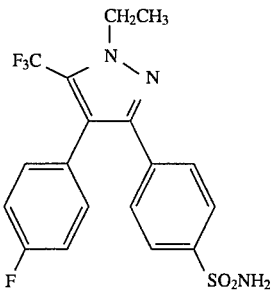

4-[1-Ethyl-4-(4-fluorophenyl)-5-(trifluoromethyl)-1H-pyrazol-3-yl]benzenesulfonamide 1-Ethyl-4-(4-fluorophenyl)-3-[4-(methylsulfonyl)phenyl]- 5-(trifluoromethyl)-1H-pyrazole (0.45 g, 1.0 mmol) was dissolved in 5 mL dry THF under nitrogen and treated with 0.9 mL of a 1.0M solution of n-butyl magnesium chloride in THF at 0° C. for 10 minutes and warmed to 25° C. for 30 minutes. A solution of triethylborane in THF (2.5 mL, 1.0M) was added and the mixture was stirred at 25° C. for 2 hours and at reflux for 24 hours. After cooling to 25° C., a mixture of water (1.2 mL), sodium acetate (0.90 g) and hydroxylamine-O-sulfonic acid (0.62 g) was added and the reaction stirred at 25° C. for 18 hours. The mixture was partitioned between water and ethyl acetate, and the organic layer washed successively with water and brine, dried over $MgSO_4$ and concentrated in vacuo. Chromatographic purification on silica gel eluting with methyl t-butyl ether/toluene (5/95) gave 4-[1-ethyl-4-(4-fluorophenyl)-5-(trifluoromethyl)-1H-pyrazol-3-yl]benzenesulfonamide as a white solid (0.25 g, 62% yield). Elemental analysis for $C_{18}H_{15}N_3F_4SO_2$ Calc'd: C, 52.30, H, 3.66, N, 10.16, S, 7.76. Found: C, 52.36, H, 3.72, N, 9.98, S, 7.90.

EXAMPLE 15

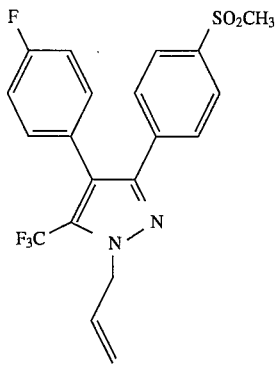

1-Allyl-4-(4-fluorophenyl)-3-[4-(methylsulfonyl) phenyl]-5-(trifluoromethyl)-1H-pyrazole Reaction of 4-(4-fluorophenyl)-3-[4-(methylsulfonyl)phenyl]-5-(trifluoromethyl)-1H-pyrazole (Example 1, Step 3) (0.1 g) with 0.08 g of potassium carbonate and 2.0 g of allyl bromide in 5 mL of DMF gave a crude mixture of 1-allyl-4-(4fluorophenyl)-5-[4-(methylsulfonyl)phenyl]-3-(trifluoromethyl)pyrazole and 1-allyl-4-(4-fluorophenyl)-3-[4-(methylsulfonyl)phenyl]-5-(trifluoromethyl)-1H-pyrazole. HPLC purification with 50% ethyl acetate-hexane and recrystallization from ether-hexane gave 1-allyl-4-(4-fluorophenyl)-3-[4-(methylsulfonyl)phenyl]-5-(trifluoromethyl)-1H-pyrazole (45 mg, 41% ): mp 115.5°–119° C.

BIOLOGICAL EVALUATION

Rat Carrageenan Foot Pad Edema Test

The carrageenan foot edema test was performed with materials, reagents and procedures essentially as described by Winter, et al., (*Proc. Soc. Exp. Biol. Med.,* 111, 544 (1962)). Male Sprague-Dawley rats were selected in each group so that the average body weight was as close as possible. Rats were fasted with free access to water for over sixteen hours prior to the test. The rats were dosed orally (1 mL) with compounds suspended in vehicle containing 0.5% methylcellulose and 0.025% surfactant, or with vehicle alone. One hour later a subplantar injection of 0.1 mL of 1% solution of carrageenan/sterile 0.9% saline was administered and the volume of the injected foot was measured with a displacement plethysmometer connected to a pressure transducer with a digital indicator. Three hours after the injection of the carrageenan, the volume of the foot was again measured. The average foot swelling in a group of drug-treated animals was compared with that of a group of placebo-treated animals and the percentage inhibition of edema was determined (Otterhess and Bliven, *Laboratory Models for Testing NSAIDs,* in *Non-steroidal Anti-Inflammatory Drugs,* (J. Lombardino, ed. 1985)). The % inhibition shows the % decrease from control paw volume determined in this procedure and the data for selected compounds in this invention are summarized in Table 1.

Rat Carrageenan-induced Analgesia Test

The analgesia test using rat carrageenan was performed with materials, reagents and procedures essentially as described by Hargreaves, et al., (*Pain,* 32, 77 (1988)). Male Sprague-Dawley rats were treated as previously described for the Carrageenan Foot Pad Edema test. Three hours after the injection of the carrageenan, the rats were placed in a special plexiglass container with a transparent floor having a high intensity lamp as a radiant heat source, positionable under the floor. After an initial twenty minute period, thermal stimulation was begun on either the injected foot or on the contralateral uninjected foot. A photoelectric cell turned off the lamp and timer when light was interrupted by paw withdrawal. The time until the rat withdraws its foot was then measured. The withdrawal latency in seconds was determined for the control and drug-treated groups, and percent inhibition of the hyperalgesic foot withdrawal determined. Results are shown in Table I.

TABLE I

| | RAT PAW EDEMA % Inhibition @ 20 mg/kg body weight | ANALGESIA % Inhibition @ 20 mg/kg body weight |
|---|---|---|
| Example 11 | 39 | 22 |

Evaluation of COX I and COX II activity in vitro

The compounds of this invention exhibited inhibition in vitro of COX II. The COX II inhibition activity of the compounds of this invention illustrated in the Examples was determined by the following methods.

a. Preparation of recombinant COX baculoviruses

A 2.0 kb fragment containing the coding region of either human or murine COX-I or human or murine COX-II was cloned into a BamH1 site of the baculovirus transfer vector pVL1393 (Invitrogen) to generate the baculovirus transfer vectors for COX-I and COX-II in a manner similar to the method of D.R. O'Reilly et al (*Baculovirus Expression Vectors: A Laboratory Manual* (1992)). Recombinant baculoviruses were isolated by transfecting 4 µg of baculovirus transfer vector DNA into SF9 insect cells (2×10e8) along with 200 ng of linearized baculovirus plasmid DNA by the calcium phosphate method. See M. D. Summers and G. E. Smith, *A Manual of Methods for Baculovirus Vectors and Insect Cell Culture Procedures,* Texas Agric. Exp. Station Bull. 1555 (1987). Recombinant viruses were purified by three rounds of plaque purification and high titer (10E7–10E8 pfu/ml) stocks of virus were prepared. For large scale production, SF9 insect cells were infected in 10 liter fermentors (0.5 x $10^6$/ml) with the recombinant baculovirus stock such that the multiplicity of infection was 0.1. After 72 hours the cells were centrifuged and the cell pellet homogenized in Tris/Sucrose (50 mM: 25%, pH 8.0) containing 1% 3-[(3-cholamidopropyl)dimethylammonio]-1-propanesulfonate (CHAPS). The homogenate was centrifuged at 10,000×G for 30 minutes, and the resultant supernatant was stored at −80° C. before being assayed for COX activity.

b. Assay for COX I and COX II activity:

COX activity was assayed as $PGE_2$ formed/µg protein/time using an ELISA to detect the prostaglandin released. CHAPS-solubilized insect cell membranes containing the appropriate COX enzyme were incubated in a potassium phosphate buffer (50 mM, pH 8.0) containing epinephrine, phenol, and heme with the addition of arachidonic acid (10 µM). Compounds were pre-incubated with the enzyme for 10–20 minutes prior to the addition of arachidonic acid. Any reaction between the arachidonic acid and the enzyme was stopped after ten minutes at 37° C./room temperature by transferring 40 µl of reaction mix into 160 µl ELISA buffer and 25 µM indomethacin. The $PGE_2$ formed was measured by standard ELISA technology (Cayman Chemical). Results are shown in Table II.

TABLE II

| Example | Human COX I $ID_{50}$ µM | Human COX II $ID_{50}$ µM |
|---|---|---|
| 1 | >10 | <.1 |
| 2 | >10 | <.1 |
| 7 | >100 | .5 |
| 8 | >100 | .4 |
| 9 | >100 | .6 |
| 10 | >100 | 23 |
| 11 | >100 | 11 |
| 12 | >100 | 3 |
| 13 | >100 | 76 |
| 14 | 1.3 | <.1 |
| 15 | >10 | <.1 |

Also embraced within this invention is a class of pharmaceutical compositions comprising one or more compounds of Formula I in association with one or more non-toxic, pharmaceutically-acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredient in the range of about 0.1 to 2000 mg, preferably in the range of about 0.5 to 500 mg and most preferably between about 1 and 100 mg. A daily dose of about 0.01 to 100 mg/kg body weight, preferably between about 0.1 and about 50 mg/kg body weight and most preferably between about 1 to 20 mg/kg body weight, may be appropriate. The daily dose can be administered in one to four doses per day.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a conrolled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A compound of Formula I

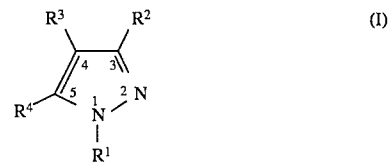

wherein $R^1$ is a radical selected from heterocyclicalkyl, and heteroaralkyl;

wherein $R^2$ is aryl substituted at a substitutable position with a radical selected from alkylsulfonyl and sulfamyl;

wherein $R^3$ is selected from aryl, cycloalkyl, and cycloalkenyl; wherein $R^3$ is optionally substituted at a substitutable position with one or more radicals selected from halo, alkylthio, alkylsulfinyl, alkyl, cyano, carboxyl, alkoxycarbonyl, aminocarbonyl, alkylaminocarbonyl, arylaminocarbonyl, N-alkyl-N-arylaminocarbonyl, haloalkyl, hydroxyl, alkoxy, hydroxyalkyl, haloalkoxy, amino, alkylamino, arylamino, heterocyclo and nitro; and wherein $R^4$ is selected from hydrido, alkyl, haloalkyl, carboxyalkyl, alkoxycarbonylalkyl, aralkoxycarbonylalkyl, aminocarbonylalkyl, hydroxyalkyl and aralkoxyalkyl;

or a pharmaceutically-acceptable salt thereof.

2. Compound of claim 1 wherein $R^1$ is selected from lower heterocyclicalkyl, and lower heteroaralkyl;

wherein $R^2$ is aryl selected from phenyl, naphthyl and biphenyl, wherein $R^2$ is substituted at a substitutable position with a radical selected from lower alkylsulfonyl and sulfamyl;

wherein $R^3$ is selected from aryl, lower cycloalkyl, and lower cycloalkenyl; wherein $R^3$ is optionally substituted at a substitutable position with one or more radicals selected from halo, lower alkylthio, lower alkylsulfinyl, lower alkyl, cyano, carboxyl, lower alkoxycarbonyl, aminocarbonyl, lower alkylaminocarbonyl, lower arylaminocarbonyl, lower N-alkyl-N-arylaminocarbonyl, lower haloalkyl, hydroxyl, lower alkoxy, lower hydroxyalkyl, lower haloalkoxy, amino, lower alkylamino, lower arylamino, heterocyclo and nitro; and wherein $R^4$ is selected from hydrido, lower alkyl, lower haloalkyl, lower carboxyalkyl, lower alkoxycarbonylalkyl, lower aralkoxycarbonylalkyl, lower aminocarbonylalkyl, lower hydroxyalkyl and lower aralkoxyalkyl;

or a pharmaceutically-acceptable salt thereof.

3. Compound of claim 2 wherein $R^1$ is selected from morpholinomethyl, pyrrolidinylmethyl, piperazinylmethyl, piperidinylmethyl, pyridylmethyl, and thienylmethyl;

wherein $R^2$ is aryl selected from phenyl, naphthyl and biphenyl, wherein the aryl radical is substituted at a substitutable position with a radical selected from methylsulfonyl, ethylsulfonyl and sulfamyl;

wherein $R^3$ is selected from phenyl, naphthyl, biphenyl, cyclohexyl, cyclopentyl, cycloheptyl, 1-cyclohexenyl, 2-cyclohexenyl, 3-cyclohexenyl, 4cyclohexenyl, 4-methylcyclohex-4-en-l-yl, and 1-cyclopentenyl; wherein $R^3$ is optionally substituted at a substitutable position with one or more radicals selected from fluoro, chloro, bromo, methylthio, methylsulfinyl, cyano, methyl, ethyl, isopropyl, tert-butyl, isobutyl, carboxyl, aminocarbonyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, N-methylaminocarbonyl, N-ethylaminocarbonyl, N-isopropylaminocarbonyl, N-propylaminocarbonyl, N-butylaminocarbonyl, N-isobutylaminocarbonyl, N-tert-butylaminocarbonyl, N-pentylaminocarbonyl, N,N-dimethylaminocarbonyl, N-methyl-N-ethylaminocarbonyl, N-phenylaminocarbonyl, N-(3-fluorophenyl)aminocarbonyl, N-(4-methylphenyl)aminocarbonyl, N-(3-chlorophenyl)aminocarbonyl, N-(4-methoxyphenyl)aminocarbonyl, N-methyl-N-phenylaminocarbonyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, methoxy, methylenedioxy, ethoxy, propoxy, n-butoxy, trifluoromethoxy, hydroxymethyl, hydroxyethyl, hydroxypropyl, amino, nitro, methylamino, dimethylamino, phenylamino, morpholino, pyrrolidinyl, piperazinyl and piperidinyl;

wherein $R^4$ is selected from hydrido, methyl, ethyl, isopropyl, tert-butyl, isobutyl, methoxy, ethoxy, propoxy, n-butoxy, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxycarbonylalkyl, benzyloxycarbonylmethyl, aminocarbonylmethyl, hydroxypropyl, hydroxymethyl, hydroxyethyl, butanyl, acetyl, propanyl and benzyloxymethyl;

or a pharmaceutically-acceptable salt thereof.

4. Compound of claim 1 wherein $R^2$ is aryl substituted at a substitutable position with alkylsulfonyl; or a pharmaceutically-acceptable salt thereof.

5. Compound of claim 4 wherein $R^1$ is selected from lower heterocyclicalkyl, and lower heteroaralkyl;

wherein $R^2$ is aryl selected from phenyl, naphthyl and biphenyl, wherein the aryl radical is substituted at a substitutable position with lower alkylsulfonyl;

wherein $R^3$ is selected from aryl, lower cycloalkyl, and lower cycloalkenyl; wherein $R^3$ is optionally substituted at a substitutable position with one or more radicals selected from halo, lower alkylthio, lower alkylsulfinyl, lower alkyl, cyano, carboxyl, lower alkoxycarbonyl, aminocarbonyl, lower alkylaminocarbonyl, lower arylaminocarbonyl, lower N-alkyl-N-arylaminocarbonyl, lower haloalkyl, hydroxyl, lower alkoxy, lower hydroxyalkyl, lower haloalkoxy, amino, lower alkylamino, lower arylamino, heterocyclo and nitro; and wherein $R^4$ is selected from hydrido, lower alkyl, lower haloalkyl, lower carboxyalkyl, lower alkoxycarbonylalkyl, lower aralkoxycarbonylalkyl, lower aminocarbonylalkyl, lower hydroxyalkyl and lower aralkoxyalkyl;

or a pharmaceutically-acceptable salt thereof.

6. Compound of claim 5 wherein $R^1$ is selected from morpholinomethyl, pyrrolidinylmethyl, piperazinylmethyl, piperidinylmethyl, pyridylmethyl, and thienylmethyl, wherein $R^2$ is aryl selected from phenyl, naphthyl and biphenyl, wherein the aryl radical is substituted at a substitutable position with methylsulfonyl;

wherein $R^3$ is selected from phenyl, naphthyl, biphenyl, cyclohexyl, cyclopentyl, cycloheptyl, 1-cyclohexenyl, 2-cyclohexenyl, 3-cyclohexenyl, 4-cyclohexenyl, 4-methylcyclohex-4-en-l-yl, and 1-cyclopentenyl; wherein $R^3$ is optionally substituted at a substitutable position with one or more radicals selected from fluoro, chloro, bromo, methylthio, methylsulfinyl, cyano, methyl, ethyl, isopropyl, tert-butyl and isobutyl, carboxyl, aminocarbonyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, N-methylaminocarbonyl, N-ethylaminocarbonyl, N-isopropylaminocarbonyl, N-propylaminocarbonyl, N-butylaminocarbonyl, N-isobutylaminocarbonyl, N-tert-butylaminocarbonyl, N-pentylaminocarbonyl, N,N-dimethylaminocarbonyl, N-methyl-N-ethylaminocarbonyl, N-phenylaminocarbonyl, N-(3-fluorophenyl) aminocarbonyl, N-(4-methylphenyl)aminocarbonyl, N-(3 -chlorophenyl)aminocarbonyl, N-(4 methoxyphenyl)aminocarbonyl, N-methyl-N-phenylaminocarbonyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, methoxy, methylenedioxy, ethoxy, propoxy, n-butoxy, trifluoromethoxy, hydroxymethyl, hydroxyethyl, hydroxypropyl, amino, nitro, methylamino, dimethylamino, phenylamino, morpholino, pyrrolidinyl, piperazinyl and piperidinyl;

wherein $R^4$ is selected from hydrido, methyl, ethyl, isopropyl, tert-butyl, isobutyl, methoxy, ethoxy, propoxy, n-butoxy, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxycarbonylalkyl, benzyloxycarbonylmethyl aminocarbonylmethyl, hydroxypropyl, hydroxymethyl, hydroxyethyl, butanyl, acetyl, propanyl and benzyloxymethyl;

or a pharmaceutically-acceptable salt thereof.

7. Compound of claim 1 wherein $R^2$ is aryl substituted at a substitutable position with sulfamyl; or a pharmaceutically-acceptable salt thereof.

8. Compound of claim 7 wherein $R^1$ is selected from lower heterocyclicalkyl, and lower heteroaralkyl;

wherein $R^2$ is aryl selected from phenyl, naphthyl and biphenyl, wherein the aryl radical is substituted at a substitutable position with sulfamyl;

wherein $R^3$ is selected from aryl, lower cycloalkyl, and lower cycloalkenyl; wherein $R^3$ is optionally substituted at a substitutable position with one or more radicals selected from halo, lower alkylthio, lower alkylsulfinyl, lower alkyl, cyano, carboxyl, lower alkoxycarbonyl, aminocarbonyl, lower alkylaminocarbonyl, lower arylaminocarbonyl, lower N-alkyl-N-arylaminocarbonyl, lower haloalkyl, hydroxyl, lower alkoxy, lower hydroxyalkyl, lower haloalkoxy, amino, lower alkylamino, lower arylamino, heterocyclo and nitro; and wherein $R^4$ is selected from hydrido, lower alkyl, lower haloalkyl, lower carboxyalkyl, lower alkoxycarbonylalkyl, lower aralkoxycarbonylalkyl, lower aminocarbonylalkyl, lower hydroxyalkyl and lower aralkoxyalkyl;

or a pharmaceutically-acceptable salt thereof.

9. Compound of claim 8 wherein $R^1$ is selected from morpholinomethyl, pyrrolidinylmethyl, piperazinylmethyl, piperidinylmethyl, pyridylmethyl, and thienylmethyl;

wherein $R^3$ is selected from phenyl, naphthyl, biphenyl, cyclohexyl, cyclopentyl, cycloheptyl, 1cyclohexenyl, 2-cyclohexenyl, 3-cyclohexenyl, 4-cyclohexenyl, 4-methylcyclohex-4-en-l-yl, and 1-cyclopentenyl; wherein $R^3$ is optionally substituted at a substitutable position with one or more radicals selected from fluoro, chloro, bromo, methylthio, methylsulfinyl, cyano, methyl, ethyl, isopropyl, tert-butyl, isobutyl, carboxyl, aminocarbonyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, N-methylaminocarbonyl, N-ethylaminocarbonyl, N-isopropylaminocarbonyl, N-propylaminocarbonyl, N-butylaminocarbonyl, N-isobutylaminocarbonyl, N-tert-butylaminocarbonyl, N-pentylaminocarbonyl, N,N-dimethylaminocarbonyl, N-methyl-N-ethylaminocarbonyl, N-phenylaminocarbonyl, N-(3fluorophenyl)aminocarbonyl, N-(4-methylphenyl)aminocarbonyl, N-(3-chlorophenyl)aminocarbonyl, N-(4-methoxyphenyl)aminocarbonyl, N-methyl-N-phenylaminocarbonyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, methoxy, methylenedioxy, ethoxy, propoxy, n-butoxy, trifluoromethoxy, hydroxymethyl, hydroxyethyl, hydroxypropyl, amino, nitro, methylamino, dimethylamino, phenylamino, morpholino, pyrrolidinyl, piperazinyl and piperidinyl;

wherein $R^4$ is selected from hydrido, methyl, ethyl, isopropyl, tert-butyl, isobutyl, methoxy, ethoxy, propoxy, n-butoxy, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxycarbonylalkyl, benzyloxycarbonylmethyl, aminocarbonylmethyl, hydroxypropyl, hydroxymethyl, hydroxyethyl, butanyl, acetyl, propanyl and benzyloxymethyl;

or a pharmaceutically-acceptable salt thereof.

10. A compound of Formula II

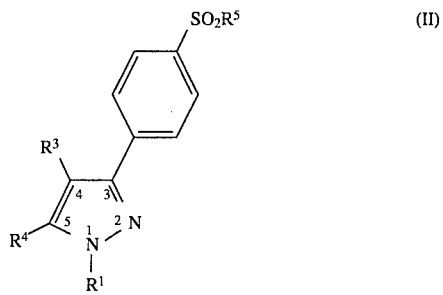

wherein $R^1$ is heterocyclicalkyl;

wherein $R^3$ is aryl substituted at a substitutable position with halo;

wherein $R^4$ is selected from hydrido and haloalkyl; and wherein $R^5$ is selected from alkyl and amino;

or a pharmaceutically-acceptable salt thereof.

11. Compound of claim 10 wherein $R^1$ is lower heterocyclicalkyl; wherein $R^3$ is aryl selected from phenyl, naphthyl and biphenyl, wherein said aryl radical is substituted at a substitutable position with at least one halo radical;

wherein $R^4$ is selected from hydrido and lower haloalkyl; and wherein $R^5$ is selected from lower alkyl and amino;

or a pharmaceutically-acceptable salt thereof.

12. Compound of claim 11 wherein $R^1$ is selected from morpholinomethyl, pyrrolidinylmethyl, piperazinylmethyl, piperidinylmethyl, and tetrahydrofurylmethyl;

wherein $R^3$ is phenyl substituted at a substitutable position with at least one radical selected from fluoro, chloro, bromo and iodo;

wherein $R^4$ is selected from hydrido, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl; and wherein $R^5$ is selected from methyl, and amino; or a pharmaceutically-acceptable salt thereof.

13. Compound of claim 6 selected from compounds, and their pharmaceutically acceptable salts, of the group consisting of 4-(4-fluorophenyl)-3-[4-(methylsulfonyl)phenyl]-1-[2-(2-pyridyl)ethyl]--5-(trifluoromethyl)-1H-pyrazole; 4-(4-fluorophenyl)-3-[4-(methylsulfonyl)phenyl]-1-[2-(1H-pyrrolidin-1-yl)ethyl]-5-(trifluoromethyl)-1H-pyrazole; 4-(4-fluorophenyl)-3-[4-(methylsulfonyl)phenyl]-1-[2-(1H-pyrrolidin-1-yl) ethyl]-1H-pyrazole; and 4-(4-fluorophenyl)-3-[4-(methylsulfonyl) phenyl]-1-[2-(2 pyridyl)ethyl]-1H-pyrazole.

14. Compound of claim 9 selected from compounds, and their pharmaceutically acceptable salts, of the group consisting of -[4-(4-fluorophenyl)-1-[2-(1H-pyrrolidin-1-yl) ethyl]-5-(trifluoromethyl)-1H-pyrazol-3-yl]benzenesulfonamide; [4-(4-fluorophenyl)-1-[2-(2-pyridyl)ethyl]-5-(trifluoromethyl)-1H-pyrazol-3-yl]benzenesulfonamide; [4-(4-fluorophenyl)-1-[2-(1H-pyrrolidin-1-yl) ethyl]-1H-pyrazol-3-yl]benzenesulfonamide; and 4-[4-(4-fluorophenyl)-1-[2-(2-pyridyl)ethyl]-1H-pyrazol-3-yl]benzenesulfonamide.

15. Compound of claim 12 selected from compounds, and their pharmaceutically-acceptable salts, of the group consisting of 4-(4-fluorophenyl)-3-[4-(methylsulfonyl)phenyl]-1-[2-(1H-pyrrolidin-l-yl)ethyl]-5(trifluoromethyl)-1H-pyrazole.

16. A pharmaceutical composition comprising a therapeutically-effective amount of a compound, said compound selected from a family of compounds of claim 1 or a pharmaceutically-acceptable salt thereof.

17. A pharmaceutical composition comprising a therapeutically-effective amount of a compound, said compound selected from a family of compounds of claim 2; or a pharmaceutically-acceptable salt thereof.

18. A pharmaceutical composition comprising a therapeutically-effective amount of a compound, said compound selected from a family of compounds of claim 3 or a pharmaceutically-acceptable salt thereof.

19. A pharmaceutical composition comprising a therapeutically-effective amount of a compound, said compound selected from a family of compounds of claim 13; or a pharmaceutically-acceptable salt thereof.

20. A pharmaceutical composition comprising a therapeutically-effective amount of a compound, said compound selected from a family of compounds of claim 5; or a pharmaceutically-acceptable salt thereof.

21. A pharmaceutical composition comprising a therapeutically-effective amount of a compound, said compound selected from a family of compounds of claim 6; or a pharmaceutically-acceptable salt thereof.

22. A pharmaceutical composition comprising a therapeutically-effective amount of a compound, said compound selected from a family of compounds of claim 14; or a pharmaceutically-acceptable salt thereof.

23. A pharmaceutical composition comprimsing a therapeutically-effective amount of a compound, said compound selected from a family of compounds of claim 7 or a pharmaceutically-acceptable salt thereof.

24. A pharmaceutical composition comprising a therapeutically-effective amount of a compound, said compound selected from a family of compounds of claim 8; or a pharmaceutically-acceptable salt thereof.

25. A pharmaceutical composition comprising a therapeutically-effective amount of a compound, said compound selected from a family of compounds of claim 9; or a pharmaceutically-acceptable salt thereof.

26. A pharmaceutical composition comprising a therapeutically-effective amount of a compound, said compound selected from a family of compounds of claim 15; or a pharmaceutically-acceptable salt thereof.

27. A method of treating inflammation or an inflammation-associated disorder in a subject, said method comprising administering to the subject having such inflammation or inflammation-associated disorder, a therapeutically-effective amount of a compound of claim 1; or a pharmaceutically-acceptable salt thereof.

28. A method of treating inflammation or an inflammation-associated disorder in a subject, said method comprising administering to the subject having such inflammation or inflammation-associated disorder, a therapeutically-effective amount of a compound of claim 2; or a pharmaceutically-acceptable salt thereof.

29. A method of treating inflammation or an inflammation-associated disorder in a subject, said method comprising administering to the subject having such inflammation or inflammation-associated disorder, a therapeutically-effective amount of a compound of claim 3; or a pharmaceutically-acceptable salt thereof.

30. A method of treating inflammation or an inflammation-associated disorder in a subject, said method comprising administering to the subject having such inflammation or inflammation-associated disorder, a therapeutically-effective amount of a compound of claim 13; or a pharmaceutically-acceptable salt thereof.

31. A method of treating inflammation or an inflammation-associated disorder in a subject, said method comprising administering to the subject having such inflammation or inflammation-associated disorder, a therapeutically-effective amount of a compound of claim 5; or a pharmaceutically-acceptable salt thereof.

32. A method of treating inflammation or an inflammation-associated disorder in a subject, said method comprising administering to the subject having such inflammation or inflammation-associated disorder, a therapeutically-effective amount of a compound of claim 6; or a pharmaceutically-acceptable salt thereof.

33. A method of treating inflammation or an inflammation-associated disorder in a subject, said method comprising administering to the subject having such inflammation or inflammation-associated disorder, a therapeutically-effective amount of a compound of claim 14; or a pharmaceutically-acceptable salt thereof.

34. A method of treating inflammation or an inflammation-associated disorder in a subject, said method comprising administering to the subject having such inflammation or inflammation-associated disorder, a therapeutically-effective amount of a compound of claim 7; or a pharmaceutically-acceptable salt thereof.

35. A method of treating inflammation or an inflammation-associated disorder in a subject, said method comprising administering to the subject having such inflammation or inflammation-associated disorder, a therapeutically-effective amount of a compound of claim 8; or a pharmaceutically-acceptable salt thereof.

36. A method of treating inflammation or an inflammation-associated disorder in a subject, said method comprising administering to the subject having such inflammation or inflammation-associated disorder, a therapeutically-effective amount of a compound of claim 9; or a pharmaceutically-acceptable salt thereof. therapeutically-effective amount of a compound of claim 14; or a pharmaceutically-acceptable salt thereof.

37. A method of treating inflammation or an inflammation-associated disorder in a subject, said method comprising administering to the subject having such inflammation or inflammation-associated disorder, a therapeutically-effective amount of a compound of claim 15; or a pharmaceutically-acceptable salt thereof.

38. The method of claim 27 for use in treatment of inflammation.

39. The method of claim 27 for use in treatment of an inflammation-associated disorder.

40. The method of claim 39 wherein the inflammation-associated disorder is arthritis.

41. The method of claim 39 wherein the inflammation-associated disorder is pain.

42. The method of claim 39 wherein the inflammation-associated disorder is fever.

43. A pharmaceutical composition comprising a therapeutically-effective amount of a compound, said compound selected from a family of compounds of claim 10; or a pharmaceutically-acceptable salt thereof.

44. A method of treating inflammation or an inflammation-associated disorder in a subject, said method comprising administering to the subject having such inflammation or inflammation-associated disorder, a therapeutically-effective amount of a compound of claim 10; or a pharmaceutically-acceptable salt thereof.

* * * * *